United States Patent
Elian et al.

(10) Patent No.: US 11,364,323 B2
(45) Date of Patent: Jun. 21, 2022

(54) COMBINATION GRAFTS FOR TISSUE REPAIR OR REGENERATION APPLICATIONS

(71) Applicant: Rejuvablast LLC, Essex Fells, NJ (US)

(72) Inventors: Nicholas Elian, Tenafly, NJ (US); Sean M. O'Connell, Budd Lake, NJ (US); William K. Boss, Jr., Essex Fells, NJ (US)

(73) Assignee: REJUVABLAST LLC, Essex Fells, NJ (US)

( * ) Notice: Subject to any disclaimer, the term of this patent is extended or adjusted under 35 U.S.C. 154(b) by 238 days.

(21) Appl. No.: 16/567,869

(22) Filed: Sep. 11, 2019

(65) Prior Publication Data

US 2020/0086000 A1    Mar. 19, 2020

Related U.S. Application Data

(60) Provisional application No. 62/732,213, filed on Sep. 17, 2018.

(51) Int. Cl.
| | |
|---|---|
| *A61L 27/36* | (2006.01) |
| *C07K 14/50* | (2006.01) |
| *C07K 14/495* | (2006.01) |
| *C07K 14/485* | (2006.01) |
| *A61L 27/38* | (2006.01) |
| *A61L 27/54* | (2006.01) |
| *A61L 27/50* | (2006.01) |
| *C07K 14/54* | (2006.01) |
| *C07K 14/475* | (2006.01) |
| *C07K 14/49* | (2006.01) |
| *C07K 14/51* | (2006.01) |
| *C07K 14/65* | (2006.01) |

(52) U.S. Cl.
CPC ......... *A61L 27/365* (2013.01); *A61L 27/3804* (2013.01); *A61L 27/502* (2013.01); *A61L 27/54* (2013.01); *C07K 14/485* (2013.01); *C07K 14/495* (2013.01); *C07K 14/50* (2013.01); *C07K 14/54* (2013.01); *A61L 2300/414* (2013.01); *A61L 2400/18* (2013.01); *C07K 14/475* (2013.01); *C07K 14/49* (2013.01); *C07K 14/51* (2013.01); *C07K 14/65* (2013.01)

(58) Field of Classification Search
None
See application file for complete search history.

(56) References Cited

U.S. PATENT DOCUMENTS

| | | | |
|---|---|---|---|
| 5,165,928 A | 11/1992 | Smith et al. | |
| 5,618,544 A | 4/1997 | Brown | |
| 5,899,939 A | 5/1999 | Boyce et al. | |
| 6,010,627 A | 1/2000 | Hood, III | |
| 6,214,338 B1 | 4/2001 | Antanavich et al. | |
| 6,303,112 B1 | 10/2001 | Worden | |
| 6,649,072 B2 | 11/2003 | Brandt et al. | |
| 6,979,307 B2 | 12/2005 | Beretta et al. | |
| 7,052,856 B2 | 5/2006 | Ting | |
| 7,544,486 B2 | 6/2009 | Ting et al. | |
| 7,687,462 B2 | 3/2010 | Ting et al. | |
| 7,691,607 B2 | 4/2010 | Ting et al. | |
| 7,708,557 B2 | 5/2010 | Rubbert | |
| 7,747,305 B2 | 6/2010 | Dean et al. | |
| 7,776,361 B2 | 8/2010 | Ting | |
| 7,807,787 B2 | 10/2010 | Ting et al. | |
| 7,833,968 B2 | 11/2010 | Soo et al. | |
| 7,884,066 B2 | 2/2011 | Ting | |
| 8,317,672 B2 | 11/2012 | Nash et al. | |
| 8,398,714 B2 | 3/2013 | Boiangiu et al. | |
| 8,574,825 B2 | 11/2013 | Shelby et al. | |
| 9,155,607 B2 | 10/2015 | Nauman et al. | |
| 9,757,419 B2 | 9/2017 | Duda et al. | |
| 2003/0236573 A1* | 12/2003 | Evans ................... | A61L 31/042 623/23.58 |
| 2004/0071786 A1 | 4/2004 | Grippi et al. | |
| 2005/0244450 A1 | 11/2005 | Reddi | |
| 2006/0128016 A1 | 6/2006 | Tokushima et al. | |
| 2008/0206297 A1* | 8/2008 | Roeder ...................... | C08J 9/28 424/422 |
| 2010/0047309 A1* | 2/2010 | Lu ............................ | A61L 27/54 424/423 |
| 2011/0020216 A1 | 1/2011 | Mooney et al. | |
| 2011/0125306 A1 | 5/2011 | Blay et al. | |

(Continued)

FOREIGN PATENT DOCUMENTS

| | | |
|---|---|---|
| EP | 3284441 A1 | 2/2018 |
| WO | 2013/123448 A1 | 8/2013 |

(Continued)

OTHER PUBLICATIONS

Chen et al. (2012, Acta Biomaterialia 8:2297-2306).*
Deepthi et al. (Jun. 2018, Bioacticve Materials 3:194-200).*
Wung et al. (2014, Biotechnl. Lett. 36:2357-2366).*
Yin et al. (2009, Cryobiology 59:180-187).*
Lekholm, Y., et al., Patient selection and preparation. Tissue integrated prostheses. Chicago: Quntesscence Publishing Co., Inc. (1985), 199-209.
Leppanen, O., et al., Predimerization of Recombinant Platelet-Derived Growth Factor Receptor Extracellular Domains Increases Antagonistic Potency. Biochemistry. Mar. 7, 2000; 39(9):2370-5.
Li, R., et al., Human treated dentin matrix as a natural scaffold for complete human dentin tissue regeneration. Biomaterials, 32; 4525-4538; doi: 10:1016/j.biomaterials 2011.03.008 (2011).

(Continued)

*Primary Examiner* — Elizabeth C. Kemmerer
(74) *Attorney, Agent, or Firm* — McCarter & English, LLP; Beverly W. Lubit

(57) ABSTRACT

The described invention provides soft tissue grafts, hard tissue grafts, and composite soft/hard tissue grafts and methods of producing such grafts. The grafts comprise a three-dimensional carrier matrix, a growth factor composition comprising an autologous platelet-rich fibrin and a cell culture composition comprising a culture medium, a population of cells suspended in the culture medium, and cells impregnated on or in a surface of osteoconductive particles.

39 Claims, No Drawings

(56) References Cited

U.S. PATENT DOCUMENTS

| | | |
|---|---|---|
| 2012/0221118 A1 | 8/2012 | Bartee et al. |
| 2015/0054195 A1 | 2/2015 | Greyf |
| 2015/0374450 A1 | 12/2015 | Mansfield et al. |
| 2016/0022379 A1 | 1/2016 | Keller |
| 2016/0038639 A1 | 2/2016 | Carter et al. |
| 2016/0346091 A1 | 12/2016 | Bin Abdul Rahman et al. |
| 2017/0202645 A1 | 7/2017 | Malinin et al. |
| 2017/0203008 A1 | 7/2017 | Mauth et al. |
| 2017/0312081 A1 | 11/2017 | Namin et al. |
| 2018/0142199 A1 | 5/2018 | Jones et al. |

FOREIGN PATENT DOCUMENTS

| | | |
|---|---|---|
| WO | 2015/002707 A1 | 1/2015 |
| WO | 2015/132432 A1 | 9/2015 |
| WO | 2016/011039 A1 | 1/2016 |
| WO | 2016/139340 A1 | 9/2016 |
| WO | 2016/140638 A1 | 9/2016 |
| WO | 2017/161115 A1 | 9/2017 |
| WO | 2017/161121 A1 | 9/2017 |
| WO | 2018/071319 A1 | 4/2018 |

OTHER PUBLICATIONS

Liang, P. et al., Anti-apoptotic role of EGF in HaCaT keratinocytes via a PPARβ-dependent mechanism. Wound Repair Regen. 2008, 16: 691-698.

Lin, P., et al, Inhibition of tumor growth by targeting tumor endothelium using a soluble vascular endothelial growth factor receptor. Cell Growth Differ. 9: 49-58 (1998).

Lokker, NA., et al., Functional Importance of Platelet-derived Growth Factor (PDGF) Receptor Extracellular Immunoglobulin-like Domains. J. Biol Chem. Dec. 26, 1997; 272(52):33037-44.

Madlener, M. et al, Matrix Metalloproteinases (MMPs) and Their Physiological Inhibitors (TIMPs) Are Differentially Expressed during Excisional Skin Wound Repair. Exp Cell Res, 242, 201-210 (1998).

Madri, J. et al., Angiogenesis in Clark, R. Ed. The molecular and cellular biology of wound repair. 2nd Ed. New York, Plenum Press, pp. 355-371 (1996).

Magnusson, MK et al., Fibronectin Structure, Assembly, and Cardiovascular Implications. Arterio. Thromb. Vasc. Biol. 18:1363-1370 (1998).

Majima, K. Effect of Epidermal Growth Factor upon Morphological Changes of Human Lens Epithelial Cells. Ophthalmologica 1998, 212:250-256.

Majumdar, M.K., et al., Phenotypic and functional comparison of cultures of marrow-derived mesenchymal stem cells (MSCs) and stromal cells. J. Cell Physiol. 176:57-66 (1998).

Makinen, T., et al., Differential Binding of Vascular Endothelial Growth Factor B Splice and Proteolytic Isoforms to Neuropilin-1. J. Biol. Chem. vol. 274, No. 30, 21217-21222 (1999).

Mansbridge, ,J. Commercial considerations in tissue engineering. J. Anat. (2006) 209, pp. 527-532.

Mao, Y. et al., Fibronectin fibrillogenesis, a cell-mediated matrix assembly process. Matrix Biol. 24(6):389-399 (2005).

Martieau, I., et al, "Effects of calcium and thrombin on growth factor release from platelet concentrates: kinetics and regulation of endothelial cell proliferation," Biomaterials 2004; 25: 4489-4502.

Martinsen, A., et al., Alginate as immobilization material: I. Correlation between chemical and physical properties of alginate gel beads, Biotech. Bioeng. 33:79-89 (1989).

Marx, RE, et al, "Platelet-rich plasma: growth factor enhancement for bond grafts," Oral Surg. Oral Med. Oral Pathol. Oral Radiol. Endod. (1998) 85: 638-646.

Matthew, IR et al., Subperiosteal behaviour of alginate and cellulose wound dressing materials. Biomaterials 16:265-74 (1995).

Mercuri, JJ., et al., Novel tissue-derived biomimetic scaffold for regenerating the human nucleus pulposus. J. Biomed. Mater. Res. A., 96(2): 422-435 (2011).

Mercurius, KO., et al., Inhibition of Vascular Smooth Muscle Cell Growth by Inhibition of Fibronectin Matrix Assembly. Circ. Res. 82:548-556 (1998).

Mignatti, P. et al., Proteinases and Tissue Remodeling. In Clark, R. Ed. The molecular and cellular biology of wound repair. 2nd Ed. New York, Plenum Press, 427-474 (1996).

Millauer, B., et al., High affinity VEGF binding and developmental expression suggest Flk-1 as a major regulator of vasculogenesis and angiogenesis. Cell 72: 835-46 (1993).

Miyazono, K., et al., "Bone morphogenetic protein receptors and signal transduction," J. Biochem. (2010) 147 (1): 35-51.

Montesano, R. and Orci, L.,Transforming growth factor beta stimulates collagen-matrix contraction by fibroblasts: implications for wound healing. Proc Natl Acad Sci USA, 85, 4894-4897 (1988).

Moraghebi, R. et al., Term amniotic fluid: an unexploited reserve of mesenchymal stromal cells for reprogramming and potential cell therapy applications. Stem Cell Res. Ther. (2017) 8:190.

Morgan, M.M., et al., Dissociation of hyperalgesia from fever following intracerebroventricular administration of interleukin-1 beta in the rat. Brain Res. 1022(1-2): 96-100 (2004).

Morla, A. et al., Superfibronectin is a functionally distinct form of fibronectin. Nature 367:193-196 (1994).

Mowry, KC., et al. Enhanced Skin Regeneration Using a Novel Amniotic-Derived Tissue Graft. Wounds: A Compendium of Clinical Research and Practice. vol. 29, Issue 9, p. 277-285 (2017).

Muro, AF et al., An Essential Role for Fibronectin Extra Type III Domain A in Pulmonary Fibrosis. Am. J. Resp. Crit. Care Med. 177:638 (2008).

Murray, MM, et al. Enhanced Histologic Repair in a Central Wound in the Anterior Cruciate Ligament with a Collagen-Platelet-Rich Plasma Scaffold. Orthopaedic Research Society. Published by Wiley Periodicals, Inc. J Orthop Res 25:1007-1017, 2007.

Nanney, L. and King, L. Epidermal Growth Factor and Transforming Growth Factor-alpha. In Clark, R. Ed. The molecular and cellular biology of wound repair 2nd Ed. New York, Plenum Press, pp. 171-194 (1996).

Neufeld, G., et al., Vascular endothelial growth factor (VEGF) and its receptors. FASEB J. 13; 9-22 (1999).

Niknejad, H. et al., Properties of the amniotic membrane for potential use in tissue engineering. Eur. Cells and Materials (2008) 15: 88-99.

Nissen, N. et al., Vascular endothelial growth factor mediates angiogenic activity during the proliferative phase of wound healing. Am J Pathol, 152, 1445-1552 (1998).

Okada, F., et al., Impact of oncogenes in tumor angiogenesis: Mutant K-ras up-regulation of vascular endothelial growth factoryvascular permeability factor is necessary, but not sufficient for tumorigenicity of human colorectal carcinoma cells. Proc. Natl Acad Sci. USA 95: 3609-3614 (1998).

Olson, J.L., et al., Tissue Engineering: Current Strategies and Future Directions. Chonnam. Med. J. 47:1-13 (2011).

Otto. S., et al. Custom-milled individual allogeneic bone grafts for alveolar cleft osteoplasty-A technical note. J Craniomaxillofac Surg. Dec. 2017;45(12): 1955-1961. doi: 10.1016/j.jcms.2017.09.011. Epub Sep. 20, 2017.

Paladini, R. et al., Onset of re-epithelialization after skin injury correlates with a reorganization of keratin filaments in wound edge keratinocytes: defining a potential role for keratin 16. J Cell Biol, 132, pp. 381-397 (1996).

Peleg, M.et alUse of corticocancellous allogeneic bone blocks for augmentation of alveolar bone defects. International Journal of Oral and Maxillofacial Implants vol. 25, Issue 1, 2010, pp. 153-162.

Peng, L., et al., Comparative Analysis of Mesenchymal Stem Cells from Bone Marrow, Cartilage, and Adipose Tissue. Stems Cells and Development, 17: 761-774 (2008).

Pereira, M. et al., The incorporation of fibrinogen into extracellular matrix is dependent on active assembly of a fibronectin matrix. J. Cell Sci. 115(Pt 3):609-617 (2002).

Petersen, TE et al., Partial primary structure of bovine plasma fibronectin: Three types of internal homology. Proc. Natl. Acad. Sci. U.S.A. 80:137-141 (1983).

Petit, AM et al., Neutralizing Antibodies against Epidermal Growth Factor and ErbB-2Ineu Receptor Tyrosine Kinases Down-Regulate

(56) References Cited

OTHER PUBLICATIONS

Vascular Endothelial Growth Factor Production by Tumor Cells in Vitro and in Vivo. Am. J Pathol. 151:1523-1530 (1997).
Petrungaro, PS, "Using platelet-rich plasma to accelerate soft tissue maturation in esthetic periodontal surgery," Compend. Contin. Edu. Dent. (2001) 22: 729-746.
Pettersson, EE et al., Cold-insoluble globulin (fibronectin, LETS protein) in normal and diseased human glomeruli: Papain-sensitive attachment to normal glomeruli and deposition in crescents. Clin. Immunol. Immunopath 11:425-436 (1978).
Philipp, W. el al., Expression of Vascular Endothelial Growth Factor and Its Receptors in Inflamed and Vascularized Human Corneas. Invest Ophthalmol Vis Sci. 41:2514-22 (2000).
Pilcher, B. et al., The activity of collagenase-1 is required for keratinocyte migration on a type I collagen matrix. J Cell Biol, 137, pp. 1445-1457 (1997).
Pintucci, G. et al., Angiogenesis and the Fibrinolytic System. Semin Thromb Hemost, 22, 517-524 (1996).
Pittenger, MF., et al., Multilineage Potential of Adult Human Mesenchymal Stem Cells. Science 284:143-47 (1999).
Qiu, Z et al., effects of plasma fibronectin on the healing of full-thickness skin wounds in Streptozotocin-Induced Diabetic Rats. J Surg Res (2007) 138(1):64-70.
Abraham, J. and Klagsburn, M. Modulation of Wound Repair by Members of the Fibroblast Growth Factor family. In Clark, R. Ed. The molecular and cellular biology of wound repair. 2nd Ed. New York, Plenum Press, pp. 195-248 (1996).
Aghideh, AN et al, "Platelet growth factors suppress ex vivo expansion and enhance differentiation of umbilical cord blood CD133+ stem cells to megakaryocyte progenitor cells," Growth Factors 2010; 28(6): 409-16.
Agrawal, M., Agrawal, V., "Platelet Rich Fibrin and its applications in dentistry—a review article," Natl J. Med. Dent. Res. (2014) 2(3): 51-58.
Ahmed, A. et al., Regulation of Placental Vascular Endothelial Growth Factor (VEGF) and Placenta Growth Factor (PlGF) and Soluble Flt-1 by Oxygen—A Review. Placenta 21 SA:S16-24 (2000).
Aiello, LP., et al., Suppression of retinal neovascularization in vivo by inhibition of vascular endothelial growth factor (VEGF) using soluble VEGF-receptor chimeric proteins. Proc. Natl. Acad. Sci USA 92:10457-61 (1995).
Alonso JE et al., The management of complex orthopedic injuries. Surg Clin North Am 1996; 76: 879-903.
Amano, S., et al., Requirement for Vascular Endothelial Growth Factor in Wound- and Inflammation-Related Corneal Neovascularization. Invest Ophthalmol Vis Sci. 39:18-22 (1998).
Ambati, J. et al., Elevated gamma-Aminobutyric Acid, Glutamate, and Vascular Endothelial Growth Factor Levels in the Vitreous of Patients With Proliferative Diabetic Retinopathy. Arch Ophthalmol 115: 1161-66 (1997).
Arbiser, JL, et al.,Oncogenic H-ras stimulates tumor angiogenesis by two distinct pathways. Proc. Natl. Acad. Sci USA 94:861-866 (1997).
Atala, A., et al., Endoscopic Treatment of Vesicoureteral Reflux with a Chondrocyte-Alginate Suspension. J. Urology 152, Issue 2, Part 2. 641-43 (1994).
Auron, PE et al., Human and murine interleukin 1 possess sequence and structural similarities. J. Mol. Cell Immunol., 2: 169-177 (1985).
Autiero, M., et al., Role of PlGF in the intra- and intermolecular cross talk between the VEGF receptors Flt1 and Flk1. Nat. Med 9:936-943 (2003).
Baroli, B. From natural bone grafts to tissue engineering therapeutics: brainstorming on pharmaceutical formulative requirements and challenges. J. Pharm. Sci. (2009) 998: 1317.
Benirschke, K. and Kaufmann, P. Pathology of the human placenta. New York, Springer-Verlag, 2000, 42-46, 116, 281-297.
Borie, E., et al. Platelet-rich fibrin application in dentistry: a literature review. Int J Clin Exp Med 2015;8(5):7922-7929.

Bourdoulous, S. et al., Fibronectin Matrix Regulates Activation of RHO and CDC42 GTPases and Cell Cycle Progression. J. Cell Biol. 143:267-276 (1998).
Bourne, GL, The microscopic anatomy of the human amnion and chorion. Am. J. Obstet. & Gynec. (1960) 79 (6):1070-1073.
Brem, H. and Tomic-Canic, M.,"Cellular and molecular basis of wound healing in diabetes," J. Clin. Invest. (2007) 117(5): 1219-1222.
Brooks, P. et al., Requirement of vascular integrin alpha v beta 3 for angiogenesis. Science, 264, 569-571 (1994).
Brown, B.N., et al.,Comparison of Three Methods for the Derivation of a Biologic Scaffold Composed of Adipose Tissue Extracellular Matrix. Tissue Eng. Part C., 17(4): 411-421 (2011).
Brown, E. Phagocytosis, Bioessays, 17:109-117 (1995).
Brown, L. et al., Expression of vascular permeability factor (vascular endothelial growth factor) by epidermal keratinocytes during wound healing. J Exp Med, 176, 1375-1379 (1992).
Bugge, T. et al., Loss of fibrinogen rescues mice from the pleiotropic effects of plasminogen deficiency. Cell, 87, 709-719 (1996).
Butler, DL., et al. Functional Tissue Engineering for Tendon Repair: A Multidisciplinary Strategy Using Mesenchymal Stem Cells, Bioscaffolds, and Mechanical Stimulation. J. Orthop. Res. 26:1-9, 2008. Published by Wiley Periodicals, Inc.
Butler, W.T., et al., Dentin Extracellular Matrix (ECM) Proteins: Comparison to Bone ECM and Contribution to Dynamics of Dentinogenesis. Connective Tissue Research, 44(S1): 171-178 (2003).
Carmeliet, P. and Collen, D. Role of Vascular Endothelial Growth Factor and Vascular Endothelial Growth Factor Receptors in Vascular Development. In: Claesson-Welsh L. (eds) Vascular Growth Factors and Angiogenesis. Current Topics in Microbiology and Immunology 237: 133-158 (1999).
Carsons, S. et al. Detection and quantitation of fibronectin in synovial fluid from patients with rheumatic disease. Arth. Rheum 24(10):1261-67 (1981).
Chandran, P. and Sivadas, A. Platelet-rich fibrin: Its role in periodontal regeneration. The Saudi Journal for Dental Research (2014) 5, 117-122.
Chen, H-L and Panchision, D.M., "Concise Review: Bone Morphogenetic Protein Pleiotropism in Neural Stem Cells and Their Derivatives—Alternate Pathways, Convergent Signals," Stem Cells (2007) 25: 63-68.
Cheng, NC et al., Chondrogenic Differentiation of Adipose-Derived Adult Stem Cells by a Porous Scaffold Derived from Native Articular Cartilage Extracellular Matri. Tissue Eng. A, 15(2): 231-241 (2009).
Choi, J.S,et al., Fabrication of Porous Extracellular Matrix Scaffolds from Human Adipose Tissue. Tissue Eng. Part C., 16(3): 387-396 (2010).
Chu, Tien-Min G. et al, Chapter 11—Craniofacial Biology, Orthodontics, and Implants, in Basic and Applied Bone Biology (2014) pp. 225-242.
Chung, CY et al., Binding of Tenascin-C to Soluble Fibronectin and Matrix Fibrils. J. Biol. Chem. 270:29012-29017 (1995).
Clark R. et al., Fibronectin and Fibrin Provide a Provisional Matrix for Epidermal Cell Migration During Wound Reepithelialization. J. Invest Dermatol, 79, pp. 264-269 (1982).
Clark, R. et al., Collagen matrices attenuate the collagen-synthetic response of cultured fibroblasts to TGF-beta. J Cell Sci, 108, pp. 1251-1261).
Clark, R. et al., Fibronectin is produced by blood vessels in response to injury. J. Exp Med, 156, 646-651 (1982).
Clark, R. et al., Platelet isoforms of platelet-derived growth factor stimulate fibroblasts to contract collagen matrices. J Clin Invest, 84, 1036-1040 (1989).
Clark, R., Fibronectin Matrix Deposition and Fibronectin Receptor Expression in Healing and Normal Skin. J Invest Dermatol, 94, Suppl, pp. 128S-134S (1990).
Clark, RA et al., Fibronectin deposition in delayed-type hypersensitivity. Reactions of normals and a patient with afibrinogenemia.. J. Clin. Invest. 74:1011-16 (1984).
Clark, RA et al., Fibronectin in delayed-type hypersensitivity skin reactions: associations with vessel permeability and endothelial cell activation.. J. Immunol. 126(2):787-93 (1981).

(56) References Cited

OTHER PUBLICATIONS

Clark, RAF et al., Blood Vessel Fibronectin Increases in Conjunction with Endothelial Cell Proliferation and Capillary Ingrowth During Wound Healing. J. Invest. Derm. 79:269-76 (1982).
Correa Do Amaral, RJF, et al., Platelet-Rich Plasma Obtained with Different Anticoagulants and Their Effect on Platelet Numbers and Mesenchymal Stromal Cells Behavior In Vitro. Stem Cells Int., Article ID 7414036, 11 pages (2016).
Cunningham, F. et al., The placenta and fetal membranes, Williams Obstetrics, 20th ed. Appleton and Lange, 1997, 95-125.
Cursiefen, C., et al., Inhibition of Hemangiogenesis and Lymphangiogenesis after Normal-Risk Corneal Transplantation by Neutralizing VEGF Promotes Graft Survival Invest Ophthalmol Vis Sci. 45; 2666-73 (2004).
Cursiefen, C., et al., VEGF-A stimulates lymphangiogenesis and hemangiogenesis in inflammatory neovascularization via macrophage recruitment. J. Clin Invest. 113: 1040-50 (2004).
Dang, P., et al. Virtual Surgery Planning and Three-Dimensional Printing Template to Customize Bone Graft Toward Implant Insertion. Journal of Craniofacial Surgery: Mar. 2017—vol. 28—Issue 2—e173-e175; doi: 10.1097/SCS.0000000000003386.
Desmouliere, A. and Gabbiani, G. The role of the myofibroblast in wound healing and fibrocontractive diseases. In Clark, R. Ed. The molecular and cellular biology of wound repair. 2nd Ed. New York, Plenum Press, pp. 391-423 (1996).
Dimmeler, S., et al., Phosphorylation of the endothelial nitric oxide synthase at Ser-1177 is required for VEGF-induced endothelial cell migration FEBS Lett 477:258-262 (2000).
Dinarello, CA., The interleukin-1 family: 10 years of discovery. FASEB J., 8(15):1314-3225 (1994).
Dohan, David M. et al., Platelet-rich fibrin (PRF): a second-generation platelet concentrate. Part I: Technological concepts and evolution, Oral Surg Oral Med Oral Pathol Oral Radiol Ended 2006; 101:E37-44.
Rappolee, D. et al., Wound macrophages express TGF-alpha and other growth factors in vivo: analysis by mRNA phenotyping. Science, 241, pp. 708-712 (1988).
Repesh, LA. et al. Fibronectin involvement in granulation tissue and wound healing in rabbits. J. Histochem. Cytochem. 30(4):351-58 (1982).
Riches, D., In Clark R., Ed. The molecular and cellular biology of wound repair, 2nd Ed. New York, Plenum Press, pp. 95-141.
Roberts, A. and Sporn, M, Transforming Growth Factor-1, In Clark, R. ed. The molecular and cellular biology of wound repair. 2nd Ed. New York, Plenum Press, pp. 275-308 (1996).
Robinson, GS, et al., Oligodeoxynucleotides inhibit retinal neovascularization in a murine model of proliferative retinopathy. Proc. Natl Acad Sci USA 93; 4851-56 (1996).
Robson MC et al., Wound healing: Biologic features and approaches to maximize healing trajectories. Curr Probl Surg 2001; 38: 72-140.
Robson, M. et al., Platelet-derived growth factor BB for the treatment of chronic pressure ulcers. Lancet, 339, pp. 23-25 (1992).
Robson, M. et al., The safety and effect of topically applied recombinant basic fibroblast growth factor on the healing of chronic pressure sores. Ann Surg, 216, pp. 401-406 (1992).
Sabatier L. et al., Fibrillin Assembly Requires Fibronectin. Mol. Biol. Cell 20(3):846-858 (2009).
Sato, Y et al, Properties of Two VEGF Receptors, Flt-1 and KDR, in Signal Transduction. Ann NY Acad Sci. 902:201-7 (2000).
Sawkins, MJ et al., 3D Cell and Scaffold Patterning Strategies in Tissue Engineering. Recent Pat. Biomed. Eng. 6:3-21 (2013).
Schiro, J. et al., Integrin alpha 2 beta 1 (VLA-2) mediates reorganization and contraction of collagen matrices by human cells. Cell, 67, 403-410 (1991).
Sephel, G.C. and Woodward, S.C., 3. Repair, Regeneration and Fibrosis, in Rubin's Pathology, Rubin, R. and Strayer, D.S. Eds; 5th Ed., Wolters Kluwer Health, /Lippincott Williams & Wilkins, Philadelphia, PA (2008).

Shen, WY et al., Preclinical Evaluation of a Phosphorothioate Oligonucleotide in the Retina of Rhesus Monkey. Lab Invest 82:167-82 (2002).
Shi S. and Gronthos S. Perivascular Niche of Postnatal Mesenchymal Stem Cells in Human Bone Marrow and Dental Pulp. Journal of Bone and Mineral Research 18(4): 696-704 (2003).
Sims, JE., et al., A new nomenclature for IL-1-family genes. Trends Immunol., 22(10): 536-537 (2001).
Singer AF and Clark RA, Cutaneous Wound Healing. N Engl J Med Sep. 2, 1999; 341(10): 738-746.
Smidsrod, O. et al., Alginate as immobilization matrix for cells. TIBTECH 8:71-78 (1990).
Smiler, DG et al., Sinus lift grafts and endosseous implants. Treatment of the atrophic posterior maxilla. Dental Clinics of North America (1992) 36(1): 151-188.
Sottile, J. et al., Fibronectin matrix assembly enhances adhesion-dependent cell growth. J. Cell Sci. 111:2933-2943 (1998).
Sottile, J. et al., Fibronectin Polymerization Regulates the Composition and Stability of Extracellular Matrix Fibrils and Cell-Matrix Adhesions. Mol. Biol. Cell 13:3546-3559 (2002).
Sottile, J. et al., Fibronectin polymerization stimulates cell growth by RGD-dependent and-independent mechanisms J. Cell Sci. 113:4287-4299 (2000).
Stacker, SA, et al., A Mutant Form of Vascular Endothelial Growth Factor (VEGF) That Lacks VEGF Receptor-2 Activation Retains the Ability to Induce Vascular Permeability. J. Biol. Chem. vol. 274:34884-34892 (1999).
Steed, D., Clinical evaluation of recombinant human platelet—derived growth factor for the treatment of lower extremity diabetic ulcers. J Vasc Surg, 21, pp. 71-78 (1995).
Sullivan, L.A. and Brekken, R.A. The VEGF family in cancer and antibody-based strategies for their inhibition. MAbs. 2(2):165-75, Mar. 2010.
Sundararaghavan, V. et al., "Diabetes and bone health: latest evidence and clinical implications", Ther. Adv. Muscloskeletal Dis. (2017) 9(3): 67-74.
Thakker, G.D., et al., The Role of Phosphatidylinositol 3-Kinase in Vascular Endothelial Growth Factor Signaling. J. Biol. Chem. 274; 10002-7 (1999).
Torikata, C. et al., Ultrastructural distribution of fibronectin in normal and fibrotic human lung.. Lab. Invest. 52(4):399-408 (1985).
Ueno, H., et al., Inhibition of PDGF beta receptor signal transduction by coexpression of a truncated receptor. Science. May 10, 1991; 252(5007):844-8.
Ulmer, FL et al., Stem cells-prospects in dentistry. Schweiz Monatsschr Zahnmed, 120:860-872 (2010).
Uriel, S et al., The role of adipose protein derived hydrogels in adipogenesis. Biomaterials, 29: 3712-3719 (2008).
Vaalamo, M. et al., Distinct Populations of Stromal Cells Express Collagenase-3 (MMP-13) and Collagenase-1 (MMP-1) in Chronic Ulcers but Not in Normally Healing Wounds. J Invest Dermatol, 109, pp. 96-101 (1997).
Vaina, C., et al., Epidermal Growth Factor: Layered Silicate Nanocomposites for Tissue Regeneration. Biomacromolecules 2011, 12: 3139-3146.
Velling, T. et al., Polymerization of type I and III collagens is dependent on fibronectin and enhanced by integrins alpha 11beta1 and alpha 2beta 1. J. Biol. Chem. 277(40):37377-37381 (2002).
Velnar T et al., The Wound Healing Process: an Overview of the Cellular and Molecular Mechanisms. The Journal of International Medical Research 2009; 37: 1528-1542.
Wang, HL and Avila, G. Platelet Rich Plasma: Myth or Reality?. European Journal of Dentistry. vol. 1, 192-194, Oct. 2007.
Wang, W. and Yeung, K.W.K., Bone grafts and biomaterials substitutes for bone defect repair: a review. Bioactive Materials 2 (2017): 224-47.
Welch, M. et al., Temporal relationships of F-actin bundle formation, collagen and fibronectin matrix assembly, and fibronectin receptor expression to wound contraction.. J. Cell Biol, 110, pp. 133-145 (1990).
Wenger, RH and Gassman, M., Oxygen (es) and the hypoxia-inducible factor-1. Biol. Chem. 378:609-616 (1997).

(56) References Cited

OTHER PUBLICATIONS

Wenstrup, RJ et al., Type V Collagen Controls the Initiation of Collagen Fibril Assembly. J. Biol. Chem. 279: 53331-53337 (2004).
Werner, S. et al., The function of KGF in morphogenesis of epithelium and reepithelialization of wounds. Science, 266, pp. 819-822 (1994).
Weyrich AS and Zimmerman GA, Platelets: signaling cells in the immune continuum. Trends Immunol Sep. 2004;25(9): 489-495.
Wong, WKR., et al., Applications, and Efficient Large-Scale Production, of Recombinant Human Epidermal Growth Factor Biotechnol. Genet. Eng. Rev. 2001, 18: 51-71.
Woodley, D. et al., Collagen telopeptides (cross-linking sites) play a role in collagen gel lattice contraction. J Invest Dermatol, 97, 580-585 (1991).
Wysocki, AB and Grinnell, F., Fibronectin profiles in normal and chronic wound fluid. Lab Invest. (1990) 63(6);825-31.
Xu, J. and Clark, R., Extracellular matrix alters PDGF regulation of fibroblast integrins.. J Cell Biol, 132, pp. 239-249 (1996).
Yuan, F.,et al., Time-dependent vascular regression and permeability changes in established human tumor xenografts induced by an anti-vascular endothelial growth factoryvascular permeability factor antibody. Proc. Natl. Acad, Sci, USA. 93:14765-70 (1996).
Zannettino ACW, et al. Human Mulipotential Stromal Stem Cells are Derived from a Discrete Subpopulation of STRO-1 bright/CD34-/CD45-/Glycophorin-A-Bone Marrow Cells. Haematologica 92 1707-1708 (2007).
Zannettino ACW,et al Multipotential human adipose-derived stromal stem cells exhibit a perivascular phenotype in vitro and in vivo. Journal of Cellular Physiology 214(2):413-421 (2008).
Zhang, X., et al., 2005, Periosteal stem cells are essential for bone revitalization and repair. J. Musculoskelet. Neuronal. Interact. 5(4): 360-362.
Dohan, DM et al., Classification of platelet concentrates: from pure platelet-rich plasma (P-PRP) to leucocyte- and platelet-rich fibrin (L-PRF) Trends Biotechnol. 27:158-67 (2009).
Duan, DSR., et al., A Functional Soluble Extracellular Region of the Platelet-derived Growth Factor (PDGF) beta-Receptor Antagonizes PDGF-stimulated Responses. J Biol Chem. Jan. 5, 1991; 266(1):413-8 (1991).
Dunn, E., et al., Annotating genes with potential roles in the immune system: six new members of the IL-1 family. Trends Immunol., 22(10): 533-536 (2001).
Dvorak, H.F., et al. Vascular Permeability Factor/Vascular Endothelial Growth Factor and the Significance of Microvascular Hyperpermeability in Angiogenesis. In: Claesson-Welsh L. (eds) Vascular Growth Factors and Angiogenesis. Current Topics in Microbiology and Immunology, vol. 237; pp. 97-132. Springer, Berlin, Heidelberg (1999).
Ferguson, C. e al, Does adult fracture repair recapitulate embryonic skeletal formation? Mech. Dev. (1999) 87: 57.
Flynn, F. and Woodhouse, K.A., Adipose tissue engineering with cells in engineered matrices. Organogenesis, 4(4): 228-235 (2008).
Flynn, L.E. The use of decellularized adipose tissue to provide an inductive microenvironment for the adipogenic differentiation of human adipose-derived stem cells. Biomaterials, 31: 4715-4724 (2010).
Folkman, J. and D'Amore, P, Blood Vessel Formation: What Is Its Molecular Basis?. Cell, 87, pp. 1153-1155 (1996).
Folkman, J., Angiogenesis and angiogenesis inhibition: an overview, EXS, 79, 1-8, (1997).
Fong, H.K., et al., The Crowning Achievement: Getting to the Root of the Problem. J. Dent. Educ., 69(5): 555-570 (2005).
Gabbiani, G. et al., Cytoplasmic filaments and gap junctions in epithelial cells and myofibroblasts during wound healing. J Cell Biol, 76, pp. 561-568 (1978).
Girdler, NM et al., The effect of epidermal growth factor mouthwash on cytotoxic-induced oral ulceration. A phase I clinical trial.. Am. J. Clin. Oncol. 1995, 18: 403-406.

Glazer, A.N., et al., Chemical Modification of Proteins, Selected Methods and Analytical Procedures, Chapter 2, pp. 13-67, Elsevier Biomedical Press, New York (1975).
Goliger, J. and Paul, D. Wounding alters epidermal connexin expression and gap junction-mediated intercellular communication. Mol Biol Cell, 6, pp. 1491-1501 (1995).
Gray, A. et al., A and B chains of fibrinogen stimulate proliferation of human fibroblasts. J Cell Sci, 104, pp. 409-413 (1993).
Greiling, D. and Clark R., Fibronectin provides a conduit for fibroblast transmigration from collagenous stroma into fibrin clot provisional matrix. J. Cell Sci, 110, pp. 861-870 (1997).
Grinnell, F. et al. Distribution of Fibronectin During Wound Healing in Vivo. J. Invest. Derm. 76:181-189 (1981).
Grinnell, F. Fibronectin and wound healing. J Cell Biochem. (1984) 26(2):107-16.
Gronthos S.,et al.,Molecular and cellular characterisation of highly purified human bone marrow stromal stem cells. Journal of Cell Science 116: 1827-1835 (2003).
Gronthos, S et.al., Surface protein characterization of human adipose tissue-derived stromal cells. J. Cell. Physiol., 189: 54-63 (2001).
Gui, L. et al. Identification of the heparin-binding determinants within fibronectin repeat III1: Role in cell spreading and growth. J. Biol. Chem. 281(46):34816-34825 (2006).
Gulabivala, K., NG, YL, Tooth organogenesis, morphology and physiology., Endodontics (4th Edition), Mosby (2014), pp. 2-32.
Gupta, V. et al., Regenerative potential of platelet rich fibrin in dentistry: literature review. AJOHAS (2011) 1 (1):22-28.
Haedo, W. et al., Oral human recombinant epidermal growth factor in the treatment of patients with duodenal ulcer. Rev. Esp. Enferm. Dig. 1996, 88: 409-418.
Haley, KM et al, Neonatal platelets: mediators of primary hemostasis in the developing hemostatic system. Pediatr. Res. 2014; 76(3): 230-37.
Hammerle, CH et al, "Biology of soft tissue wound-healing and regeneration—consensus report of Group 1of the 10th European workshop on Periodontology," J. Clin. Periodontol. (2014) Suppl. 15: S1-5.
Hasegawa, N. and Yamamoto, K., Epidermal growth factor suppresses in vitro senescence in the ability of human umbilical vein endothelial cells to proliferate, but not in the ability to produce prostacyclin. Mech. Ageing. Dev. 1992, 66:107-114.
Heidaran, MA., et al., Beta PDGFR-IgG chimera demonstrates that human beta PDGFR Ig-like domains 1 to 3 are sufficient for high affinity PDGF BB binding.. FASEB J. Jan. 1995; 9(1):140-5.
Heldin, C. and Westermark B., In: Clark R., ed. The molecular and cellular biology of wound repair, 2nd Ed. New York, Plenum Press, pp. 249-273, (1996).
Hocking, DC et al., Fibronectin matrix polymerization regulates small airway epithelial cell migration. Am. J. Physiol. Lung Cell Mol. Physiol. 285:L169-L179 (2003).
Hocking, DC et al., Inhibition of Fibronectin Matrix Assembly by the Heparin-binding Domain of Vitronectin. J. Biol. Chem. 274:27257-27264 (1999).
Hocking, DC et al., Stimulation of Integrin-mediated Cell Contractility by Fibronectin Polymerization. J. Biol. Chem. 275:10673-10682 (2000).
Hollinger, J., Wong, ME, "The integrated processes of hard tissue regeneration with special emphasis on fracture healing," Oral Surg. Oral Med. Oral Pathol. Oral Radiol. Endod. (1996) 82: 594-606.
Honda, M., et al.,Experimental subretinal neovascularization is inhibited by adenovirus-mediated soluble VEGF/flt-1 receptor gene transfection: a role of VEGF and possible treatment for SRN in age-related macular degeneration. Gene Ther. 7:978-75 (2000).
Hudson, LG and McCawley, LJ., Contributions of the epidermal growth factor receptor to keratinocyte motility. Microsc. Res. Tech. 1998, 43: 444-455.
Huising, MO., et al., The molecular evolution of the interleukin-1 family of cytokines; IL-18 in teleost fish. Dev. Comp. Immunol., 28(5):395-413 (2004).
Hynes, RO et al., Fibronectins: multifunctional modular glycoproteins. J. Cell Biol. 95:369-377 (1982).

(56) References Cited

OTHER PUBLICATIONS

Ilan, N. et al., Distinct signal transduction pathways are utilized during the tube formation and survival phases of in vitro angiogenesis. J Cell Sci, 111, 3621-3631 (1998).

Jahan-Parwar, M.D., BABAK, Facial Bone Anatomy, https://emedicine.medscape.com/article/835401-overview#a2, visited Jun. 20, 2018.

Jayson, GC and Hasan, J., VEGF antagonists, Expert Opinion on Biological Therapy, 1:4, 703-718 (2001) DOI: 10.1517/14712598. 1.4.703.

Kanno, S. et al., Roles of two VEGF receptors, Flt-1 and KDR, in the signal transduction of VEGF e€ects in human vascular endothelial cells. Oncogene 19: 2138-46 (2000).

Kendall, RL et al, Identification of a Natural Soluble Form of the Vascular Endothelial Growth Factor Receptor, FLT-1, and Its Heterodimerization with KDR. Biochem Biophy Res Comm. 226:324-28 (1996).

Kim, H-J, et al., "Cortical and cancellous bone thickness on the anterior region of alveolar bone in Korean: a study of dentate human cadavers," J. Adv. Prosthodont. (2012) 4(3): 146-52.

Kim, K.J et al., Inhibition of vascular endothelial growth factor-induced angiogenesis suppresses tumour growth in vivo. Nature 362; 841-44 (1993).

Kinnaird, T., et al., Local Delivery of Marrow-Derived Stromal Cells Augments Collateral Perfusion Through Paracrine Mechanisms. Circulation 109:1543-49 (2004).

Koivisto, L. et al., HaCaT keratinocyte migration is dependent on epidermal growth factor receptor signaling and glycogen synthase kinase-3alpha. Exp. Cell Res. 2006, 312: 2791-2805.

Kumar, P., et al. Bone Grafts in Dentistry. J. Pharm. Bioallied Sci., Jun. 2013, 5(Suppl 1): S125-127.

Lanza, R., et al., Ed., Principles of Tissue Engineering, 4th Ed. Academic Press, Waltham, MA (2014) at 1204.

Lanza, Robert, et al. Eds, Principles of Tissue Engineering, 4th Ed., Elsevier, Inc.: New York, 2014 at 1047-1048.

Leibovich, S, and Ross, R., The role of the macrophage in wound repair. A study with hydrocortisone and antimacrophage serum. Am J Pathol, 78, pp. 1-100 (1975).

Jarlwala, SH, etal. 3D Printing of Personalized Artificial Bone Scaffolds. 3D Print Addit. Manuf. Jun. 1, 2015; 2(2):56-64.

Zhou, X. et al., Fibronectin fibrillogenesis regulates three-dimensional neovessel formation. Genes. Dev. 22(9): 1231-1243 (2008).

Asa'Ad Farah et al., "3D-Printed Scaffolds and Biomaterials: Review of Alveolar Bone Augmentation and Periodontal Regeneration Applications", International Journal of Dentistry, vol. 2016, Jun. 5, 2016.

Babo Pedro S. et al., "The Role of a Platelet Lysate-Based Compartmentalized System as a Carrier of Cells and Platelet-Origin Cytokines for Periodontal Tissue Regeneration", Tissue Engineering Part A, vol. 22, No. 19-20, Oct. 1, 2016.

Han Fengxuan et al., "A pilot study of conically graded chitosanÂ-gelatin hydrogel/PLGA scaffold with dual-delivery of TGF-[beta]1 and BMP-2 for regeneration of cartilage-bone interface: Conically Graded Scaffold of Hydrogel/PLGA", Journal of Biomedical Materials Research Part B: Applied Biomaterials, vol. 103, No. 7, Nov. 11, 2014.

Kamal Mohammad et al., "Bone regeneration using composite nonÂ-demineralized xenogenic dentin with beta-tricalcium phosphate in experimental alveolar cleft repair in a rabbit model", Journal of Translational Medicine, vol. 15, No. 1, Dec. 23, 2017.

Park Ch et al., "Biomimetic hybrid scaffolds for engineering human tooth-ligament interfaces", Biomaterials, Elsevier, Amsterdam, NL, vol. 31, No. 23, Aug. 1, 2010.

Supplementary European Search Report, EP Appl. No. 19861640.1, (Rejuvablast LLC) dated Apr. 4, 2022, 13 pages.

Varoni E.M et al., "Chitosan-Based Trilayer Scaffold for Multitissue Periodontal Regeneration", Journal of Dental Research, vol. 97, No. 3, Mar. 1, 2018.

Zhou Shuai et al., "Efficacy of Adjunctive Bioactive Materials in the Treatment of Periodontal Intrabony Defects: A Systematic Review and Meta-Analysis", Biomed Research International, vol. 2018, May 27, 2018.

\* cited by examiner

COMBINATION GRAFTS FOR TISSUE REPAIR OR REGENERATION APPLICATIONS

CROSS-REFERENCE TO THE RELATED APPLICATIONS

This application claims the benefit of priority to U.S. Provisional Application No. 62/732,213, filed on Sep. 17, 2018, the entire contents of which are incorporated herein.

FIELD OF THE INVENTION

The present disclosure relates to hard and soft tissue grafts, and combinations thereof, comprising a three-dimensional carrier matrix, a growth factor composition, and a cell culture composition.

BACKGROUND OF THE INVENTION

I Biology of Wound Healing

A wound results from damage or disruption to normal anatomical structure and function (Robson M C et al., Curr Probl Surg 2001; 38: 72-140; Velnar T et al., The Journal of International Medical Research 2009; 37: 1528-1542). This can range from a simple break in the epithelial integrity of the skin to deeper, subcutaneous tissue with damage to other structures such as tendons, muscles, vessels, nerves, parenchymal organs and even bone (Alonso J E et al., Surg Clin North Am 1996; 76: 879-903). Irrespective of the cause and form, wounding damages and disrupts the local tissue environment.

Wound healing is a dynamic, interactive process involving soluble mediators, blood cells, extracellular matrix, and parenchymal cells. The wound repair process can be divided into four (4) temporally and spatially overlapping phases: (1) a coagulation phase; (2) an inflammatory phase, (3) a proliferative phase, and (4) a remodeling phase. Much of what is known is based on wound healing of human skin.

Coagulation Phase

Immediately after injury, platelets adhere to damaged blood vessels, initiate a release reaction, and begin a hemostatic reaction, giving rise to a blood-clotting cascade that prevents excessive bleeding and provides provisional protection for the wounded area. Blood platelets release well over a dozen growth factors, cytokines, and other survival or apoptosis-inducing agents (Weyrich A S and Zimmerman G A, Trends Immunol 2004 September; 25(9): 489-495). Key components of the platelet release reaction include platelet-derived growth factor (PDGF) and transforming growth factors AI and 2 (TGF-A1 and TGF-2), which attract inflammatory cells, such as leukocytes, neutrophils, and macrophages (Singer A F and Clark R A, N Engl J Med 1999 Sep. 2; 341(10): 738-746).

Inflammatory Phase

The inflammatory phase is triggered by capillary damage, which leads to the formation of a blood clot/provisional matrix composed of fibrin and fibronectin. This provisional matrix fills the tissue defect and enables effector cell influx. Platelets present in the clot release multiple cytokines that participate in the recruitment of inflammatory cells (such as neutrophils, monocytes, and macrophages, amongst others), fibroblasts, and endothelial cells (ECs).

Proliferative Phase

The inflammatory phase is followed by a proliferative phase, in which active angiogenesis creates new capillaries, allowing nutrient delivery to the wound site, notably to support fibroblast proliferation. Fibroblasts present in granulation tissue are activated and acquire a smooth muscle cell-like phenotype, then being referred to as myofibroblasts. Myofibroblasts synthesize and deposit extracellular matrix (ECM) components that replace the provisional matrix. They also have contractile properties mediated by α-smooth muscle actin organized in microfilament bundles or stress fibers. Myofibroblastic differentiation of fibroblastic cells begins with the appearance of the protomyofibroblast, whose stress fibers contain only β- and γ-cytoplasmic actins. Protomyofibroblasts can evolve into differentiated myofibroblasts whose stress fibers contain α-smooth muscle actin.

Remodeling Phase

The fourth healing phase involves gradual remodeling of the granulation tissue and reepithelialization. This remodeling process is mediated largely by proteolytic enzymes, especially matrix metalloproteinases (MMPs) and their inhibitors (TIMPs, tissue inhibitors of metalloproteinases). During the reepithelialization, Type III collagen, the main component of granulation tissue, is replaced gradually by type I collagen, the main structural component of the dermis. Elastin, which contributes to skin elasticity and is absent from granulation tissue, also reappears. Cell density normalizes through apoptosis of vascular cells and myofibroblasts (resolution).

1.1 Inflammation

Tissue injury causes the disruption of blood vessels and extravasation of blood constituents. The blood clot re-establishes hemostasis and provides a provisional extracellular matrix for cell migration. Platelets not only facilitate the formation of a hemostatic plug but also secrete several mediators of wound healing, such as platelet-derived growth factor, which attract and activate macrophages and fibroblasts (Heldin, C. and Westermark B., In: Clark R., ed. The molecular and cellular biology of wound repair, 2nd Ed. New York, Plenum Press, pp. 249-273, (1996)). It was suggested, however, that, in the absence of hemorrhage, platelets are not essential to wound healing; numerous vasoactive mediators and chemotactic factors are generated by the coagulation and activated-complement pathways and by injured or activated parenchymal cells that were shown to recruit inflammatory leukocytes to the site of injury (Id.).

Ingress of cells into a wound and activation of local cells are initiated by mediators that are either released de novo by resident cells or from reserves stored in the granules of platelets and basophils. Sephel, G. C. and Woodward, S. C., 3. Repair, Regeneration and Fibrosis," in Rubin's Pathology, Rubin, R. and Strayer, D. S. Eds; 5th Ed., Wolters Kluwer Health, /Lippincott Williams & Wilkins, Philadelphia, Pa. (2008), at 71. Cell migration uses the response of cells to cytokines and insoluble substrates of the extracellular matrix. Id. At 72.

Infiltrating neutrophils cleanse the wounded area of foreign particles and bacteria and then are extruded with the eschar (a dead tissue that falls off (sheds) from healthy skin or is phagocytosed by macrophages). In response to specific chemoattractants, such as fragments of extracellular-matrix protein, transforming growth factor β (TGF-β), and monocyte chemoattractant protein-1 (MCP-1), monocytes also infiltrate the wound site and become activated macrophages that release growth factors (such as platelet-derived growth factor and vascular endothelial growth factor), which initiate the formation of granulation tissue. Macrophages bind to specific proteins of the extracellular matrix by their integrin receptors, an action that stimulates phagocytosis of microorganisms and fragments of extracellular matrix by the macrophages (Brown, E. Phagocytosis, Bioessays, 17:109-

117 (1995)). Studies have reported that adherence to the extracellular matrix also stimulates monocytes to undergo metamorphosis into inflammatory or reparative macrophages. These macrophages play an important role in the transition between inflammation and repair (Riches, D., In Clark R., Ed. The molecular and cellular biology of wound repair, 2nd Ed. New York, Plenum Press, pp. 95-141). For example, adherence induces monocytes and macrophages to express Colony-Stimulating Factor-1 (CSF-1), a cytokine necessary for the survival of monocytes and macrophages; Tumor Necrosis Factor-α (TNF-α), a potent inflammatory cytokine; and Platelet-Derived Growth Factor (PDGF), a potent chemoattractant and mitogen for fibroblasts. Other cytokines shown to be expressed by monocytes and macrophages include Transforming Growth Factor (TGF-α), Interleukin-1 (IL-1), Transforming Growth Factor β (TGF-β), and Insulin-like Growth Factor-I (IGF-I) (Rappolee, D. et al., Science, 241, pp. 708-712 (1988)). The monocyte- and macrophage-derived growth factors have been suggested to be necessary for the initiation and propagation of new tissue formation in wounds, because macrophage depleted animals have defective wound repair (Leibovich, S, and Ross, R., Am J Pathol, 78, pp 1-100 (1975)).

1.2 Epithelialization

Reepithelialization of wounds begins within hours after injury. Epidermal cells from skin appendages, such as hair follicles, quickly remove clotted blood and damaged stroma from the wound space. At the same time, the cells undergo phenotypic alteration that includes retraction of intracellular tonofilaments (Paladini, R. et al., J. Cell Biol, 132, pp. 381-397 (1996)); dissolution of most inter-cellular desmosomes, which provide physical connections between the cells; and formation of peripheral cytoplasmic actin filaments, which allow cell movement and migration (Goliger, J. and Paul, D. Mol Biol Cell, 6, pp. 1491-1501 (1995); Gabbiani, G. et al., J Cell Biol, 76, PP. 561-568 (1978)). Furthermore, epidermal and dermal cells no longer adhere to one another, because of the dissolution of hemidesmosomal links between the epidermis and the basement membrane, which allows the lateral movement of epidermal cells. The expression of integrin receptors on epidermal cells allows them to interact with a variety of extracellular-matrix proteins (e.g., fibronectin and vitronectin) that are interspersed with stromal type I collagen at the margin of the wound and interwoven with the fibrin clot in the wound space (Clark, R., J Invest Dermatol, 94, Suppl, pp. 128S-134S (1990)). The migrating epidermal cells dissect the wound, separating desiccated eschar (a dead tissue that falls off (sheds) from healthy skin) from viable tissue. The path of dissection appears to be determined by the array of integrins that the migrating epidermal cells express on their cell membranes.

The degradation of the extracellular matrix, which is required if the epidermal cells are to migrate between the collagenous dermis and the fibrin eschar, depends on the production of collagenase by epidermal cells (Pilcher, B. et al., J Cell Biol, 137, pp. 1445-1457 (1997)), as well as the activation of plasmin by plasminogen activator produced by the epidermal cells (Bugge, T. et al., Cell, 87, 709-719 (1996)). Plasminogen activator also activates collagenase (matrix metalloproteinase-1) (Mignatti, P. et al., Proteinases and Tissue Remodeling. In Clark, R. Ed. The molecular and cellular biology of wound repair. 2nd Ed. New York, Plenum Press, 427-474 (1996)) and facilitates the degradation of collagen and extracellular-matrix proteins.

One to two days after injury, epidermal cells at the wound margin begin to proliferate behind the actively migrating cells. The stimuli for the migration and proliferation of epidermal cells during reepithelialization have not been determined, but several possibilities have been suggested. The absence of neighbor cells at the margin of the wound (the "free edge" effect) may signal both migration and proliferation of epidermal cells. Local release of growth factors and increased expression of growth-factor receptors may also stimulate these processes. Leading contenders include Epidermal Growth Factor (EGF), Transforming Growth Factor-α (TGF-α), and Keratinocyte Growth Factor (KGF) (Nanney, L. and King, L. Epidermal Growth Factor and Transforming Growth Factor-α. In Clark, R. Ed. The molecular and cellular biology of wound repair. 2nd Ed. New York, Plenum Press, pp. 171-194 (1996); Werner, S. et al., Science, 266, pp. 819-822 (1994); Abraham, J. and Klagsburn, M. Modulation of Wound Repair by Members of the Fibroblast Growth Factor family. In Clark, R. Ed. The molecular and cellular biology of wound repair. 2nd Ed. New York, Plenum Press, pp. 195-248 (1996)). As re-epithelialization ensues, basement-membrane proteins reappear in a very ordered sequence from the margin of the wound inward, in a zipper-like fashion (Clark R. et al., J. Invest Dermatol, 79, pp. 264-269 (1982)). Epidermal cells revert to their normal phenotype, once again firmly attaching to the reestablished basement membrane and underlying dermis.

1.3 Formation of Granulation Tissue

New stroma, often called granulation tissue, begins to invade the wound space approximately four days after injury. Numerous new capillaries endow the new stroma with its granular appearance. Macrophages, fibroblasts, and blood vessels move into the wound space at the same time (Hunt, T. ed. Wound Healing and Wound Infection: Theory and Surgical Practice. New York, Appleton-Century-Crofts (1980)). The macrophages provide a continuing source of growth factors necessary to stimulate fibroplasia and angiogenesis; the fibroblasts produce the new extracellular matrix necessary to support cell ingrowth; and blood vessels carry oxygen and nutrients necessary to sustain cell metabolism.

Growth factors, especially Platelet-Derived Growth Factor-4 (PDGF-4) and Transforming Growth Factor β-1 (TGF-β1) (Roberts, A. and Sporn, M, Transforming Growth Factor-1, In Clark, R. ed. The molecular and cellular biology of wound repair. 2nd Ed. New York, Plenum Press, pp. 275-308 (1996)) in concert with the extracellular-matrix molecules (Gray, A. et al., J Cell Sci, 104, pp. 409-413 (1993); Xu, J. and Clark, R., J Cell Biol, 132, pp. 239-149 (1996)), were shown to stimulate fibroblasts of the tissue around the wound to proliferate, express appropriate integrin receptors, and migrate into the wound space. It was reported that platelet-derived growth factor accelerates the healing of chronic pressure sores (Robson, M. et al., Lancet, 339, pp. 23-25 (1992) and diabetic ulcers (Steed, D., J Vasc Surg, 21, pp. 71-78 (1995)). In some other cases, basic Fibroblast Growth Factor (bFGF) was effective for treating chronic pressure sores (Robson, M. et al., Ann Surg, 216, pp. 401-406 (1992).

The structural molecules of newly formed extracellular matrix, termed the provisional matrix (Clark, R. et al., J. Invest Dermatol, 79, pp. 264-269, 1982), contribute to the formation of granulation tissue by providing a scaffold or conduit for cell migration. These molecules include fibrin, fibronectin, and hyaluronic acid (Greiling, D. and Clark R., J. Cell Sci, 110, pp. 861-870 (1997)). The appearance of fibronectin and the appropriate integrin receptors that bind fibronectin, fibrin, or both on fibroblasts was suggested to be the rate-limiting step in the formation of granulation tissue. While the fibroblasts are responsible for the synthesis, deposition, and remodeling of the extracellular matrix, the extracellular matrix itself can have a positive or negative effect on the ability of fibroblasts to perform these tasks, and to generally interact with their environment (Xu, J. and Clark, R., J Cell Sci, 132, pp. 239-249 (1996); Clark, R. et al., J Cell Sci, 108, pp. 1251-1261).

Cell movement into a blood clot of cross-linked fibrin or into tightly woven extracellular matrix requires an active proteolytic system that can cleave a path for cell migration. A variety of fibroblast-derived enzymes, in addition to serum-derived plasmin, are suggested to be potential candidates for this task, including plasminogen activator, collagenases, gelatinase A, and stromelysin (Mignatti, P. et al., Proteinases and Tissue Remodeling. In Clark, R. Ed. The molecular and cellular biology of wound repair. 2nd Ed. New York, Plenum Press, 427-474 (1996); Vaalamo, M. et al., J Invest Dermatol, 109, pp. 96-101 (1997)). After migrating into wounds, fibroblasts commence the synthesis of extracellular matrix. The provisional extracellular matrix is replaced gradually with a collagenous matrix, perhaps in response to Transforming Growth Factor-β1 (TGF-β1) signaling (Clark, R. et al., J Cell Sci, 108, pp. 1251-1261 (1995); Welch, M. et al., J. Cell Biol, 110, pp. 133-145 (1990))

Once an abundant collagen matrix has been deposited in the wound, the fibroblasts stop producing collagen, and the fibroblast-rich granulation tissue is replaced by a relatively acellular scar. Cells in the wound undergo apoptosis triggered by unknown signals. It was reported that dysregulation of these processes occurs in fibrotic disorders, such as keloid formation, hypertrophic scars, morphea, and scleroderma.

1.4 Neovascularization

The formation of new blood vessels (neovascularization) is necessary to sustain the newly formed granulation tissue. Angiogenesis is a complex process that relies on extracellular matrix in the wound bed as well as migration and mitogenic stimulation of endothelial cells (Madri, J. et al., Angiogenesis in Clark, R. Ed. The molecular and cellular biology of wound repair. 2nd Ed. New York, Plenum Press, pp. 355-371 (1996)). The induction of angiogenesis was initially attributed to acidic or basic Fibroblast Growth Factor. Subsequently, many other molecules have also been found to have angiogenic activity, including vascular endothelial growth factor (VEGF), Transforming Growth Factor-β (TGF-β), angiogenin, angiotropin, angiopoietin-1, and thrombospondin (Folkman, J. and D'Amore, P, Cell, 87, pp. 1153-1155 (1996)).

Low oxygen tension and elevated lactic acid were suggested also to stimulate angiogenesis. These molecules induce angiogenesis by stimulating the production of basic Fibroblast Growth Factor (FGF) and Vascular Endothelial Growth Factor (VEGF) by macrophages and endothelial cells. For example, it was reported that activated epidermal cells of the wound secrete large quantities of Vascular Endothelial cell Growth Factor (VEGF) (Brown, L. et al., J Exp Med, 176, 1375-1379 (1992)).

Basic fibroblast growth factor was hypothesized to set the stage for angiogenesis during the first three days of wound repair, whereas vascular endothelial-cell growth factor is critical for angiogenesis during the formation of granulation tissue on days 4 through 7 (Nissen, N. et al., Am J Pathol, 152, 1445-1552 (1998)).

In addition to angiogenesis factors, it was shown that appropriate extracellular matrix and endothelial receptors for the provisional matrix are necessary for angiogenesis. Proliferating microvascular endothelial cells adjacent to and within wounds transiently deposit increased amounts of fibronectin within the vessel wall (Clark, R. et al., J. Exp Med, 156, 646-651 (1982)). Since angiogenesis requires the expression of functional fibronectin receptors by endothelial cells (Brooks, P. et al., Science, 264, 569-571 (1994)), it was suggested that perivascular fibronectin acts as a conduit for the movement of endothelial cells into the wound. In addition, protease expression and activity were shown to also be necessary for angiogenesis (Pintucci, G. et al., Semin Thromb Hemost, 22, 517-524 (1996)).

The series of events leading to angiogenesis has been proposed as follows. Injury causes destruction of tissue and hypoxia. Angiogenesis factors, such as acidic and basic Fibroblast Growth Factor (FGF), are released immediately from macrophages after cell disruption, and the production of vascular endothelial-cell growth factor by epidermal cells is stimulated by hypoxia. Proteolytic enzymes released into the connective tissue degrade extracellular-matrix proteins. Fragments of these proteins recruit peripheral-blood monocytes to the site of injury, where they become activated macrophages and release angiogenesis factors. Certain macrophage angiogenesis factors, such as basic fibroblast growth factor (bFGF), stimulate endothelial cells to release plasminogen activator and procollagenase. Plasminogen activator converts plasminogen to plasmin and procollagenase to active collagenase, and in concert these two proteases digest basement membranes. The fragmentation of the basement membrane allows endothelial cells stimulated by angiogenesis factors to migrate and form new blood vessels at the injured site. Once the wound is filled with new granulation tissue, angiogenesis ceases and many of the new blood vessels disintegrate as a result of apoptosis (Ilan, N. et al., J Cell Sci, 111, 3621-3631 (1998)). This programmed cell death has been suggested to be regulated by a variety of matrix molecules, such as thrombospondins 1 and 2, and anti-angiogenesis factors, such as angiostatin, endostatin, and angiopoietin 2 (Folkman, J., Angiogenesis and angiogenesis inhibition: an overview, EXS, 79, 1-8, (1997)).

1.5 Wound Contraction and Extracellular Matrix Reorganization

Wound contraction involves a complex and orchestrated interaction of cells, extracellular matrix, and cytokines During the second week of healing, fibroblasts assume a myofibroblast phenotype characterized by large bundles of actin-containing microfilaments disposed along the cytoplasmic face of the plasma membrane of the cells and by cell-cell and cell-matrix linkages (Welch, M. et al., J Cell Biol, 110, 133-145 (1990); Desmouliere, A. and Gabbiani, G. The role of the myofibroblast in wound healing and fibrocontractive diseases. In Clark, R. Ed. The molecular and cellular biology of wound repair. 2nd Ed. New York, Plenum Press, pp. 391-423 (1996)). The appearance of the myofibroblasts corresponds to the commencement of connective-tissue compaction and the contraction of the wound. This contraction was suggested to require stimulation by Transforming Growth Factor (TGF)-β1 or β2 and Platelet-Derived Growth Factor (PDGF), attachment of fibroblasts to the collagen matrix through integrin receptors, and cross-links between individual bundles of collagen. (Montesano, R. and Orci, Proc Natl Acad Sci USA, 85, 4894-4897 (1988); Clark, R. et al., J Clin Invest, 84, 1036-1040 (1989); Schiro, J. et al., Cell, 67, 403-410 (1991); Woodley, D. et al., J Invest Dermatol, 97, 580-585 (1991)).

Collagen remodeling during the transition from granulation tissue to scar is dependent on continued synthesis and catabolism of collagen at a low rate. The degradation of collagen in the wound is controlled by several proteolytic enzymes, termed matrix metalloproteinases (MMP), which are secreted by macrophages, epidermal cells, and endothelial cells, as well as fibroblasts (Mignatti, P. et al., Proteinases and Tissue Remodeling. In Clark, R. Ed. The molecular and cellular biology of wound repair. 2nd Ed. New York, Plenum Press, 427-474 (1996)). Various phases of wound repair have been suggested to rely on distinct combinations of matrix metalloproteinases and tissue inhibitors of metalloproteinases (Madlener, M. et al, Exp Cell Res, 242, 201-210 (1998)).

Wounds gain only about 20 percent of their final strength in the first three weeks, during which fibrillar collagen has accumulated relatively rapidly and has been remodeled by contraction of the wound. Thereafter, the rate at which wounds gain tensile strength is slow, reflecting a much slower rate of accumulation of collagen and collagen remodeling with the formation of larger collagen bundles and an increase in the number of intermolecular cross-links.

II. Bone Structure, Fracture and Repair

Osseous tissue is a rigid form of connective tissue normally organized into definite structures, the bones. These form the skeleton, serve for the attachment and protection of the soft parts, and, by their attachment to the muscles, act as levers that bring about body motion. Bone is also a storage place for calcium that can be withdrawn when needed to maintain a normal level of calcium in the blood.

Bones can be classified according to their shape. Examples of bone types include: long bones whose length is greater than their widths (e.g., femur (thigh bone), humerus (long bone of the upper limb), tibia (shin bone), fibula (calf bone), radius (the outer of the two bones of the forearm), and ulna (inner of two bones of the forearm)), short bones whose length and width is approximately equal (e.g., carpals bones (wrist bones in the hand)), flat bones (e.g., cranium (skull bones surrounding the brain), scapula (shoulder blade), and ilia (the uppermost and largest bone of the pelvis)), irregular bones (e.g., vertebra), and Sesamoid bones, small bones present in the joints to protect tendons (fibrous connective tissues that connect muscles to the bones).

The Mandible (Lower Jaw)

The mandible, which is a U-shaped bone, is composed of 2 hemimandibles joined at the midline by a vertical symphysis. The hemimandibles fuse to form a single bone by 2 years of age. Each hemimandible is composed of a horizontal body with a posterior vertical extension termed the ramus.

On the anterior inferior midline region of the hemimandible body is a triangular thickening of bone termed the mental protuberance. The thickened inferior rim of the mental protuberance extends laterally from the midline and forms 2 rounded protrusions termed the mental tubercles. Located lateral to the midline on the external surface are the mental foramina that transmit the mental nerves and vessels. They usually are located below the apex of the second bicuspid and have 6-10 mm of variation in the anteroposterior dimension.

The rim of bone lateral to the mental tubercles extends posteriorly and ascends obliquely as the oblique line to join the anterior edge of the coronoid process. The inferior rim of the posterior body thickens and flares laterally where it attaches to the masseter muscle.

Body—Medial Surface

Just lateral to the symphysis on the inner surface of the mandible are 2 paired protuberances termed the superior and inferior mental spines. The genioglossus muscle attaches to the superior mental spines, and the geniohyoid muscle attaches to the inferior mental spines. Just lateral to the inferior mental spines on the inferior border of the mandible are 2 concavities called the digastric fossae, where the anterior digastric muscles attach.

Extending obliquely in a posterosuperior direction from the midline is a ridge of bone called the mylohyoid line, which serves as the attachment site for the mylohyoid muscle. Above and below the mylohyoid line on the inner mandibular body are 2 shallow convexities against which the sublingual and submandibular glands abut, respectively. Medial to the ascending edge of the anterior ramus is the retromolar trigone, located immediately behind the third molar.

Rami—Lateral Surface

The ramus extends vertically in a posterosuperior direction posterior to the body on each hemimandible. The mandibular angle is formed by the intersection of the inferior rim of the body and the posterior rim of the ascending ramus. The superior ramus bifurcates into an anterior coronoid process and a posterior condylar process. The concavity between the 2 processes is called the mandibular notch. The coronoid is thin and triangular. With the teeth in occlusion, its superior extent is medial to the zygomatic arch. The coronoid is the site of attachment of the temporalis muscle. Inferiorly, the condylar process has a narrow neck that widens to a globular head that articulates with the glenoid fossa of the temporal bone.

Rami—Medial Surface

On the medial surface of the ramus, just below the mandibular notch, is an aperture termed the mandibular foramen; the inferior alveolar nerve and blood vessels run through this aperture. Just medial to the mandibular foramen is the lingula, a triangular bony protuberance with its apex pointing posterosuperiorly toward the condylar head. Extending anteriorly and inferiorly from the mandibular notch toward the inferior rim of the body is the mylohyoid groove, through which the mylohyoid nerve runs.

Internal Anatomy

The mandible has a large medullary core with a cortical rim 2-4 mm thick. The inferior alveolar canal begins at the mandibular foramen and courses inferiorly, anteriorly, and toward the lingual surface in the ramus. In adults, the canal comes in close proximity to the roots of the third molar. In the mandibular body, the canal courses along the inferior border close to the lingual surface. Anteriorly, the canal runs typically inferior to the level of the mental foramen, to which it ascends at its terminal end.

The mandible houses the lower dentition, which in adults consists of 2 central and 2 lateral incisors, 2 canines, 2 first and 2 second premolars, and 3 sets of molars. Interdental septi run between the buccal and lingual cortices of the mandible, and interradicular septi run between the mesial and distal roots of the molars.

Maxilla (Upper Jaw)

The maxilla houses the upper teeth, forms the roof of the oral cavity, forms the floor of and contributes to the lateral wall and roof of the nasal cavity, houses the maxillary sinus, and contributes to the inferior rim and floor of the orbit. Two maxillary bones are joined in the midline to form the middle third of the face.

Anterior Surface

In the midline of the anterior surface of the maxilla is found a prominence, called the anterior nasal spine, with a lateral concave rim, called the nasal notch, that forms the floor of the piriform aperture. Inferiorly, the alveolar process of the maxilla houses the teeth, including central incisors, lateral incisors, canines, 2 premolars, and 3 molars in adults. The tooth roots form vertical, wavelike eminences in the anterior face of the maxilla; the canine root is the most prominent. The canine root forms a vertical ridge, termed the canine eminence, in the anterior face of the maxilla. The shallow fossae medial and lateral to the canine eminence are called the incisive fossa and the canine fossa, respectively.

Infraorbital Rim and Frontal Process

Superiorly, the maxillary bone is thickened in an inferior concavity that forms the infraorbital rim. Approximately 5-7 mm inferior to the rim lies the infraorbital foramen, which transmits the infraorbital nerve and vessels. The infraorbital rim extends medially and upward to form the frontal process of the maxilla. The frontal process articulates superiorly with the frontal bone, medially with the nasal bone, and posteriorly with the lacrimal bone. It has a smooth orbital surface that forms the vertical anterior lacrimal crest. Immediately posterior to the anterior lacrimal crest is a groove that forms the nasolacrimal canal.

Lateral Portion

The maxilla projects laterally to form the zygomatic process, which articulates with the zygoma to form the lateral portion of the inferior orbital rim. Viewed medially, the maxillary sinus is evident with its medially facing ostium. It articulates with the palatine bone posteriorly and with the ethmoid, lacrimal, and inferior concha bones medially. In front of the maxillary sinus is a vertical nasolacrimal groove that forms the nasolacrimal canal with the lacrimal bone posteriorly and terminates inferiorly under the attachment of the inferior concha.

Superior Surface

The superior surface of the maxilla forms the medial floor of the orbit. Posteriorly, the free edge forms the anterior border of the inferior orbital fissure. Medially, the orbital surface articulates with the ethmoid bone and lacrimal bone. Behind the frontal process of the maxilla and its anterior lacrimal crest is the nasolacrimal groove. Laterally, the orbital surface articulates with the orbital surface of the zygoma. On its inferior surface, the maxilla has a horizontal palatine process that forms the bulk of the hard palate.

The palatine processes of both maxillae articulate with each other in the midline and with the horizontal plate of the palatine bone posteriorly. Anteriorly in the midline articulation of both palatine processes is the incisive canal, which transmits the nasopalatine nerve and branches of the greater palatine vessels. From a medial view, the maxillary hiatus is evident, opening into the maxillary sinus that occupies the predominant portion of the body of the maxilla.

The zygoma forms the lateral portion of the inferior orbital rim, as well as the lateral rim and lateral wall of the orbit. Additionally, it forms the anterior zygomatic arch, from which the masseter muscle is suspended.

The masseter muscle acts to close the mandible for mastication and speech. On its lateral surface, the zygomatic bone has 3 processes. Inferiorly, a concave process projects medially to articulate with the zygomatic process of the maxilla, forming the lateral portion of the infraorbital rim. This concavity projects superiorly to form the frontal process that articulates with the frontal bone.

Posteriorly, a temporal process articulates with the zygomatic process of the temporal bone to form the zygomatic arch. On the medial surface of the zygoma is a smooth orbital plate that forms the lateral floor and lateral wall of the orbit. It articulates posteriorly with the greater wing of the sphenoid bone.

Just posterior to the lateral rim and slightly inferior to the frontozygomatic suture is the marginal tubercle of Whitnall, to which the lateral palpebral ligament attaches. On the smooth medial orbital surface are foramina, which transmit the zygomaticofacial and zygomaticotemporal nerves to their respective apertures on the lateral surface. The zygomaticofacial foramen is located just lateral to the lateral orbital rim at the junction of the frontal and maxillary processes. The zygomaticotemporal foramen is located on the posterior concave surface of the lateral orbital rim. (https://emedicine.medscape.com/article/835401-overview#a2, visited Jun. 20, 2018)

Alveolar Bone

Alveolar bone, which is one of three tissues that support the tooth (the other two are the periodontal ligament and the cementum) is formed by intramembranous bone formation during formation of the mandible and maxilla. It consists of two components. The first, the alveolar process of the maxilla and the mandible, forms to house the developing tooth buds, and, once erupted, the roots of the teeth. It provides structural support for the dentition. If the teeth are lost, the need for this process is lost, and through time the process is resorbed. The second. alveolar bone proper, is the portion of bone that lines the tooth socket and provides an attachment site for the periodontal ligament and its associated tooth. Chu, Tien-Min G. et al, Chapter 11—Craniofacial Biology, Orthodontics, and Implants, in Basic and Applied Bone Biology (2014) pages 225-242)

Types of Bone

Grossly, two types of bone may be distinguished: cancellous, trabecular or spongy bone, and cortical, compact, or dense bone.

Cortical bone, also referred to as compact bone or dense bone, is the tissue of the hard outer layer of bones, so-called due to its minimal gaps and spaces. This tissue gives bones their smooth, white, and solid appearance. Cortical bone consists of haversian sites (the canals through which blood vessels and connective tissue pass in bone) and osteons (the basic units of structure of cortical bone comprising a haversian canal and its concentrically arranged lamellae), so that in cortical bone, bone surrounds the blood supply. Cortical bone has a porosity of about 5% to about 30%, and accounts for about 80% of the total bone mass of an adult skeleton.

Cancellous Bone (Trabecular or Spongy Bone)

Cancellous bone tissue, an open, cell-porous network also called trabecular or spongy bone, fills the interior of bone and is composed of a network of rod- and plate-like elements that make the overall structure lighter and allows room for blood vessels and marrow so that the blood supply surrounds bone. Cancellous bone accounts for the remaining 20% of total bone mass but has nearly ten times the surface area of cortical bone. It does not contain haversian sites and osteons and has a porosity of about 30% to about 90%.

The head of a bone, termed the epiphysis, has a spongy appearance and consists of slender irregular bone trabeculae, or bars, which anastomose to form a lattice work, the interstices of which contain the marrow, while the thin outer shell appears dense. The irregular marrow spaces of the epiphysis become continuous with the central medullary cavity of the bone shaft, termed the diaphysis, whose wall is formed by a thin plate of cortical bone.

Both cancellous and cortical bone have the same types of cells and intercellular substance, but they differ from each other in the arrangement of their components and in the ratio of marrow space to bone substance. In cancellous bone, the marrow spaces are relatively large and irregularly arranged, and the bone substance is in the form of slender anastomosing trabeculae and pointed spicules. In cortical bone, the spaces or channels are narrow and the bone substance is densely packed.

With very few exceptions, the cortical and cancellous forms are both present in every bone, but the amount and distribution of each type vary considerably. The diaphyses of the long bones consist mainly of cortical tissue; only the innermost layer immediately surrounding the medullary cavity is cancellous bone. The tabular bones of the head are composed of two plates of cortical bone enclosing marrow space bridged by irregular bars of cancellous bone. The epiphyses of the long bones and most of the short bones consist of cancellous bone covered by a thin outer shell of cortical bone. Bone of the alveolar process is composed of both an outer layer of cortical bone and an inner region of cancellous bone. Chu, Tien-Min G. et al, Chapter 11—Craniofacial Biology, Orthodontics, and Implants, in Basic and Applied Bone Biology (2014) pages 225-242).

The type of bone in which a dental implant is placed determines the length of treatment for placing and restoring implants, because the implant has to integrate with the surrounding bone before a tooth and crown is placed on it. There are four types of bone in the human face: Type 1 bone is bone in which almost the entire bone is composed of homogenous compact bone; Type 2 bone, in which a thick layer of compact bone surrounds a core of dense trabecular bone; Type 3 bone, in which a thin lawyer of cortical bone surrounds a core of dense trabecular bone; and Type 4 bone characterized as a thin layer of cortical bone surrounding a core of low density trabecular bone of poor strength. Generally, mandibles are more densely corticated than maxillas, and both jaws tend to decrease in their cortical thickness and increase in their trabecular porosity as they move posteriorly. (Lekholm, Y., Zarb, G A, Albrektsson, T. "Patient selection and preparation. Tissue integrated prostheses." Chicago: Quntesscence Publishing Co., Inc. (1985), 199-209. The cortical bone thickness of the anterior region of alveolar bone is important for achieving dental implant stability. Kim, H-J, et al, "Cortical and cancellous bone thickness on the anterior region of alveolar bone in Korean: a study of dentate human cadavers," J. Adv. Prosthodont. (2012) 4(3): 146-52). The area surrounding the mandibular posterior teeth are supported by the thick buccal cortical bone. Bone of the alveolar process is composed of both an outer layer of cortical bone and an inner region of cancellous bone. Chu, Tien-Min G. et al, Chapter 11—Craniofacial Biology, Orthodontics, and Implants, in Basic and Applied Bone Biology (2014) pages 225-242).

Each bone, except at its articular end, is surrounded by a vascular fibroelastic coat, the periosteum. The so-called endosteum, or inner periosteum of the marrow cavity and marrow spaces, is not a well-demarcated layer; it consists of a variable concentration of medullary reticular connective tissue that contains osteogenic cells that are in immediate contact with the bone tissue.

Components of Bone

Bone is composed of cells and an intercellular matrix of organic and inorganic substances.

The organic fraction consists of collagen, glycosaminoglycans, proteoglycans, and glycoproteins. The protein matrix of bone largely is composed of collagen, a family of fibrous proteins that have the ability to form insoluble and rigid fibers. The main collagen in bone is type I collagen.

The inorganic component of bone, which is responsible for its rigidity and may constitute up to two-thirds of its fat-free dry weight, is composed chiefly of calcium phosphate and calcium carbonate, in the form of calcium hydroxyapatite, with small amounts of magnesium hydroxide, fluoride, and sulfate. The composition varies with age and with a number of dietary factors. The bone minerals form long fine crystals that add strength and rigidity to the collagen fibers; the process by which it is laid down is termed mineralization.

Bone Cells

Four cell types in bone are involved in its formation and maintenance. These are 1) osteoprogenitor cells, 2) osteoblasts, 3) osteocytes, and 4) osteoclasts.

Osteoprogenitor Cells

Osteoprogenitor cells arise from mesenchymal cells, and occur in the inner portion of the periosteum and in the endosteum of mature bone. They are found in regions of the embryonic mesenchymal compartment where bone formation is beginning and in areas near the surfaces of growing bones. Structurally, osteoprogenitor cells differ from the mesenchymal cells from which they have arisen. They are irregularly shaped and elongated cells having pale-staining cytoplasm and pale-staining nuclei. Osteoprogenitor cells, which multiply by mitosis, are identified chiefly by their location and by their association with osteoblasts. Some osteoprogenitor cells differentiate into osteocytes. While osteoblasts and osteocytes are no longer mitotic, it has been shown that a population of osteoprogenitor cells persists throughout life.

Osteoblasts

Osteoblasts, which are located on the surface of osteoid seams (the narrow region on the surface of a bone of newly formed organic matrix not yet mineralized), are derived from osteoprogenitor cells. They are immature, mononucleate, bone-forming cells that synthesize collagen and control mineralization. Osteoblasts can be distinguished from osteoprogenitor cells morphologically; generally they are larger than osteoprogenitor cells, and have a more rounded nucleus, a more prominent nucleolus, and cytoplasm that is much more basophilic. Osteoblasts make a protein mixture known as osteoid, primarily composed of type I collagen, which mineralizes to become bone. Osteoblasts also manufacture hormones, such as prostaglandins, alkaline phosphatase, an enzyme that has a role in the mineralization of bone, and matrix proteins.

Osteocytes

Osteocytes, star-shaped mature bone cells derived from osteoblasts and the most abundant cell found in compact bone, maintain the structure of bone. Osteocytes, like osteoblasts, are not capable of mitotic division. They are actively involved in the routine turnover of bony matrix and reside in small spaces, cavities, gaps or depressions in the bone matrix called lacuna. Osteocytes maintain the bone matrix, regulate calcium homeostasis, and are thought to be part of the cellular feedback mechanism that directs bone to form in places where it is most needed. Bone adapts to applied forces by growing stronger in order to withstand them; osteocytes may detect mechanical deformation and mediate bone-formation by osteoblasts.

Osteoclasts

Osteoclasts, which are derived from a monocyte stem cell lineage and possess phagocytic-like mechanisms similar to macrophages, often are found in depressions in the bone referred to as Howship's lacunae. They are large multinucleated cells specialized in bone resorption. During resorption, osteoclasts seal off an area of bone surface; then, when activated, they pump out hydrogen ions to produce a very acid environment, which dissolves the hydroxyapatite component. The number and activity of osteoclasts increase when calcium resorption is stimulated by injection of parathyroid hormone (PTH), while osteoclastic activity is suppressed by injection of calcitonin, a hormone produced by thyroid parafollicular cells.

Bone Matrix

The bone matrix accounts for about 90% of the total weight of compact bone and is composed of microcrystalline calcium phosphate resembling hydroxyapatite (60%) and fibrillar type I collagen (27%). The remaining 3% consists of minor collagen types and other proteins including osteocalcin, osteonectin, osteopontin, bone sialoprotein, as well as proteoglycans, glycosaminoglycans, and lipids.

Bone matrix is also a major source of biological information that skeletal cells can receive and act upon. For example, extracellular matrix glycoproteins and proteoglycans in bone bind a variety of growth factors and cytokines, and serve as a repository of stored signals that act on osteoblasts and osteoclasts. Examples of growth factors and cytokines found in bone matrix include, but are not limited to, Bone Morphogenic Proteins (BMPs), Epidermal Growth Factors (EGFs), Fibroblast Growth Factors (FGFs), Platelet-Derived Growth Factors (PDGFs), Insulin-like Growth Factor-1 (IGF-1), Transforming Growth Factors (TGFs), Bone-Derived Growth Factors (BDGFs), Cartilage-Derived Growth Factor (CDGF), Skeletal Growth Factor (hSGF), Interleukin-1 (IL-1), and macrophage-derived factors.

There is an emerging understanding that extracellular matrix molecules themselves can serve regulatory roles, providing both direct biological effects on cells as well as key spatial and contextual information.

The Periosteum and Endosteum

The periosteum is a fibrous connective tissue investment of bone, except at the bone's articular surface. Its adherence to the bone varies by location and age. In young bone, the periosteum is stripped off easily. In adult bone, it is more firmly adherent, especially so at the insertion of tendons and ligaments, where more periosteal fibers penetrate into the bone as the perforating fibers of Sharpey (bundles of collagenous fibers that pass into the outer circumferential lamellae of bone). The periosteum consists of two layers, the outer of which is composed of coarse, fibrous connective tissue containing few cells but numerous blood vessels and nerves. The inner layer, which is less vascular but more cellular, contains many elastic fibers. During growth, an osteogenic layer of primitive connective tissue forms the inner layer of the periosteum. In the adult, this is represented only by a row of scattered, flattened cells closely applied to the bone. The periosteum serves as a supporting bed for the blood vessels and nerves going to the bone and for the anchorage of tendons and ligaments. The osteogenic layer, which is considered a part of the periosteum, is known to furnish osteoblasts for growth and repair, and acts as an important limiting layer controlling and restricting the extend of bone formation. Because both the periosteum and its contained bone are regions of the connective tissue compartment, they are not separated from each other or from other connective tissues by basal laminar material or basement membranes. Perosteal stem cells have been shown to be important in bone regeneration and repair. (Zhang et al., 2005, J. Musculoskelet. Neuronal. Interact. 5(4): 360-362).

The endosteum lines the surface of cavities within a bone (marrow cavity and central canals) and also the surface of trabeculae in the marrow cavity. In growing bone, it consists of a delicate striatum of myelogenous reticular connective tissue, beneath which is a layer of osteoblasts. In the adult, the osteogenic cells become flattened and are indistinguishable as a separate layer. They are capable of transforming into osteogenic cells when there is a stimulus to bone formation, as after a fracture.

Bone Marrow

The marrow is a soft connective tissue that occupies the medullary cavity of the long bones, the larger central canals, and all of the spaces between the trabeculae of spongy bone. It consists of a delicate reticular connective tissue, in the meshes of which lie various kinds of cells. Two varieties of marrow are recognized: red and yellow. Red marrow is the only type found in fetal and young bones, but in the adult it is restricted to the vertebrae, sternum, ribs, cranial bones, and epiphyses of long bones. It is the chief site for the genesis of blood cells in the adult body. Yellow marrow consists primarily of fat cells that gradually have replaced the other marrow elements. Under certain conditions, the yellow marrow of old or emaciated persons loses most of its fat and assumes a reddish color and gelatinous consistency, known as gelatinous marrow. With adequate stimulus, yellow marrow may resume the character of red marrow and play an active part in the process of blood development.

Osteogenesis or Ossification

Osteogenesis or ossification is a process by which the bones are formed. There are three distinct lineages that generate the skeleton. The somites generate the axial skeleton, the lateral plate mesoderm generates the limb skeleton, and the cranial neural crest gives rise to the branchial arch, craniofacial bones, and cartilage. There are two major modes of bone formation, or osteogenesis, and both involve the transformation of a preexisting mesenchymal tissue into bone tissue. The direct conversion of mesenchymal tissue into bone is called intramembranous ossification. This process occurs primarily in the bones of the skull. In other cases, mesenchymal cells differentiate into cartilage, which is later replaced by bone. The process by which a cartilage intermediate is formed and replaced by bone cells is called endochondral ossification.

Intramembranous Ossification

Intramembraneous ossification is the characteristic way in which the flat bones of the scapula, the skull and the turtle shell are formed. In intramembraneous ossification, bones develop sheets of fibrous connective tissue. During intramembranous ossification in the skull, neural crest-derived mesenchymal cells proliferate and condense into compact nodules. Some of these cells develop into capillaries; others change their shape to become osteoblasts, committed bone precursor cells. The osteoblasts secrete a collagen-proteoglycan matrix that is able to bind calcium salts. Through this binding, the prebone (osteoid) matrix becomes calcified. In most cases, osteoblasts are separated from the region of calcification by a layer of the osteoid matrix they secrete. Occasionally, osteoblasts become trapped in the calcified matrix and become osteocytes. As calcification proceeds, bony spicules radiate out from the region where ossification began, the entire region of calcified spicules becomes surrounded by compact mesenchymal cells that form the periosteum, and the cells on the inner surface of the periosteum also become osteoblasts and deposit osteoid matrix parallel to that of the existing spicules. In this manner, many layers of bone are formed.

Intramembraneous ossification is characterized by invasion of capillaries into the mesenchymal zone, and the emergence and differentiation of mesenchymal cells into mature osteoblasts, which constitutively deposit bone matrix leading to the formation of bone spicules, which grow and develop, eventually fusing with other spicules to form trabeculae. As the trabeculae increase in size and number they become interconnected forming woven bone (a disorganized weak structure with a high proportion of osteocytes), which eventually is replaced by more organized, stronger, lamellar bone.

The molecular mechanism of intramembranous ossification involves bone morphogenetic proteins (BMPs) and the activation of a transcription factor called CBFA1. Bone morphogenetic proteins, for example, BMP2, BMP4, and BMP7, from the head epidermis are thought to instruct the neural crest-derived mesenchymal cells to become bone cells directly. BMPs activate the Cbfa1 gene in mesenchymal cells. The CBFA1 transcription factor is known to transform mesenchymal cells into osteoblasts. Studies have shown that the mRNA for mouse CBFA1 is largely restricted to the mesenchymal condensations that form bone, and is limited to the osteoblast lineage. CBFA1 is known to activate the genes for osteocalcin, osteopontin, and other bone-specific extracellular matrix proteins.

Endochondral Ossification (Intracartilaginous Ossification)

Endochondral ossification, which involves the in vivo formation of cartilage tissue from aggregated mesenchymal cells, and the subsequent replacement of cartilage tissue by bone, can be divided into five stages. The skeletal components of the vertebral column, the pelvis, and the limbs are first formed of cartilage and later become bone.

First, the mesenchymal cells are committed to become cartilage cells. This commitment is caused by paracrine factors that induce the nearby mesodermal cells to express two transcription factors, Pax1 and Scleraxis. These transcription factors are known to activate cartilage-specific genes. For example, Scleraxis is expressed in the mesenchyme from the sclerotome, in the facial mesenchyme that forms cartilaginous precursors to bone, and in the limb mesenchyme.

During the second phase of endochondral ossification, the committed mesenchyme cells condense into compact nodules and differentiate into chondrocytes (cartilage cells that produce and maintain the cartilaginous matrix, which consists mainly of collagen and proteoglycans). Studies have shown that N-cadherin is important in the initiation of these condensations, and N-CAM is important for maintaining them. In humans, the SOX9 gene, which encodes a DNA-binding protein, is expressed in the precartilaginous condensations.

During the third phase of endochondral ossification, the chondrocytes proliferate rapidly to form the model for bone. As they divide, the chondrocytes secrete a cartilage-specific extracellular matrix.

In the fourth phase, the chondrocytes stop dividing and increase their volume dramatically, becoming hypertrophic chondrocytes. These large chondrocytes alter the matrix they produce (by adding collagen X and more fibronectin) to enable it to become mineralized by calcium carbonate.

The fifth phase involves the invasion of the cartilage model by blood vessels. The hypertrophic chondrocytes die by apoptosis, and this space becomes bone marrow. As the cartilage cells die, a group of cells that have surrounded the cartilage model differentiate into osteoblasts, which begin forming bone matrix on the partially degraded cartilage. Eventually, all the cartilage is replaced by bone. Thus, the cartilage tissue serves as a model for the bone that follows.

The replacement of chondrocytes by bone cells is dependent on the mineralization of the extracellular matrix. A number of events lead to the hypertrophy and mineralization of the chondrocytes, including an initial switch from aerobic to anaerobic respiration, which alters their cell metabolism and mitochondrial energy potential. Hypertrophic chondrocytes secrete numerous small membrane-bound vesicles into the extracellular matrix. These vesicles contain enzymes that are active in the generation of calcium and phosphate ions and initiate the mineralization process within the cartilaginous matrix. The hypertrophic chondrocytes, their metabolism and mitochondrial membranes altered, then die by apoptosis.

In the long bones of many mammals (including humans), endochondral ossification spreads outward in both directions from the center of the bone. As the ossification front nears the ends of the cartilage model, the chondrocytes near the ossification front proliferate prior to undergoing hypertrophy, pushing out the cartilaginous ends of the bone. The cartilaginous areas at the ends of the long bones are called epiphyseal growth plates. These plates contain three regions: a region of chondrocyte proliferation, a region of mature chondrocytes, and a region of hypertrophic chondrocytes. As the inner cartilage hypertrophies and the ossification front extends farther outward, the remaining cartilage in the epiphyseal growth plate proliferates. As long as the epiphyseal growth plates are able to produce chondrocytes, the bone continues to grow.

Bone Remodeling

Bone constantly is broken down by osteoclasts and re-formed by osteoblasts in the adult. It has been reported that as much as 18% of bone is recycled each year through the process of renewal, known as bone remodeling, which maintains bone's rigidity. The balance in this dynamic process shifts as people grow older: in youth, it favors the formation of bone, but in old age, it favors resorption.

As new bone material is added peripherally from the internal surface of the periosteum, there is a hollowing out of the internal region to form the bone marrow cavity. This destruction of bone tissue is due to osteoclasts that enter the bone through the blood vessels. Osteoclasts dissolve both the inorganic and the protein portions of the bone matrix. Each osteoclast extends numerous cellular processes into the matrix and pumps out hydrogen ions onto the surrounding material, thereby acidifying and solubilizing it. The blood vessels also import the blood-forming cells that will reside in the marrow for the duration of the organism's life.

The number and activity of osteoclasts must be tightly regulated. If there are too many active osteoclasts, too much bone will be dissolved, and osteoporosis will result. Conversely, if not enough osteoclasts are produced, the bones are not hollowed out for the marrow, and osteopetrosis (known as stone bone disease, a disorder whereby the bones harden and become denser) will result.

Bone Regeneration and Fracture Repair

Fracture healing is the prototypic physiological model for bone regeneration. Principles of Tissue Engineering, $4^{th}$ Ed., Lanza, R., Langer, R. and Vacanti, J. Ed., Academic Press, Waltham, Mass. (2014) at 1204. It is a multistage process that is characterized by complex, yet well-orchestrated, predictable steps in response to an injury that begins immediately following the injury and ends following the remodeling of the newly formed bon into mature bone. This process has components that recapitulate the processes of de novo bone formation during embryogenesis. Id citing Ferguson, C. e al, "Does adult fracture repair recapitulate embryonic skeletal formation,? Mech. Dev. (1999) 87: 57).

The process of fracture healing is a multi-phase, multi-tiered series of events segmented into four main steps:
1) The formation of a hematoma (blood clot);
2) The migration and mitosis of mesenchymal cells;
3) Cartilage formation and substitution of cartilage by bone; and
4) Remodeling.

A fracture, like any traumatic injury, causes hemorrhage and tissue destruction. The first phase of fracture healing, the destructive phase, which lasts for about three days, is characterized by inflammation and local hypoxia. (Id. Citing Hollinger, J., Wong, M E, "The integrated processes of hard tissue regeneration with special emphasis on fracture healing," Oral Surg. Oral Med. Oral Pathol. Oral Radiol. Endod. (1996) 82: 594).

The constructive phase of regeneration follows the destructive phase. The first reparative changes are characteristic of those occurring in any injury of soft tissue. Proliferating fibroblasts and capillary sprouts grow into the blood clot and injured area, thus forming granulation tissue. The area also is invaded by poly morphonuclear leukocytes and later by macrophages that phagocytize the tissue debris. The granulation tissue gradually becomes denser, and in parts of it, cartilage is formed. This newly formed connective tissue and cartilage is designated as a callus. Soft callus formation provides the bone fracture site with a cartilaginous scaffold that acts as both a fixation and stabilization structure and a template for subsequent mineralization (Id. Citing Baroli, B. "From natural bone grafts to tissue engineering therapeutics: brainstorming on pharmaceutical formulative requirements and challenges." J. Pharm. Sci. (2009) 998: 1317). It serves temporarily in stabilizing and binding together the fracture bone. As this process is taking place, the dormant osteogenic cells of the periosteum enlarge and become active osteoblasts. On the outside of the fractured bone, at first at some distance from the fracture, osseous tissue is deposited. This formation of new bone continues toward the fractured ends of the bone and finally forms a sheath-like layer of bone over the fibrocartilaginous callus. As the amount of bone increases, osteogenic buds invade the fibrous and cartilaginous callus and replace it with a bony one. The cartilage undergoes calcification and absorption in the replacement of the fibrocartilaginous callus and intramembraneous bone formation also takes place. The newly formed bone is at first a spongy and not a compact type, and the callus becomes reduced in diameter. At the time when this subperiosteal bone formation is taking place, bone also forms in the marrow cavity. The medullary bone growing centripetally from each side of the fracture unites, thus aiding the bony union.

The process of repair is, in general, an orderly process, but it varies greatly with the displacement of the fractured ends of the bone and the degree of trauma inflicted. Uneven or protruding surfaces gradually are removed, and the healed bone, especially, in young individuals, assumes its original contour.

Osteogenesis and Angiogenesis

Skeletal development and fracture repair includes the coordination of multiple events such as migration, differentiation, and activation of multiple cell types and tissues. The development of a microvasculature and microcirculation is important for the homeostasis and regeneration of living bone, without which the tissue would degenerate and die. Recent developments using in vitro and in vivo models of osteogenesis and fracture repair have provided a better understanding of the recruitment nature of the vasculature in skeletal development and repair.

The vasculature transports oxygen, nutrients, soluble factors and numerous cell types to all tissues in the body. The growth and development of a mature vascular structure is one of the earliest events in organogenesis. In mammalian embryonic development, the nascent vascular networks develop by aggregation of de novo forming angioblasts into a primitive vascular plexus (vasculogenesis). This undergoes a complex remodeling process in which sprouting, bridging and growth from existing vessels (angiogenesis) leads to the onset of a functional circulatory system.

The factors and events that lead to the normal development of the embryonic vasculature are recapitulated during situations of neoangiogenesis in the adult. There are a number of factors involved in neoangiogenesis; these include, but are not limited to, Vascular Endothelial Growth Factor (VEGF), basic Fibroblast Growth Factor (bFGF), various members of the Transforming Growth factor beta (TGFβ) family and Hypoxia-Inducible Transcription Factor (HIF). Other factors that have angiogenic properties include the Angiopoietins, (Ang-1); Hepatocyte Growth Factor (HGF); Platelet-Derived Growth Factor (PDGF); Insulin-like Growth Factor family (IGF-1, IGF-2) and the Neurotrophins (NGF).

The VEGFs and their corresponding receptors are key regulators in a cascade of molecular and cellular events that ultimately lead to the development of the vascular system, either by vasculogenesis, angiogenesis or in the formation of the lymphatic vascular system. Although VEGF is a critical regulator in physiological angiogenesis, it also plays a significant role in skeletal growth and repair.

In the mature established vasculature, the endothelium plays an important role in the maintenance of homeostasis of the surrounding tissue by providing the communicative network to neighboring tissues to respond to requirements as needed. Furthermore, the vasculature provides growth factors, hormones, cytokines, chemokines and metabolites, and the like, needed by the surrounding tissue and acts as a barrier to limit the movement of molecules and cells. Signals and attractant factors expressed on the bone endothelium help recruit circulating cells, particularly hematopoietic cells, to the bone marrow and coordinate with metastatic cells to target them to skeletal regions. Thus, any alteration in the vascular supply to bone tissue can lead to skeletal pathologies, such as osteonecrosis (bone death caused by reduced blood flow to bones), osteomyelitis (infection of the bone or bone marrow by microorganism), and osteoporosis (loss of bone density). A number of factors have been found to have a prominent effect on the pathology of the vasculature and skeleton, including Osteoprotegerin (OPG), which inhibits Receptor Activator of NF-κB Ligand (RANKL)-induced osteoclastogenic bone resorption.

Both intramembraneous and endochondral bone ossification occur in close proximity to vascular ingrowth. In endochondral ossification, the coupling of chondrogenesis and osteogenesis to determine the rate of bone ossification is dependent on the level of vascularization of the growth plate. For example, vascular endothelial growth (VEGF) factor isoforms are essential in coordinating metaphyseal and epiphyseal vascularization, cartilage formation, and ossification during endochondral bone development. HIF-1 stimulates transcription of the VEGF gene (and of other genes whose products are needed when oxygen is in short supply). The VEGF protein is secreted, diffuses through the tissue, and acts on nearby endothelial cells.

The response of the endothelial cells includes at least four components. First, the cells produce proteases to digest their way through the basal lamina of the parent capillary or venule. Second, the endothelial cells migrate toward the source of the signal. Third, the cells proliferate. Fourth, the cells form tubes and differentiate. VEGF acts on endothelial cells selectively to stimulate this entire set of effects. Other growth factors, including some members of the fibroblast growth factor family, also can stimulate angiogenesis, but they influence other cell types besides endothelial cells. As the new vessels form, bringing blood to the tissue, the oxygen concentration rises, HIF-1 activity declines, VEGF production is shut off, and angiogenesis ceases.

The vascularization of cartilage regions in long bones occurs at different stages of development. In early embryonic development, blood vessels that originate from the perichondrium invaginate into the cartilage structures. During elevated postnatal growth, capillaries invade the growth plate of long bones. In adulthood, angiogenesis periodically can be switched on during bone remodeling in response to bone trauma or pathophysiological conditions such as rheumatoid arthritis (RA) and osteoarthritis (OA).

Bone has the unique capacity to regenerate without the development of a fibrous scar, which is symptomatic of soft tissue healing of wounds. This is achieved through the complex interdependent stages of the healing process, which mimic the tightly regulated development of the skeleton. Following trauma with damage to the musculoskeletal system, disruption of the vasculature leads to acute necrosis and hypoxia of the surrounding tissue. This disruption of the circulation leads to the activation of thrombotic factors in a coagulation cascade leading to the formation of a hematoma. The inflammatory response and tissue breakdown activate factors such as cytokines and growth factors that recruit osteoprogenitor and mesenchymal cells to the fracture site. The stimulation of the endosteal circulation in the fractured bone allows mesenchymal cells associated with growing capillaries to invade the wound region from the endosteum and bone marrow. At the edge of a bone fracture, the transiently formed granulation tissue is replaced by fibrocartilage. Concomitantly, the periosteum directly undergoes intramembranous bone formation leading to the formation of an external callus; while internally, the tissue is being mineralized to form woven bone. After stabilization of the bone tissue and vasculature in the bone fracture, the cell mediated remodeling cascade is activated where osteoclastic removal of necrotic bone is followed by the replacement of the large fracture callus by lamellar bone, the callus size is reduced and the normal vascular supply is restored.

A plurality of mediators associated with fetal and postnatal bone development plays a prominent role in the cascade response in bone fracture repair. These include but are not limited to BMP-2 and 4, VEGF, bFGF, TGF-β, and PDGF. VEGF expression is detected on chondroblasts, chondrocytes, osteoprogenitor cells and osteoblasts in the fracture callus where it is highly expressed in angioblasts, osteoprogenitor and osteoblast cells during the first seven days of healing but decreases after eleven days. Additionally, osteoclasts release heparinase that induces the release of the active form of VEGF from heparin, activating not only angiogenesis but also osteoclast recruitment, differentiation and activity leading to the remodeling of the fracture callus during endochondral ossification. Fractures in some cases fail to repair or unite resulting in fibrous filled pseudarthrosis. A number of contributing factors can lead to non-union or delayed union of bone fractures, such as, but not limited to, anti-inflammatory drugs, steroids, Vitamin C, Vitamin D and calcium deficiencies, tobacco smoking, diabetes, and other physiological disorders.

The absence of a functional vascular network is also an important factor in the lack of bone healing in non-union fractures. Studies have reported that angiogenic factors released from biomimetic scaffolds can enhance bone regeneration and that combination strategies that release both angiogenic and osteogenic factors can enhance the regenerative capacity of bone.

The critical sequential timing of osteoclast differentiation and activation, angiogenesis, recruitment of osteoprogenitor cells and the release of growth factors such as BMP-2 in osteogenesis and fracture repair may be enhanced by the synchronized endogenous production of angiogenic and osteogenic mediators. Studies in rat femoral drill-hole injury have shown differential expression of VEGF splicing isoforms along with its receptors, indicating an important role in the bone healing process. Other studies have demonstrated that angiogenesis occurs predominantly before the onset of osteogenesis in bone lengthening in an osteodistraction model.

Another angiogenic inducing growth factor, FGF-2, can accelerate fracture repair when added exogenously to the early healing stage of a bone. Although the mechanism has not been fully elucidated, it has the ability to stimulate angiogenesis and the proliferation and differentiation of osteoblasts to possibly aid the repair of bone fractures.

Dental Tissue

Alveolar Bone

Alveolar bone is that part of the maxilla and mandible which supports the teeth by forming an attachment for fibres of the periodontal ligament. It consists of two plates of cortical bone separated by spongy bone. In some areas, the alveolar bone is thin with no spongy bone. The alveolar bone and the cortical plates are thickest in the mandible. The spaces between the trabeculae of the spongy bone are filled with marrow, which consists of haematopoietic tissue in early life and of fatty tissue later. The shape and structure of the trabeculae reflect the stress-bearing requirements of the particular site. The surfaces of the inorganic parts of the bone are lined by osteoblasts, which are responsible for bone formation: those which become incorporated within the mineral tissue are called osteocytes and maintain contact with each other via canaliculi; osteoclasts are responsible for bone resorption and may be seen in the Howship's lacunae (Gulabivala, K., Ng, Y L, in Endodontics (4th Edition), Mosby (2014), pages 2-32, FIG. 1.150). Cortical bone adjacent to the ligament gives the radiographic appearance of a dense white line next to the dark line of the ligament (Id. see FIGS. 1.144, 1.145). The alveolar process (alveolar bone) is the thickened ridge of bone that contains the tooth sockets (dental alveoli) on the maxilla and the mandible, the bones that hold teeth in humans.

Tooth

A tooth has three anatomical divisions (crown, root and neck), and four structural components (enamel, dentin, cementum and pulp).

Enamel is the hardest, most mineralized biological tissue in the human body. It is composed of elongated hydroxyapatite crystallites bundled into rods or prisms, interspersed with crystalline interrods filling the interstitial space. Enamel cells, known as ameloblasts, are responsible for enamel development. Ameloblastin, TRAP and enamelin are key proteins found in enamel tissue whereas the enamel matrix is devoid of collagen, composed primarily of amelogenin. An intricate orchestration of signaling factors, such as BMPs (e.g., BMP-2, BMP-4, BMP-7), FGFs (e.g., FGF-3, -4, -9, -20), Wnt-3, 10a, 10b and transcription factors, such as, p21, Msx2 and Lef1 is responsible for morphogenesis of enamel. Self-assembly of amelogens to form amelogenin nanospheres play a role in nucleation of hydroxyapatite crystallization and enamel mineralization. Matrix processing enzymes, such as MMP-20, kallikrein-4 (KLK4), also known as enamel matrix serine protease-1 (EMSP-1), are involved in the complete elimination of the protein matrix and replacement with a mineralized matrix. (Fong et al., 2005, J. Dent. Educ., 69(5): 555-570). Ameloblasts arise from epithelial stem cells of ectodermal origin. They are lost after tooth eruption leaving no adult human ectodermal stem cells in the mature enamel. In contrast, rodent enamel retain a niche of epithelial stem cells, known as apical bud cells, for continuous enamel production. (Ulmer et al., 2010, Schweiz Monatsschr Zahnmed, 120:860-872).

Dentin is a hard, yellowish and elastic living connective tissue compartment with biomechanical properties similar to bone. The formation of dentin is driven by mesenchymally derived mature odontoblasts that are fully differentiated and nondividing and that form a single layer underneath the dentin in a mature tooth. A series of epithelial-mesenchymal interactions regulates odontoblast differentiation from neural crest cells in the first branchial arch and frontonasal processes. Mature dentin is comprised of a mantle, composed of intertubular and peritubular dentin made of a collagen fibril matrix, with odontoblast cell processes extending into dentin tubules. During dentinogenesis, odontoblasts secrete predentin, a mineralized tissue composed of type I collagen. Unlike osteogenesis, in dentinogenesis, as the predentin layer is formed, the odontoblasts recede instead of becoming embedded within the dentin matrix, leaving behind cells processes within dentinal tubules. Subsequently, the unmineralized predentin is converted to dentin by gradual mineralization of collagen. Dentinogenesis is directed by a series of highly controlled biochemical events that control the rates of collagen secretion, its maturation into thick fibrils, loss of proteoglycans, mineral formation including hydroxy apatite crystallization, and growth. The dentin matrix is primarily composed of collagens (e.g., types I, III and V) as well as other matrix proteins, including, but not limited to, phosphorylated and nonphosphorylated matrix proteins, proteoglycans, growth factors, metalloproteinases, alkaline phosphatase serum derived proteins, and phospholipids. (Fong et al., 2005, J. Dent. Educ., 69(5): 555-570). No stem cells have been identified in mature dentin.

The dental pulp is the tooth's living tissue that respond to pain and damage and initiates tissue repair. An odontoblast cell layer forms the outer boundary of the pulp and is associated with an underlying network of dendritic cells. A cell-free zone underlying the odontoblast layer is rich in nerve fibers and blood vessels. Similar to dentin, dental pulp also differentiates from neural crest-derived ectomesenchyme during tooth development.

Several sources of stem cells have been identified associated with pulp tissue. In immature teeth, apical papilla, the embryonal organ responsible for pulp differentiation, is the source for stem cells of apical papilla (SCAP). Mature dental pulp is the source of dental pulp stem cells (DPSC) whereas stem cells are also extracted from exfoliated deciduous teeth (SHED). Additional cells of the dental pulp core that function in pulpal defense, include, but are not limited to, macrophages, lymphocytes and mast cells. Pulp matrix is composed of collagens (e.g., types I, III V and VI), but lacks mineralization. Other noncollagenous proteins of the pulp matrix are similar in composition to dentin. The dental pulp is capable of responding to dentin tissue damage by secreting new dentin from old odontoblast populations or generation and secretion of dentin from new secondary odontoblast populations. (Fong et al., 2005, J. Dent. Educ., 69(5): 555-570).

The periodontium consists of tissues supporting the tooth crown, including a nonmineralized periodontal ligament (PDL) sandwiched between layers of mineralized tissues, including the cementum, alveolar bone and dentin. Cementum is a thin mineralized layer covering the dentin. Cementoblasts are cells responsible for cementum matrix secretion and subsequent mineralization. When cementoblasts become entrapped within cementum matrix, they are termed cementocytes. Cementoblasts are ectomesenchymal, being derived from neural crest cells, similar to PDL and alveolar bone. Like bone and dentin, cementum is a collagenous mineralized tissue that hardens upon formation of carbonated hydroxyapatite. (Fong et al., 2005, J. Dent. Educ., 69(5): 555-570).

PDL is a space between cementum and alveolar bone. It represents a replacement of the dental follicle region in immature developing teeth. Mature PDL contains mostly periodontal fibroblasts as well as stem cells, known as the periodontal ligament stem cells (PDLSCs). The immature dental follicle is also a source of mesenchymal stem cells, known as dental follicle stem cells (DFSCs). (Fong et al., 2005, J. Dent. Educ., 69(5): 555-570).

Several dental stem cell markers have been identified. Stro-1 and Stro-4 are commonly used dental stem cell markers for all dental mesenchymal stem cells. Dental stem cells originating from the neural crest have the neural marker, nestin. An osteoblast marker, osteocalcin, is also used as a stem cell marker for DPSCs. Similarly, SCAPs express Oct-4, Nanog, SSEA-3, SSEA-4, TRA-1-60 and TRA-1-81. (Ulmer et al., 2010, Schweiz Monatsschr Zahnmed, 120:860-872).

Grafts

A graft is a tissue used for transplantation to a subject in need thereof. A common strategy employed in tissue engineering involves the seeding of decellularized natural ECM or synthetic scaffolds with a variety of different stem or progenitor cells that are capable of regeneration (see, for example, Flynn and Woodhouse, 2008, Organogenesis, 4(4): 228-235; Uriel et al., 2008, Biomaterials, 29: 3712-3719; Flynn, 2010, Biomaterials, 31: 4715-4724; Choi et al., Tissue Engg. C., 16(3): 387-396; Brown et al., 2011, Tissue Engg. C., 17(4): 411-421; Cheng et al., 2009, Tissue Eng. A, 15(2): 231-241; Li et al., 2011, Biomaterials, doi: 10:1016/j.biomaterials.2011.03.008; Butler et al., 2003, Connective Tissue Research, 44(S1): 171-178); Mercuri et al., J. Biomed. Mater. Res. A., 96(2): 422-435); Olson et al., 2011, Chonnam. Med. J. 47:1-13).

Osseous defects have been repaired by implanting a bone matrix comprising autologous or allogeneic mesenchymal stem cells (MSCs), which are considered immunologically neutral, meaning that the mesenchymal stem cells from the donor need not be tissue-matched to the recipient, thus allowing MSCs to be used effectively in allogeneic grafts. In addition, culture-expanded allogeneic MSCs have been implanted either directly or combined with a matrix, such as a gelatin-based or collagen-based matrix, or a bone matrix, in order to support differentiation of the MSCs in vivo.

In other instances, MSCs have been combined with a bone matrix from which bone marrow has been removed in order to remove undesirable cells, and the matrix then seeded with culture-expanded MSCs.

However, because the MSCs have been removed from the original stem cell niche and seeded onto a new bone matrix, the MSCs in such a composition may not be well-attached to the bone matrix.

Dental bone grafts may be performed to reverse bone loss or destruction caused by, for example, periodontal disease or trauma. Some grafts are performed to rebuild bone structure to support dental implants. Membranes may be used to stabilize the graft as it heals.

Bone healing around implants involves the activation of a sequence of osteogenic, vascular, and immunological events that are similar to those occurring during bone healing. Various cell types, growth factors and cytokines are involved and interact throughout the stages of osteointegration, including inflammation, vascularization, bone formation, and ultimately bone remodeling.

Sinus lifts are bone grafting procedures for subjects with bone loss in the upper jaw (maxilla). The graft material is placed in the space between the sinus membrane and sinus bony floor to help the body grow bone and form a thicker sinus floor. Once the graft site has healed, the jaw bone below the sinus may be used for dental implants. See, e.g., Smiler, D G et al, "Sinus lift grafts and endosseous implants. Treatment of the atrophic posterior maxilla. Dental Clinics of North America (1992) 36(1): 151-81.

Bone grafts may include crushed bone (cancellous and cortical), or a combination of crushed bone with other natural materials, and may further comprise synthetic biocompatible materials. Bone grafts of this type are intended to stimulate growth of healthy bone. Bone graft material often is provided by a supplier in a gel or slurry form, as opposed to a dry or granule form. See, e.g., US2017/0312081 and US2017/0203008, each of which is incorporated by reference in its entirety.

Autologous bone or allogeneic bone are the most commonly used materials to induce bone formation. For example, small pieces of bone may be placed into the vacant space in the subject. Sometimes larger solid pieces of bone are used to provide immediate structural support. Autologous bone is generally considered superior at promoting fusion. However, this procedure requires extra surgery to remove bone from another body area of the subject. Similarly, allogeneic bone and other bone graft substitutes, although eliminating the need for a second surgery, have drawbacks in that they have yet to be proven as cost effective and efficacious substitutes for autogenous bone fusion. See, e.g., Wang, W. and Yeung, K. W. K., "Bone grafts and biomaterials substitutes for bone defect repair: a review," Bioactive Materials 2 (2017): 224-47.

An alternative to autologous or allogeneic bone is the use of growth factors that promote bone formation. For example, studies have shown that the use of bone morphogenic proteins ("BMPs") results in better overall fusion, less time in the operating room and, more importantly, fewer complications for patients because it eliminates the need for the second surgery. [source] However, use of BMPs, although efficacious in promoting bone growth, not only can be prohibitively expensive, but BMPs are also pleiotropic meaning they exhibit broad spectra of biological activities in various tissues, and their signaling pathways are complex. See Miyazono, K., et al, "Bone morphogenetic protein receptors and signal transduction," J. Biochem. (20010) 147 (1): 35-51.

Reconstruction of periodontal and gingival tissues through periodontal plastic and reconstructive surgery often involves surgical procedures such as re-contouring of gum tissue as well as multi-stage grafting. In other situations, minimal invasive removal of excess gum tissue and sculpting of the gum line including sculpting of the underlying bone is required. Gum grafts are often provided to cover exposed roots or to provide adequate supportive tissue for teeth and dental implants. These can also include tissue graft grafting for reconstruction of defects surgically created during other oral surgery procedures including those of the buccal mucosa. In such situations the tissue graft is placed on the raw surface of soft tissue or bone surface and sutured in place. See, e.g., US2016/0022379, incorporated herein by reference in its entirety.

Oral surgery may also be required where the patient has oral cancer. For instance, lower gingival squamous cell carcinoma (SCC) can invade the mandibular bone and buccal mucosa. In such situations, en bloc surgery of malignant tumors can require reconstructive surgery such as segmental mandibulectomy and reconstruction of the mandible and intraoral mucosa with fibular flap. See, e.g., US2016/0022379, incorporated herein by reference in its entirety.

Surgical treatments, however, are not always effective to address these problems because of inadequate local bone conditions and impaired bone healing.

Oral soft tissue healing at teeth, implants and the edentulous ridge follows the same phases as skin wound healing. Hammerle, C H et al, "Biology of soft tissue wound-healing and regeneration—consensus report of Group 1 of the $10^{th}$ European workshop on Periodontology," J. Clin. Periodontol. (2014) Suppl. 15: S1-5). Histological studies in humans have not reported new attachment formation at teeth for the indications studied, and human histological data of soft tissue wound healing at implants are limited.

Sometimes dental implants fail. Implant failure can be divided into two categories. Early failure is any dental implant failure that occurs within the first 3-4 months after the procedure when an implant is placed but fails to integrate (become solidly embedded into the bone). Factors include poor blood supply to the dental implant area, resulting in insufficient healing; certain medications (like those used to treat osteoporosis); existing infections; among others. For example, patients with diabetes have been observed to have impaired wound healing. (Brem, H. and M. Tomic-Canic," Cellular and molecular basis of wound healing in diabetes," J. Clin. Invest. (2007) 117(5): 1219-1222.

Late or long-term failure describes the situation where an implant has integrated solidly, but after many months or years, bone loss occurs around the implant, which allows bacteria to invade and settle on the implant's rough surface. For example, type 1 diabetics show less bone mineral density and may be more prone to bone loss. Sudaraghavan, V. et al, "Diabetes and bone health: latest evidence and clinical implications", Ther. Adv. Muscloskeletal Dis. (2017) 9(3): 67-74).

There remains a need for grafts for repair and/or regeneration of hard and soft tissues, and combinations thereof to promote healing and long term function.

SUMMARY OF THE INVENTION

According to one aspect, the described invention provides a graft for bony tissue repair comprising (a) a three-dimensional carrier matrix comprising one or more of a collagen, tri-calcium phosphate, de-mineralized bone strips, de-mineralized bone particles, dentin, an amnion membrane, or a chorion membrane; (b) a growth factor composition comprising an autologous platelet-rich fibrin and (c) a cell culture composition comprising: a culture medium, a population of cells suspended in the culture medium, and cells impregnated on or in a surface of particles of a diameter from about 30 μm to about 40 μm; wherein: the particles are osteoconductive; a ratio of growth factor composition to cell culture composition in the graft is at least about 10:1 (v/v); the carrier matrix is supersaturated by the population of cells, and the graft is effective to regenerate a target hard tissue. According to some embodiments, the growth factor composition comprises one or more cytokine selected from the group consisting of vascular endothelial growth factor (VEGF), platelet-derived growth factor (PDGF), transforming growth factor-β (TGF-β), bone morphogenetic protein-2 (BMP-2), bone morphogenetic protein-7 (BMP-7), interleukin-1 (IL-1), epidermal growth factor (EGF), insulin-like growth factor (IGF-1), fibronectin, fibroblast growth factor (FGF), and neural epidermal growth-factor-like 1 (NELL1). According to some embodiments, the platelet rich fibrin contains platelet-rich plasma. According to some embodiments, the suspended population of cells comprises autologous fibroblasts, autologous stromal cells, allogeneic stromal cells; autologous mesenchymal stem cells, or allogeneic mesenchymal stem cells. According to some embodiments, the suspended stromal cells comprise allogeneic amniotic fluid-derived stromal cells or autologous, expanded bone marrow aspirate derived stromal cells. According to some embodiments, the suspended mesenchymal stem cells comprise autologous adipose-derived mesenchymal stem cells, autologous expanded tooth/pulp-derived mesenchymal stem cells, or allogeneic umbilical cord stem cells. According to some embodiments, the three-dimensional carrier matrix, the growth factor composition, and the cell culture composition of the graft are co-printed with a 3-D printer. According to some embodiments, the carrier matrix supersaturated by the population of cells comprises at least 10,000,000 cells.

According to another aspect, the described invention provides a dental implant comprising the aforementioned graft for bony tissue repair.

According to another aspect, the described invention provides a bone implant comprising the aforementioned graft for bony tissue repair.

According to another aspect, the described invention provides a method for producing a graft for bony tissue repair comprising: (a) preparing a growth factor composition comprising platelet-rich fibrin from peripheral blood of a subject; (b) preparing a cell culture composition by expanding in vitro a suspended population of cells in a culture medium comprising particles of a diameter of about 30 μm to about 40 μm, the cell culture composition comprising the suspended population of cells and the cells impregnated on or in a surface of the particles; wherein the particles are osteoconductive; (c) mixing the growth factor composition with the cell culture composition in a ratio of growth factor composition to cell culture composition of at least about 10:1 (v/v) to form a growth factor composition-cell culture composition mixture; (d) combining the growth factor composition-cell culture composition mixture with a three-dimensional carrier matrix comprising one or more of a collagen, tri-calcium phosphate, de-mineralized bone strips, de-mineralized bone particles, dentin, an amnion membrane, a chorion membrane or an amniochorion membrane, wherein the carrier matrix is supersaturated by the population of cells, to form the graft; and (e) sterilely decanting the complete graft onto a sterile surgical field. According to some embodiments of the method, the growth factor composition comprises one or more cytokine selected from the group consisting of vascular endothelial growth factor (VEGF), platelet-derived growth factor (PDGF), transforming growth factor-β (TGF-β), bone morphogenetic protein-2 (BMP-2), bone morphogenetic protein-7 (BMP-7), interleukin-1 (IL-1), epidermal growth factor (EGF), insulin-like growth factor (IGF-1), fibronectin, fibroblast growth factor (FGF), and neural epidermal growth-factor-like 1 (NELL1). According to some embodiments of the method, the platelet-rich fibrin comprises platelet-rich plasma. According to some embodiments of the method, in the preparing a cell culture composition by expanding in vitro a suspended population of cells step (b), the suspended population of cells comprises autologous fibroblasts, autologous stromal cells, allogeneic stromal cells; autologous mesenchymal stem cells or allogeneic mesenchymal stem cells, and wherein the carrier matrix is supersaturated by the suspended population of cells. According to some embodiments of the method, in step (b), the suspended stromal cells comprise allogeneic amniotic fluid-derived stromal cells or autologous, expanded bone marrow aspirate derived stromal cells. According to some embodiments of the method, in step (b), the suspended mesenchymal stem cells comprise autologous adipose-derived mesenchymal stem cells, autologous expanded tooth/pulp-derived mesenchymal stem cells, or allogeneic umbilical cord stem cells. According to some embodiments, in step (c), the mixing is by centrifugation. According to some embodiments, the method comprises forming the graft of step (d) by co-printing steps (a), (b) and (c) with a 3D printer. According to some embodiments, the cell culture composition comprises at least 10,000,000 cells. According to some embodiments, step (b) comprises expanding the population of cells in an automated cell reactor comprising capillary fibers, wherein the capillary fibers contain a coated inner surface, and wherein the cells become attached to the coated inner surface. According to some embodiments, step (b) further comprises adding additional cells to the cell culture composition by centrifugation. According to some embodiments, the method further comprises prefabricating the graft in a range of sizes, dimensions and geometry for one or more target implant sites, and storing the prefabricated grafts in liquid nitrogen for later use, wherein a collection of such grafts when stored comprises a graft bank.

According to another aspect, the described invention provides a dental implant comprising the graft produced by the aforementioned method.

According to another aspect, the described invention provides a bone implant comprising the graft produced by the aforementioned method.

According to another aspect, the described invention provides a graft for soft tissue repair comprising: (a) a flexible three-dimensional carrier matrix comprising one or more of a collagen, a fibrin gel, a fibrin membrane, a fibrin matrix, a hyaluronic acid membrane, an amnion membrane, a chorion membrane, an amnionchorion membrane, a synthetic absorbable mesh selected from the group consisting of a polylactic acid (PLA) mesh, a PLGA mesh, or a PLA/PGLA mesh, a synthetic absorbable membrane selected from the group consisting of a PLA membrane, a poly (glycolide-co-lactide) copolymer (PLGA) membrane, or PLA/PGLA membrane; a PLA mesh/PGLA membrane, or a PLA membrane/PGLA mesh; (b) a growth factor composition comprising an autologous platelet rich fibrin; and (c) a cell culture composition comprising: culture medium, a population of cells suspended in the culture medium, and cells impregnated on the surface of particles of a diameter from about 30 μm to about 40 μm; wherein the ratio of growth factor composition to cell culture composition in the graft is at least about 10:1 (v/v); wherein the carrier matrix is supersaturated by the population of cells in (c), and wherein the graft is effective to regenerate a target soft tissue. According to some embodiments, the growth factor composition comprises one or more cytokine selected from the group consisting of vascular endothelial growth factor (VEGF), platelet-derived growth factor (PDGF), transforming growth factor-β (TGF-β), bone morphogenetic protein-2

(BMP-2), bone morphogenetic protein-7 (BMP-7), interleukin-1 (IL-1), epidermal growth factor (EGF), insulin-like growth factor (IGF-1), fibronectin, fibroblast growth factor (FGF), and neural epidermal growth-factor-like 1 (NELL1). According to some embodiments, the platelet rich fibrin contains a platelet-rich plasma. According to some embodiments, the suspended population of cells comprises autologous expanded fibroblasts, autologous epithelial keratinocytes, expanded epithelial keratinocytes; autologous stromal cells, allogeneic stromal cells; autologous mesenchymal stem cells or allogeneic mesenchymal stem cells. According to some embodiments, the suspended population of stromal cells comprises allogeneic amniotic fluid-derived stromal cells or autologous, expanded bone marrow aspirate derived stromal cells. According to some embodiments, the suspended mesenchymal stem cells comprise autologous adipose-derived mesenchymal stem cells, autologous expanded tooth/pulp-derived mesenchymal stem cells, or allogeneic umbilical cord stem cells. According to some embodiments, the particles are osteoconductive. According to some embodiments, the carrier matrix supersaturated by the population of cells comprises at least 10,000,000 cells.

According to another aspect, the described invention provides a gingival graft comprising the aforementioned graft for soft tissue repair.

According to another aspect, the described invention provides a method for producing a soft tissue graft comprising: (a) preparing a growth factor composition comprising platelet-rich fibrin from peripheral blood of a subject; (b) preparing a cell culture composition by expanding in vitro a suspended population of cells in a culture medium comprising particles of a diameter from about 30 µm to about 40 µm, the cell culture composition comprising a cell culture composition comprising the suspended population of cells and the cells impregnated on the surface of the particles; wherein the cell culture composition are capable of regenerating a target soft tissue; (c) mixing the growth factor composition with the cell culture composition in a ratio of growth factor composition to cell culture composition of at least about 10:1 (v/v) to form a growth factor composition-cell culture composition mixture; (d) combining the growth factor composition-cell culture composition mixture with a flexible three-dimensional carrier matrix comprising one or more of a collagen, a fibrin gel, a fibrin membrane, a fibrin matrix, a hyaluronic acid membrane, an amnion membrane, a chorion membrane, an amnionchorion membrane, a synthetic absorbable mesh selected from the group consisting of a polylactic acid (PLA) mesh, PLA membrane, poly(glycolide-co-lactide) copolymer (PLGA) membrane, a PLGA mesh, or a PLA/PGLA mesh, a synthetic absorbable membrane selected from the group consisting of a PLA membrane, a poly(glycolide-co-lactide) copolymer (PLGA) membrane, or PLA/PGLA membrane; a PLA mesh/PGLA membrane, or a PLA membrane/PGLA mesh to form the graft; wherein the carrier matrix is supersaturated by the population of cells in (b), and (e) positioning the complete graft onto a sterile surgical field. According to some embodiments, the growth factor composition comprises one or more cytokine selected from the group consisting of vascular endothelial growth factor (VEGF), platelet-derived growth factor (PDGF), transforming growth factor-β (TGF-β), bone morphogenetic protein-2 (BMP-2), bone morphogenetic protein-7 (BMP-7), interleukin-1 (IL-1), epidermal growth factor (EGF), insulin-like growth factor (IGF-1), fibronectin, fibroblast growth factor (FGF), and neural epidermal growth-factor-like 1 (NELL1). According to some embodiments, the platelet-rich fibrin comprises a platelet-rich plasma. According to some embodiments, the suspended population of cells comprises autologous expanded fibroblasts, autologous epithelial keratinocytes, expanded epithelial keratinocytes; autologous stromal cells, allogeneic stromal cells; autologous mesenchymal stem cells or allogeneic mesenchymal stem cells. According to some embodiments, the suspended stromal cells comprise allogeneic amniotic fluid-derived stromal cells or autologous, expanded bone marrow aspirate derived stromal cells. According to some embodiments, the suspended mesenchymal stem cells comprise autologous adipose-derived mesenchymal stem cells, autologous expanded tooth/pulp-derived mesenchymal stem cells, or allogeneic umbilical cord stem cells. According to some embodiments, the carrier matrix supersaturated by the population of cells comprises at least 10,000,000 cells. According to some embodiments, step (b) comprises expanding the population of cells in an automated cell reactor comprising capillary fibers, wherein the capillary fibers contain a coated inner surface, and wherein the cells become attached to the coated inner surface. According to some embodiments, step (b) further comprises adding additional cells to the cell culture composition by centrifugation. According to some embodiments, the method further comprises prefabricating the graft in a range of sizes, dimensions and geometry for one or more target implant sites, and storing the prefabricated grafts in liquid nitrogen for later use, wherein a collection of such grafts when stored comprises a graft bank.

According to another aspect, the described invention provides a gingival implant comprising the soft tissue graft produced by the aforementioned method.

According to another aspect, the described invention provides a multilayer combination hard and soft tissue graft comprising: a treatment site specific, pre-shaped dimension, three-dimensional scaffold comprising (i) an inner layer comprising: a first three-dimensional carrier matrix comprising one or more of a collagen, tri-calcium phosphate, de-mineralized bone strips, de-mineralized bone particles, dentin, an amnion membrane, or a chorion membrane; a first growth factor composition comprising platelet-rich fibrin; a first cell culture composition comprising: a first culture medium, a first population of cells suspended in the culture medium, and a first population of cells impregnated in or on a surface of particles of a diameter from about 30 µm to about 40 µm; wherein the particles are osteoconductive; wherein a ratio of the first growth factor composition to the first cell culture composition in the graft is at least about 10:1 (v/v); and (ii) an outer layer comprising: a second flexible three-dimensional carrier matrix comprising one or more of a collagen, a fibrin gel, a fibrin membrane, an amnion membrane, a chorion membrane, a synthetic absorbable mesh selected from the group consisting of a polylactic acid (PLA) mesh, a PLA membrane, a poly(glycolide-co-lactide) copolymer (PLGA) membrane, a PLGA mesh, a PLA/PGLA mesh; a synthetic absorbable membrane selected from the group consisting of a PLA membrane, a poly(glycolide-co-lactide) copolymer (PLGA) membrane, or PLA/PGLA membrane; a PLA mesh/PGLA membrane, and a PLA membrane/PGLA mesh; a second growth factor composition comprising platelet-rich fibrin; a second cell culture composition comprising: a second culture medium, a second population of cells suspended in the culture medium, and cells impregnated on a surface of particles of a diameter from about 30 µm to about 40 µm; wherein the ratio of second growth factor composition to second cell culture composition in the graft is at least about 10:1 (v/v); wherein the first carrier matrix is supersaturated by the first population of cells, and the second carrier matrix is supersaturated by the second population of cells, and wherein the graft is effective to regenerate a target hard tissue and a target soft tissue. According to some embodiments, the inner layer of the scaffold is effective to regenerate bone, and the outer layer of the scaffold is effective to regenerate epithelial soft tissue. According to some embodiments, the first growth factor composition, the second growth factor composition, or both comprises one or more cytokine selected from the group consisting of vascular endothelial growth factor (VEGF), platelet-derived growth factor (PDGF), transforming growth factor-β (TGF-β), bone morphogenetic protein-2 (BMP-2), bone morphogenetic protein-7 (BMP-7), interleukin-1 (IL-1), epidermal growth factor (EGF), insulin-like growth factor (IGF-1), fibronectin, fibroblast growth factor (FGF), and neural epidermal growth-factor-like 1 (NELL1). According to some embodiments, the platelet rich fibrin contains platelet rich plasma. According to some embodiments, the first population of cells suspended in the first culture medium of the first cell composition comprises autologous expanded fibroblasts, autologous stromal cells, allogeneic stromal cells; autologous mesenchymal stem cells, or allogeneic mesenchymal stem cells, and wherein the carrier matrix is supersaturated by the suspended population of cells. According to some embodiments, the suspended stromal cells comprise allogeneic amniotic fluid-derived stromal cells or autologous, expanded bone marrow aspirate derived stromal cells. According to some embodiments, the suspended mesenchymal stem cells comprise autologous adipose-derived mesenchymal stem cells, autologous expanded tooth/pulp-derived mesenchymal stem cells, or allogeneic umbilical cord stem cells. According to some embodiments, the second population of cells suspended in the second culture medium of the second cell composition comprises autologous expanded fibroblasts, autologous expanded gingival epithelial keratinocytes; autologous expanded stromal cells, allogeneic stromal cells; autologous mesenchymal stem cells or allogeneic mesenchymal stem cells. According to some embodiments, the suspended stromal cells comprise allogeneic amniotic fluid-derived stromal cells or autologous, expanded bone marrow aspirate derived stromal cells. According to some embodiments, the suspended mesenchymal stem cells comprise autologous adipose-derived mesenchymal stem cells, autologous expanded tooth/pulp-derived mesenchymal stem cells, or allogeneic umbilical cord stem cells. According to some embodiments, the inner layer of the scaffold, the outer layer of the scaffold or both the inner layer and outer layer of the scaffold is/are formed by a 3D printer. According to some embodiments, the first growth factor composition and the second growth factor composition are the same. According to some embodiments, the graft is adapted for percutaneous injection for bony and soft tissue repair. According to some embodiments, each of the first carrier matrix supersaturated by the first population of cells, and the carrier matrix supersaturated by the second population of cells comprises at least 10,000,000 cells.

According to another aspect, the described invention provides a dental implant comprising the aforementioned multilayer combination hard and soft tissue graft.

According to another aspect, the described invention provides a bone implant comprising the aforementioned multilayer combination hard and soft tissue graft.

According to another aspect, the described invention provides a method of producing a multilayer combination hard and soft tissue graft comprising: (a) preparing a growth factor composition comprising platelet-rich fibrin from peripheral blood of a subject; (b) preparing a first cell culture composition by expanding in vitro a first suspended population of cells in a first culture medium comprising particles of a diameter from about 30 μm to about 40 μm, the first cell culture composition comprising a first population of cells suspended in the first culture medium and a first population of cells impregnated in or on a surface of the particles; (c) mixing a first portion of the growth factor composition with the first cell culture composition in a ratio of growth factor composition to cell culture composition of at least about 10:1 (v/v) to form a first growth factor composition-first cell culture composition mixture; (d) combining the first growth factor composition-first cell culture composition mixture of step (c) with a first three-dimensional carrier matrix comprising one or more of a collagen, tri-calcium phosphate, de-mineralized bone strips, de-mineralized bone particles, dentin, an amnion membrane, or a chorion membrane to form an inner layer of the multilayer graft; wherein the first carrier matrix is supersaturated by the first population of cells, (e) preparing a second cell culture composition by expanding in vitro a second suspended population of cells in a second culture medium comprising particles of a diameter from about 30 μm to about 40 μm, the second cell culture composition comprising a second population of cells suspended in the culture medium and a second population of cells impregnated on the surface of the particles; (f) mixing a second portion of the growth factor composition with the second cell culture composition in a ratio of growth factor composition to cell culture composition of at least about 10:1 (v/v) to form a second growth factor composition-second cell culture composition mixture; (g) combining the second growth factor composition-second cell culture composition mixture of step (f) with a second three-dimensional carrier matrix comprising one or more of a collagen, a fibrin gel, a fibrin membrane, a fibrin matrix, a hyaluronic acid membrane, an amnion membrane, a chorion membrane, an amnion/chorion membrane, a synthetic absorbable mesh selected from the group consisting of a polylactic acid (PLA) mesh, PLA membrane, poly(glycolide-co-lactide) copolymer (PLGA) membrane, a PLGA mesh, or a PLA/PGLA mesh, or a synthetic absorbable membrane selected from the group consisting of a PLA membrane, a poly (glycolide-co-lactide) copolymer (PLGA) membrane, or PLA/PGLA membrane; a PLA mesh/PGLA membrane, and a PLA membrane/PGLA mesh to form an outer layer of the graft; wherein the second carrier matrix is supersaturated by the second population of cells, and (h) layering the inner layer over the outer layer to form the multilayer graft. According to some embodiments, the inner layer of the scaffold is effective to regenerate bone, and the outer layer of the scaffold is effective to regenerate epithelial soft tissue. According to some embodiments, the growth factor composition comprises one or more cytokine selected from the group consisting of vascular endothelial growth factor (VEGF), platelet-derived growth factor (PDGF), transforming growth factor-β (TGF-β), bone morphogenetic protein-2 (BMP-2), bone morphogenetic protein-7 (BMP-7), interleukin-1 (IL-1), epidermal growth factor (EGF), insulin-like growth factor (IGF-1), fibronectin, fibroblast growth factor (FGF), and neural epidermal growth-factor-like 1 (NELL1). According to some embodiments, the platelet rich fibrin contains platelet rich plasma. According to some embodiments, the first population of cells suspended in the first culture medium of the first cell composition comprises autologous expanded fibroblasts, autologous stromal cells, allogeneic stromal cells; autologous mesenchymal stem cells, or allogeneic mesenchymal stem cells, wherein the carrier matrix is supersaturated by the suspended population of cells. According to some embodiments, the suspended stromal cells comprise allogeneic amniotic fluid-derived stromal cells or autologous, expanded bone marrow aspirate derived stromal cells. According to some embodiments, the suspended mesenchymal stem cells comprise autologous adipose-derived mesenchymal stem cells, autologous expanded tooth/pulp-derived mesenchymal stem cells, or allogeneic umbilical cord stem cells. According to some embodiments, the second population of cells suspended in the second culture medium of the second cell composition comprises autologous expanded fibroblasts, autologous expanded gingival epithelial keratinocytes; autologous expanded stromal cells, allogeneic stromal cells; autologous mesenchymal stem cells or allogeneic mesenchymal stem cells. According to some embodiments, the suspended stromal cells comprise allogeneic amniotic fluid-derived stromal cells or autologous, expanded bone marrow aspirate derived stromal cells. According to some embodiments, the suspended mesenchymal stem cells comprise autologous adipose-derived mesenchymal stem cells, autologous expanded tooth/pulp-derived mesenchymal stem cells, or allogeneic umbilical cord stem cells. According to some embodiments, the method comprises forming the inner layer of the scaffold of step (d) by co-printing steps (a), (b) and (c) with a 3D printer. According to some embodiments, the method comprises forming the outer layer of the scaffold of step (g) by co-printing steps (d), (e) and (f) with a 3D printer. According to some embodiments, the layering in step (h) is achieved with a 3D printer. According to some embodiments, the method comprises combining the growth factor composition-first cell culture composition mixture with the first three-dimensional carrier matrix by centrifugation. According to some embodiments, the method comprises combining the growth factor composition-second cell culture composition mixture with the second three-dimensional carrier matrix by centrifugation. According to some embodiments, each of the first carrier matrix supersaturated by the first population of cells, and the carrier matrix supersaturated by the second population of cells comprises at least 10,000,000 cells. According to some embodiments, step (b) comprises expanding the first population of cells in an automated cell reactor comprising capillary fibers, wherein the capillary fibers contain a coated inner surface, and wherein the cells become attached to the coated inner surface. According to some embodiments, step (b) further comprises adding additional cells to the cell culture composition by centrifugation. According to some embodiments, step (e) comprises expanding the second population of cells in an automated cell reactor comprising capillary fibers, wherein the capillary fibers contain a coated inner surface, and wherein the cells becomes attached to the coated inner surface. According to some embodiments, step (b) further comprises adding additional cells to the cell culture composition by centrifugation. According to some embodiments, the method further comprises prefabricating the graft in a range of sizes, dimensions and geometry for one or more target implant sites, and storing the prefabricated grafts in liquid nitrogen for later use, wherein a collection of such grafts when stored comprises a graft bank.

According to another aspect, the described invention provides a dental implant comprising the multilayer combination hard and soft tissue graft produced by the aforementioned method.

According to another aspect, the described invention provides a bone implant comprising the multilayer combination hard and soft tissue graft produced by the aforementioned method.

DETAILED DESCRIPTION

Definitions

The term "adherent" as used herein refers to the act of sticking to, clinging, or staying attached.

The term "adipokine" as used herein refers to a factor secreted by adipose tissue.

The term "adipocyte" as used herein refers to the functional cell type of fat, or adipose tissue, that is found throughout the body, particularly under the skin. Adipocytes store and synthesize fat for energy, thermal regulation and cushioning against mechanical shock. Although the lineage of adipocytes is still unclear, it appears that mesenchymal stem cells can differentiate into two types of lipoblasts, one that give rise to white adipocytes and the other to brown adipocytes. Both types of adipocytes store fat. Adipose tissue may be brown or white adipose tissue, derived from, for example, subcutaneous, omental/visceral, mammary, gonadal, periorgan or other adipose tissue site. According to some embodiments, adipose tissue is subcutaneous white adipose tissue. The adipose tissue may comprise a primary cell culture or an immortalized cell line. The adipose tissue may be from any organism having fat tissue. According to some embodiments, the adipose tissue is mammalian, and according to some such embodiments the adipose tissue is human. A convenient source of adipose tissue is liposuction surgery. However, it will be understood that neither the source of adipose tissue nor the method of isolation of adipose tissue is critical. If adipose cells as described herein are desired for autologous transplantation into a subject, the adipose tissue will be isolated from that subject.

The term "adipogenic" as used herein refers to a potential of undifferentiated precursor cells to differentiate into fat forming or adipocompetent cells.

The term "adipose stem cell" or "ASC" as used herein refers to pluripotent stem cells, mesenchymal stem cells, and more committed adipose progenitors and stroma obtained from adipose tissue.

The term "administer" as used herein means to give or to apply.

The term "allogeneic" as used herein refers to being genetically different although belonging to or obtained from the same species.

The term "allogeneic graft" or "allograft" as used herein refers to a tissue that is grafted into or on the body of a recipient, where the recipient is an individual different from the donor that provides the source tissue but with both the recipient and the donor being of the same species.

Amniotic membranes. Amnionic membranes develop from extra-embryonic tissue and consist of a fetal component (the chorionic plate) and a material component (the deciduas), which are held together by the chorionic vili and connect the cytotrophoblastic shell of the chorionic sac to the decidua basalis. The fetal component, which includes the amniotic and chorionic fetal membranes, separates the fetus from the endomedium. The amniochorionic membrane forms the outer limits of the sac that encloses the fetus, while the innermost layer of the sac is the amniotic membrane.

From within outward, the amniotic membrane (AM) consists of (A) an epithelial monolayer, (B) a thick basement membrane, (C) a compact layer; (D) a fibroblast layer: and € a spongy layer. The amniotic epithelium, the inner most layer nearest to the fetus, and in contact with the amniotic fluid, consists of a single layer of cells uniformly arranged on the basement membrane. The epithelial layer can be removed while the basement membrane and stromal surfaces remain morphologically intact. The basement membrane is composed of a network of reticular fibers. The compact layer of stromal matrix adjacent to the basement membrane forms the main fibrous skeleton of the AM. The collagens of the compact layer are secreted by mesenchymal cells situated in the fibroblast layer. Interstitial collagens (types I and III) predominate and form parallel bundles that maintain the mechanical integrity of the AM. Collagens type V and VI form filamentous connections between interstitial collagens and the epithelial basement membrane. The fibroblast layer is composed of a loose fibroblast network embedded in a mass of reticulum. The spongy layer of the stromal matrix sits adjacent to the chorionic membrane, and represents the tissue of the extraembryonic celom, which is compressed between the amnion and the chorion. It contains a nonfibrillar meshwork of mostly type III collagen. The spongy layer is loosely connected to the chorionic membrane; hence the AM is easily separated from the chorion by means of blunt dissection. (Niknejad, H. et al, Eur. Cells and Materials (2008) 15: 88-99).

The term "amniotic stem cells" as used herein refers to pluripotent stem cells, multipotent stem cells, and progenitor cells derived from amniotic membrane, which can give rise to a limited number of cell types in vitro and/or in vivo under an appropriate condition, and expressly includes both amniotic epithelial cells and amniotic stromal cells.

The term "attached" as used herein refers to being fastened, fixed, joined, connected, bound, adhered to, or assembled with.

The terms "autologous" or "autogeneic" as used herein mean derived from the same organism.

The terms "autologous graft", "autogeneic graft", "autoplastic graft" or "autograft" as used herein refers to a tissue that is grafted into a new position in or on the body of the same individual.

The term "basic fibroblast growth factor" or "bFGF" as used herein refers to a multifunctional effector for many cells of mesenchymal and neuroectodermal origin that is a potent inducer of neovascularization and angiogenesis.

The term "biocompatible" as used herein refers to causing no clinically relevant tissue irritation, injury, toxic reaction, or immunological reaction to living tissue. The term "biomarkers" (or "biosignatures") as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention.

The term "bone" as used herein refers to a hard connective tissue consisting of cells embedded in a matrix of mineralized ground substance and collagen fibers. The fibers are impregnated with a form of calcium phosphate similar to hydroxyapatite as well as with substantial quantities of carbonate, citrate, and magnesium. Bone consists of a dense outer layer of compact substance or cortical substance covered by the periosteum and an inner loose, spongy substance; the central portion of a long bone is filled with marrow. The terms "cancellous bone" or "trabecular bone" as used herein refer to the spongy bone found in the inner parts of compact bone in which the matrix forms a lattice of large plates and rods known as the trabeculae, which anastomose to form a latticework. This latticework partially encloses many intercommunicating spaces filled with bone marrow. The marrow spaces are relatively large and irregularly arranged, and the bone substance is in the form of slender anastomosing trabeculae and pointed spicules. The terms "cortical bone" or "compact bone" as used herein refer to the dense outer layer of bone that consists largely of concentric lamellar osteons and interstitial lamellae. The spaces or channels are narrow and the bone substance is densely packed.

The term "bone graft" as used herein refers to bone transplanted from a donor site to a recipient site, without anastomosis of nutrient vessels. Bone can be transplanted within the same individual (i.e., autogeneic graft) or between different individuals (i.e., allogeneic graft).

The term "bound" or any of its grammatical forms as used herein refers to the capacity to hold onto, attract, interact with, or combine with.

The term "carrier" as used herein refers to a pharmaceutically acceptable inert agent or vehicle for delivering one or more active agents to a subject, and often is referred to as "excipient". The carrier must be of sufficiently high purity and of sufficiently low toxicity to render it suitable for administration to the subject being treated. The carrier further should maintain the stability and bioavailability of an active agent.

The term "cell" is used herein to refer to the structural and functional unit of living organisms and is the smallest unit of an organism classified as living.

The term "cementum" as used herein refers to a calcified tissue that supports attachment of a tooth to mandibular or maxillar bone through periodontal ligaments. Exposed cementum can result in resorption of cementum and exposure of the underlying dentin, therefore, hypersensitivity and pain.

The term "chondrocytes" as used herein refers to cells found in cartilage that produce and maintain the cartilaginous matrix. From least to terminally differentiated, the chondrocytic lineage is (i) Colony-forming unit-fibroblast (CFU-F); (ii) mesenchymal stem cell/marrow stromal cell (MSC); (3) chondrocyte. The term "chondrogenesis" refers to the formation of new cartilage from cartilage forming or chondrocompetent cells.

The term "chorion" as used herein refers to the outer fetal membrane that surrounds the amnion, the embryo, and other membranes and entities in the womb. A spongy layer of loosely arranged collagen fibers separates the amniotic and chorionic mesoderm. The chorionic membrane consists of mesodermal and trophoblastic regions. Chorionic and amniotic mesoderm are similar in composition. A large and incomplete basal lamina separates the chorionic mesoderm from the extravillous trophoblast cells. The latter, similar to trophoblast cells present in the basal plate, are dispersed within the fibrinoid layer and express immunohistochemical markers of proliferation. The Langhans fibrinoid layer usually increases during pregnancy and is composed of two different types of fibrinoid: a matrix type on the inner side (more compact) and a fibrin type on the outer side (more reticulate). At the edge of the placenta and in the basal plate, the trophoblast interdigitates extensively with the decidua (Cunningham, F. et al., The placenta and fetal membranes, Williams Obstetrics, 20th ed. Appleton and Lange, 1997, 95-125; Benirschke, K. and Kaufmann, P. Pathology of the human placenta. New York, Springer-Verlag, 2000, 42-46, 116, 281-297). The chorion, which interfaces maternal tissues, consists of four layers. These are, from within outward: (F) the cellular layer; a thin layer consisting of an interlacing fibroblast network, which is frequently imperfect or completely absent; (G) a reticular layer, which consists of a reticular network, the fibers of which tend to be parallel, along with a few fibroblasts and many Hofbauer cells; (H) a pseudo-basement membrane, which is a layer of dense connective tissue firmly adherent to the reticular layer above, and which sends anchoring and branching fibers down into the trophoblast; and (I) a trophoblast layer, which is the deepest layer of the chorion consisting of from two to 10 layers of trophoblast cells In contact, on their deeper aspect, with maternal decidua. This layer contains the chorionic villi. (Bourne, G L, Am. J. Obstet. & Gynec. (1960) 79 (6): 1070-1073).

The term "collagen" as used herein is meant to refer to a family of genetically distinct molecules, all of which have a unique triple helix configuration of three polypeptide subunits known as α chain; at least 13 types of collagen have been identified, each with a different polypeptide chain. For example, Type I collagen is the most abundant; it forms large well-organized fibrils of high tensile strength. Type II collagen is unique to cartilage, nucleus pulposis, notochord and vitreous body; it forms as thin highly glycosylated fibrils. Type III collagen is characteristic of reticular fibers. Type IV collagen is a less distinctly fibrillary form of collagen characteristic of basement membranes. Type V collagen is a quantitatively minor component of predominantly type I collagen fibrils in most non-cartilaginous tissues. Several isoforms of type V collagen exist, which differ in the type and ratio of constituent chains, including heterotypic molecules containing type XI collagen chains. The most abundant and widely distributed isoform is α1 (V)2α2(V), which forms heterotypic fibrils with type I collagen. Type V collagen has an essential regulatory role in collagen fibril initiation. (Wenstrup, r J et al, J. Biol. Chem. 279: 53331-53337).

The term "compatible" as used herein means that components of a composition are capable of being combined with each other in a manner such that there is no interaction that would substantially reduce the efficacy of the composition under ordinary use conditions.

The term "component" as used herein refers to a constituent part, element, or ingredient.

The term "composite graft" as used herein refers to a graft composed of two or more tissue types.

"Concentrate" and its various grammatical forms in relation to PRP or PRF refers to removal or reduction of liquid components in the separation of PRP or PRF from whole blood. For example, centrifugation, spectrometry, filtration, decanting, gravity settling, or other methods of concentrating platelets from platelet-containing fluids can be used.

The term "condition" as used herein refers to a variety of health states and is meant to include disorders or diseases caused by any underlying mechanism or disorder, injury, and the promotion of healthy tissues and organs.

The term "contact" and its various grammatical forms as used herein refers to a state or condition of touching or of immediate or local proximity. Contacting a composition to a target destination may occur by any means of administration known to the skilled artisan.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; TNF-related molecules, including TNFα and lymphotoxin; immunoglobulin super-family members, IL-1; and the chemokines, a family of molecules that play a critical role in a wide variety of immune and inflammatory functions. The same cytokine can have different effects on a cell depending on the state of the cell. Cytokines often regulate the expression of, and trigger cascades of other cytokines. Nonlimiting examples of cytokines include e.g., IL-1α, IL-1β, IL-2, IL-3, IL-4, IL-5, IL-6, IL-7, IL-8, IL-9, IL-10, IL-11, IL-12/IL-23 P40, IL13, IL-17, IL-18, TGF-β, IFN-γ, GM-CSF, Gro.alpha., MCP-1 and TNF-α.

The term "Demineralized Cortical Bone" or "DCB" as used herein refers to a demineralized allograft cortical bone that has osteoconductive and osteoinductive activity. Demineralized cortical bone matrices are prepared by acid extraction of allograft bone, resulting in loss of most of the mineralized component but retention of collagen and non-collagenous proteins, including growth factors.

The term "dental implant" as used herein refers to dental structures attached permanently to the jaw by means of metal anchors. The term "submucosal implant" as used herein refers to a dental implant resting beneath the mucosa. The term "subperiosteal implant" as used herein refers to an artificial dental appliance, made to conform to the shape of a bone and placed on its surface beneath the periosteum.

A "dental stem cell" refers to a postnatal stem cell that is isolated from a human tooth. Dental stem cells can be isolated from a permanent tooth or a deciduous tooth.

The term "dentin" or "dentine" as used herein refers to a portion of a tooth internal to the enamel and cementum that has a radially striated appearance owing to a large number of fine canals or tubules known as the dentinal tubules. "Dentinal tubules" run from the pulp cavity to the periphery of the dentin and are generally about two microns to ten microns in diameter at their base and somewhat narrower at their periphery. Dentinal tubules are not usually exposed to the environment in the oral cavity, as they are usually covered by enamel or cementum. The cementum in turn is often covered by the gums.

The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative". Derivatives can include chemical modifications of the peptide, such as alkylation, acylation, carbamylation, iodination, or any modification that derivatizes the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups, or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides that contain one or more naturally occurring amino acid derivative of the twenty standard amino acids, for example, 4-hydroxyproline, 5-hydroxylysine, 3-methylhistidine, homoserine, ornithine, or carboxyglutamiate, and can include amino acids that are not linked by peptide bonds. Such peptide derivatives can be incorporated during synthesis of a peptide, or a peptide can be modified by well-known chemical modification methods (see, e.g., Glazer et al., Chemical Modification of Proteins, Selected Methods and Analytical Procedures, Elsevier Biomedical Press, New York (1975)).

The term "differentiation" as used herein refers to the process of development with an increase in the level of organization or complexity of a cell or tissue, accompanied with a more specialized function.

The terms "disease" and "disorder" as used herein refer to an impairment of health or a condition of abnormal functioning.

The term "enamel" as used herein refers to the hard, highly mineralized outer surface of a tooth. Enamel mainly comprises minerals, with the primary mineral being hydroxyl apatite (HA, $Ca_5(PO_4)_3(OH)$). Enamel is a negatively charged surface, which naturally tends to attract positively charged ions such as hydrogen and calcium ions, while resisting negatively charged ions such as fluoride ions. Depending upon relative pH of surrounding saliva, the tooth enamel will lose or gain positively charged ions such as calcium ions. Generally saliva has a pH between 7.2 and 7.4. When the pH is lowered the fluid medium surrounding the tooth becomes undersaturated with respect to the tooth mineral phase and the tooth dissolves, releasing calcium and phosphate ions. This damages the enamel and creates a porous, sponge-like roughened surface. If saliva remains acidic over an extended period, then remineralization may not occur, and the tooth will continue to lose minerals, causing the tooth to weaken and ultimately to lose structure.

The term "endogenous" as used herein refers to that which is naturally occurring, incorporated within, housed within, adherent to, attached to, or resident in.

The term "expand" and its various grammatical forms as used herein refers to a process by which dispersed living cells propagate in vitro in a nutrient medium that results in an increase in the number or amount of viable cells.

The term "extracellular matrix" or "ECM" as used herein refers to a scaffold in a cell's external environment with which the cell interacts via specific cell surface receptors. Three types of extracellular matrix contribute to the organization, physical properties and function of tissue: the basement membrane; provisional matrix, and connective tissue (interstitial matrix or stroma). Sephel, G. C. and Woodward, S. C., 3. Repair, Regeneration and Fibrosis," in Rubin's Pathology, Rubin, R. and Strayer, D. S. Eds; $5^{th}$ Ed., Wolters Kluwer Health, /Lippincott Williams & Wilkins, Philadelphia, Pa. (2008), at 72-75. Basement membranes are constructed from extracellular matrix molecules, including collagen IV, laminin, enactin/nidogen, and perlecan, a peparan sulfate proteoglycan. They self-assemble into a sandwich-like structure composed of two interacting networks. Within different tissues, the expression of unique members of the collagen IV and laminin families imparts diversity to the basement membrane and the many structures and functions it supports. Basement membranes act as filters, cellular anchors and a surface for migrating epidermal cells after injury; determine cell shape, contribute to developmental morphogenesis and provide a repository for growth factors and chemotactic peptides. Id.

"Provisional matrix" refers to the temporary extracellular organizations of plasma-derived matrix proteins and tissue-derived components that accumulate at sites of injury (e.g., hyaluronan, tenascin and fibronectin). These molecules associate with the preexisting stromal matrix and serve to stop blood or fluid loss, and also support the migration of monocytes, endothelial cells, epidermal cells and fibroblasts to the wound site. Plasma-derived provisional matrix proteins include fibrinogen, fibronectin and vitronectin. These proteins become insoluble by binding to the stromal matrix and by forming cross-links. Id.

Stromal (Connective tissue) matrix. The stromal matrix forms a continuum between tissue elements, provides physical protection by conferring resistance to compression or stretching, and is a medium for the storage and exchange of bioactive proteins. It contains both extracellular matrix elements and individual cells that synthesize the matrix. The cells are primarily of mesenchymal origin and include fibroblasts, myofibroblasts, adipocytes, chondrocytes, osteocytes and endothelial cells. Bone marrow-derived cells (e.g., mast cells, macrophages, and transient leukocytes) also populate connective tissue.

The extracellular matrix serves many functions, including, but not limited to, providing support and anchorage for cells, segregating one tissue from another tissue, and regulating intracellular communication. The extracellular matrix is composed of an interlocking mesh of fibrous proteins and glycosaminoglycans (GAGs). Examples of fibrous proteins found in the extracellular matrix include collagen, elastin, fibronectin, and laminin. Type 1 collagen is the major constituent of bone. Type I and type III collagens are prominent in skin; type II collagen is the predominant form in cartilage. Elastin fibers, which impart elasticity to skin, large blood vessels and lungs, are decorated by microfibrillar proteins, such as fibrillin. Examples of GAGs found in the extracellular matrix include proteoglycans (e.g., heparin sulfate), chondroitin sulfate, keratin sulfate, and non-proteoglycan polysaccharide (e.g., hyaluronic acid). The term "proteoglycan" refers to a group of glycoproteins that contain a core protein to which is attached one or more glycosaminoglycans.

The term "factors" as used herein refers to nonliving components that have a chemical or physical effect. For example, a "paracrine factor" is a diffusible signaling molecule that is secreted from one cell type that acts on another cell type in a tissue. A "transcription factor" is a protein that binds to specific DNA sequences and thereby controls the transfer of genetic information from DNA to mRNA.

The term "fibroblast" as used herein refers to a connective tissue cell that makes and secrets collagen protein. Fibroblasts, the most common cell type found in connective tissues, play an important role in healing wounds. Like other cells of connective tissue, fibroblasts are derived from primitive mesenchyme (a type of loose connective tissue derived from all three germ layers and located in the embryos). In certain situations epithelial cells can give rise to fibroblasts, a process called epithelial-mesenchymal transition. The term "myofibroblasts" as used herein refers to fibroblasts in wound areas that have some characteristics of smooth muscle, such as contractile properties and fibers, and are believed to produce, temporarily, type III collagen.

The term "fibronectin" as used herein refers to a high-molecular weight (~440 kDa) extracellular matrix glycoprotein that binds to membrane-spanning cell-surface matrix receptor proteins ("integrins") and to extracellular matrix components such as collagen, fibrin and heparan sulfate proteoglycans (e.g. syndecans). Fibronectin exists as a dimer, consisting of two nearly identical monomers linked by a pair of disulfide bonds. There are multiple isoforms of fibronectin. Plasma fibronectin is soluble and circulates in the blood and other body fluids, where it is thought to enhance blood clotting, wound healing and phagocytosis. The other isoforms assemble on the surface of cells and are deposited in the extracellular matrix as highly insoluble fibronectin fibrils. The fibronectin fibrils that form on or near the surface of fibroblasts usually are aligned with adjacent intracellular actin stress fibers, which promote the assembly of secreted fibronectin molecules into fibrils and influence fibril orientation. Fibronectin plays a major role in cell adhesion, cell growth, cell migration and cell differentiation, and it is important for processes such as wound healing and embryonic development.

The term "flexible" as used herein refers to a material that is capable of being bent, disposed to yield, or pliable, usually without breaking.

The term "fragment" as used herein refers to a small part, derived from, cut off, or broken from a larger unit which retains the desired biological activity of the larger unit.

The terms "gingiva" and "gums" as used herein refer to mucosal tissue of the mouth that overlays the alveolar processes of the mandible and maxilla and surrounds the neck of each tooth. Gingiva comprises three domains: the free marginal gingiva (meaning the terminal edge of the gingiva that surrounds each tooth), the interdental gingiva (meaning the part of the gingiva that normally fill the space between two approximating teeth), and the attached gingiva (meaning the part of the gingiva which is firm and resilient and is bound to the underlying cementum and the alveolar bone, thus being immovable). Histologically, the gingiva contain two main components: the overlying epithelial structures and the underlying connective tissue. The epithelial structures contain mainly cells, including keratinocytes, Langerhans cells, melanocytes, Merkel cells, migrating polymorphonuclear leukocytes, and lymphocytes (e.g., T-lymphocytes). The ECM of the epithelial structures does not contain fibrous proteins, but it does contain type VIII collagen, glycoproteins, lipids, and proteoglycans. The underlying connective tissue contains substantial ECM, including collagens (types I, III, IV, and V), proteoglycans (including decorin, biglycan, versican, syndecan, CD44, and perlecan), fibronectin, osteonectin, vitronectin, elastin, and tenascin. The major cell type of the connective tissue is fibroblasts.

The term "gingival recession" as used herein refers to a tooth root (cementum) that is exposed to the environment as a result of retraction of the gumline from the crown of the teeth.

The term "graft" as used herein refers to a tissue transplanted from a donor to a recipient. It includes, but is not limited to, a self tissue transferred from one body site to another in the same individual ("autologous graft"), a tissue transferred between genetically identical individuals or sufficiently immunologically compatible to allow tissue transplant ("syngeneic graft"), a tissue transferred between genetically different members of the same species ("allogeneic graft" or "allograft"), and a tissue transferred between different species ("xenograft").

The term "growth" as used herein refers to a process of becoming larger, longer, or more numerous, or an increase in size, number, or volume.

The term "growth conduction" as used herein refers to a process by which a tissue is directed to regenerate or grow so as to conform to a material's surface. A growth-conductive surface is one that permits tissue growth on its surface or down into pores, channels or pipes. Growth-conductive material facilitates the spontaneous formation of a tissue by furnishing a microenvironment that supports deposition or adhesion of cells with the potential to differentiate into a mature cell type and optionally, vascularization. Examples of growth-conductive materials, include, without limitation, processed human bone (allograft bone), purified collagen, calcium phosphate ceramics, synthetic polymers, tissue-derived matrices, BMP-2 and 4, VEGF, bFGF, TGF-β, and PDGF.

The term "growth-conductive matrix" as used herein refers to a matrix that may be inert in and of itself but which supports three-dimensional tissue formation.

The term "growth factor" as used herein refers to extracellular polypeptide molecules that bind to a cell-surface receptor triggering an intracellular signaling pathway, leading to proliferation, differentiation, or other cellular response. Growth factors include, but are not limited to, cytokines and hormones.

Bone morphogenetic proteins (BMPs) are members of the transforming growth factor β family of secreted ligands. They were originally identified by their bone-forming actions, and play important but paradoxical roles in nervous system development. BMPs are pleiotrophic morphogens that act in concentration-dependent thresholds, which are critical in local cellular environments and are dependent on context and microenvironment. They have a multiplicity of different biological actions: in bone, they govern the three key steps in bone induction: chemotaxis; mitosis and differentiation. In addition, BMPs regulate hematopoiesis, stimulate extracellular matrix synthesis, influence cell survival maintenance and cell death/apoptosis. In vivo, they are bound to extracellular matrix components, such as collagens I and IV, heparin sulfate, heparin and the bone mineral hydroxyapatite. Tihere are a large number of BMP signal transduction components. (see Chen, H-L and Panchision, D. M., "Concise Review: Bone Morphogenetic Protein Pleiotropism in Neural Stem Cells and Their Derivatives—Alternate Pathways, Convergent Signals," Stem Cells (2007) 25: 63-68).

Fibroblast Growth Factor (FGF)

The fibroblast growth factor (FGF) family currently has over a dozen structurally related members. FGF1 is also known as acidic FGF; FGF2 is sometimes called basic FGF (bFGF); and FGF7 sometimes goes by the name keratinocyte growth factor. Over a dozen distinct FGF genes are known in vertebrates; they can generate hundreds of protein isoforms by varying their RNA splicing or initiation codons in different tissues. FGFs can activate a set of receptor tyrosine kinases called the fibroblast growth factor receptors (FGFRs). Receptor tyrosine kinases are proteins that extend through the cell membrane. The portion of the protein that binds the paracrine factor is on the extracellular side, while a dormant tyrosine kinase (i.e., a protein that can phosphorylate another protein by splitting ATP) is on the intracellular side. When the FGF receptor binds an FGF (and only when it binds an FGF), the dormant kinase is activated, and phosphorylates certain proteins within the responding cell, activating those proteins.

FGFs are associated with several developmental functions, including angiogenesis (blood vessel formation), mesoderm formation, and axon extension. While FGFs often can substitute for one another, their expression patterns give them separate functions. FGF2 is especially important in angiogenesis, whereas FGF8 is involved in the development of the midbrain and limbs.

The expression levels of angiogenic factors, such as VEGF, IGF, PDGF, HGF, FGF, TGFm Angiopoeitin-1, and stem cell factor (SCF) have been found to differ amongst bone-derived-, cartilage-derived-, and adipose-derived MSCs. (Peng et al., 2008, Stems Cells and Development, 17: 761-774).

Insulin-Like Growth Factor (IGF-1)

IGF-1, a hormone similar in molecular structure to insulin, has growth-promoting effects on almost every cell in the body, especially skeletal muscle, cartilage, bone, liver, kidney, nerves, skin, hematopoietic cell, and lungs. It plays an important role in childhood growth and continues to have anabolic effects in adults. IGF-1 is produced primarily by the liver as an endocrine hormone as well as in target tissues in a paracrine/autocrine fashion. Production is stimulated by growth hormone (GH) and can be retarded by undernutrition, growth hormone insensitivity, lack of growth hormone receptors, or failures of the downstream signaling molecules, including SHP2 and STAT5B. Its primary action is mediated by binding to its specific receptor, the Insulin-like growth factor 1 receptor (IGF1R), present on many cell types in many tissues. Binding to the IGF1R, a receptor tyrosine kinase, initiates intracellular signaling.

IGF-1 is one of the most potent natural activators of the AKT signaling pathway, a stimulator of cell growth and proliferation, and a potent inhibitor of programmed cell death. IGF-1 is a primary mediator of the effects of growth hormone (GH). Growth hormone is made in the pituitary gland, released into the blood stream, and then stimulates the liver to produce IGF-1. IGF-1 then stimulates systemic body growth. In addition to its insulin-like effects, IGF-1 also can regulate cell growth and development, especially in nerve cells, as well as cellular DNA synthesis.

Transforming Growth Factor Beta (TGF-β)

There are over 30 structurally related members of the TGF-β superfamily, and they regulate some of the most important interactions in development. The proteins encoded by TGF-β superfamily genes are processed such that the carboxy-terminal region contains the mature peptide. These peptides are dimerized into homodimers (with themselves) or heterodimers (with other TGF-β peptides) and are secreted from the cell. The TGF-β superfamily includes the TGF-β family, the activin family, the bone morphogenetic proteins (BMPs), the Vg-1 family, and other proteins, including glial-derived neurotrophic factor (GDNF, necessary for kidney and enteric neuron differentiation) and Mullerian inhibitory factor, which is involved in mammalian sex determination. TGF-β family members TGF-β1, 2, 3, and 5 are important in regulating the formation of the extracellular matrix between cells and for regulating cell division (both positively and negatively). TGF-β1 increases the amount of extracellular matrix epithelial cells make both by stimulating collagen and fibronectin synthesis and by inhibiting matrix degradation. TGF-βs may be critical in controlling where and when epithelia can branch to form the ducts of kidneys, lungs, and salivary glands.

The members of the BMP family were originally discovered by their ability to induce bone formation. Bone formation, however, is only one of their many functions, and they have been found to regulate cell division, apoptosis (programmed cell death), cell migration, and differentiation. BMPs can be distinguished from other members of the TGF-β superfamily by their having seven, rather than nine, conserved cysteines in the mature polypeptide. The BMPs include proteins such as Nodal (responsible for left-right axis formation) and BMP4 (important in neural tube polarity, eye development, and cell death).

Neural Epidermal Growth-Factor-Like 1 (NELL1)

Neural epidermal growth-factor-like 1 (NEL-like 1, NELL1) is a gene that encodes an 810-amino acid polypeptide, which trimerizes to form a mature protein involved in the regulation of cell growth and differentiation. The neural epidermal growth-factor-like (nel) gene first was detected in neural tissue from an embryonic chicken cDNA library, and its human orthologue NELL1 was discovered later in B-cells. Studies have reported the presence of NELL in various fetal and adult organs, including, but not limited to, the brain, kidneys, colon, thymus, lung, and small intestine.

Generally, the arrangement of the functional domains of the 810 amino acid NELL1 protein bears resemblance to thrombospondin-1 ("THBS1") and consists of a thrombospondin N-terminal domain ("TSPN") and several von Willebrand factor, type C ("VWC"), and epidermal growth-factor ("EGF") domains.

Additional studies have shown that there are two transcript variants encoding different isoforms. The nel-like 1 isoform 1 precursor transcript variant represents the longer transcript and encodes the longer isoform 1.

The conserved domains of the nel-like 1 isoform 1 precursor transcript reside in seven regions of the isoform 1 peptide and include: (1) a TSPN domain/Laminin G superfamily domain; (2) a VWC domain; (3) an EGF-like domain; (4) an EGF-like domain; (5) an EGF-like domain; (6) an EGF-like domain and (7) a VWC domain.

The first conserved domain region comprises amino acids (amino acids 29 to 213) that are most similar to a thrombospondin N-terminal-like domain. Thrombospondins are a family of related, adhesive glycoproteins, which are synthesized, secreted, and incorporated into the extracellular matrix of a variety of cells, including alpha granules of platelets following thrombin activation and endothelial cells. They interact with a number of blood coagulation factors and anticoagulant factors and are involved in cell adhesion, platelet aggregation, cell proliferation, angiogenesis, tumor metastasis, vascular smooth muscle growth, and tissue repair. The first conserved domain also comprises amino acids (amino acids 82 to 206; amino acids 98 to 209) that are similar to a Laminin G-like domain. Laminin G-like (LamG) domains usually are $Ca^{2+}$ mediated receptors that can have binding sites for steroids, 131-integrins, heparin, sulfatides, fibulin-1, and α-dystroglycans. Proteins that contain LamG domains serve a variety of purposes, including signal transduction via cell-surface steroid receptors, adhesion, migration and differentiation through mediation of cell adhesion molecules.

Much of what is known about NELL1 concerns its role in bone development. See, e.g., U.S. Pat. Nos. 7,884,066, 7,833,968, 7,807,787, 7,776,361, 7,691,607, 7,687,462, 7,544,486, and 7,052,856, the entire contents of which are incorporated herein by reference. It generally is believed that during osteogenic differentiation, NELL1 signaling may involve an integrin-related molecule and tyrosine kinases that are triggered by NELL1 binding to a NELL1 specific receptor and a subsequent formation of an extracellular complex. As thus far understood, in human NELL1 (hNELL1), the laminin G domain comprises about 128 amino acid residues that show a high degree of similarity to the laminin G domain of extracellular matrix ("ECM") proteins, such as human laminin α3 chain (hLAMA3), mouse laminin α3 chain (mLAMA3), human collagen 11α3 chain (hCOLA1), and human thrombospondin-1 (hTSP1). This complex facilitates either activation of Tyr-kinases, inactivation of Tyr phosphatases, or intracellular recruitment of Tyr-phosphorylated proteins. The ligand bound integrin (cell surface receptors that interact with ECM proteins such as, for example, laminin 5, fibronectin, vitronectin, TSP1/2) transduces the signals through activation of the focal adhesion kinase (FAK) followed by indirect activation of the Ras-MAPK cascade, and then leads to osteogenic differentiation through Runx2. The laminin G domain is believed to play a role in the interaction between integrins and a 67 kDa laminin receptor.

The second conserved domain (amino acids 273 to 331) and seventh conserved domain (amino acids 701 to 749; amino acids 703 to 749) are similar to von Willebrand factor type C (VWC) domains, also known as chordin-like repeats. VWC domains occur in numerous proteins of diverse functions. It is thought that these domains may be involved in protein oligomerization.

The third conserved domain (amino acids 434 to 471; amino acids 434 to 466), fourth conserved domain (amino acids 478 to 512), fifth conserved domain (amino acids 549 to 586; amino acids 549 to 582), and sixth conserved domain (amino acids 596 to 627; amino acids 596 to 634) are similar to a calcium-binding EGF-like domain. Calcium-binding EGF-like domains are present in a large number of membrane-bound and extracellular (mostly animal) proteins. Many of these proteins require calcium for their biological function. Calcium-binding sites have been found to be located at the N-terminus of particular EGF-like domains, suggesting that calcium-binding may be crucial for numerous protein-protein interactions. Six conserved core cysteines form three disulfide bridges as in non-calcium-binding EGF domains whose structures are very similar.

The nel-like 1 isoform 2 precursor transcript variant lacks an alternate in-frame exon compared to variant 1. The resulting isoform 2, which has the same N- and C-termini as isoform 1 but is shorter compared to isoform 1, has six conserved regions including a TSPN domain/LamG superfamily domain (amino acids 29 to 313); VWC domains (amino acids 273 to 331; amino acids 654 to 702); and calcium-binding EGF-like domains (amino acids 478 to 512; amino acids 434 to 471; amino acids 549 to 580).

NELL1 and its orthologs are found across several species including *Homo sapiens* (man), *Mus musculus* (mouse), *Rattus norvegicus* (rat), *Pan troglodytes* (chimpanzee), *Xenopus* (Silurana) *tropicalis* (frog), *Canis lupus familiaris* (dog), *Culex quinquefasciatus* (mosquito) *Pediculus humanus corporis* (head louse), *Aedes aegypti* (mosquito), *Ixodes scapularis* (tick), *Strongylocentrotus purpuratus* (purple sea urchin), and *Acyrthosiphon pisum* (pea aphid).

NELL1 comprises several regions susceptible to increased recombination. Studies have indicated that susceptibilities to certain diseases may be associated with genetic variations within these regions, suggesting the existence of more than one causal variant in the NELL1 gene. For example, in patients suffering irritable bowel syndrome ("IBS"), six different single nucleotide polymorphisms (SNPs) within NELL1 have been identified, with most of these SNPs near the 5' end of the gene and fewer at the 3' end. These include R136S and A153T (which reside in the TSPN) and R354W (which resides in a VWC domain). Additional studies have identified at least 26 variants comprising some of at least 263 SNPs within the NELL1 region.

The NELL1 protein is a secreted cytoplasmic heterotrimeric protein. The complete role NELL1 plays in vivo remains unknown.

Several studies have indicated that NELL1 may play a role in bone formation, inflammatory bowel disease, and esophageal adenocarcinoma, among others.

It generally is believed that NELL1 induces osteogenic differentiation and bone formation of osteoblastic cells during development. Studies have shown that the NELL1 protein (1) transiently activates the mitogen-activated protein kinase ("MAPK") signaling cascade (which is involved in various cellular activities such as gene expression, mito-sis, differentiation, proliferation and apotosis); and (2) induces phosphorylation of Runx2 (a transcription factor associated with osteoblast differentiation). Consequently, it generally is believed that upon binding to a specific receptor, NELL1 transduces an osteogenic signal through activation of certain Tyr-kinases associated with the Ras-MAPK cascade, which ultimately leads to osteogenic differentiation. Studies have shown that bone development is severely disturbed in transgenic mice where over-expression of NELL1 has been shown to lead to craniosynotosis (premature ossification of the skull and closure of the sutures) and NELL1 deficiency manifests in skeletal defects due to reduced chondrogenesis and osteogenesis.

Additional studies have supported a role for NELL-1 as a craniosynostosis-related gene. For example, three regions within the NELL-1 promoter have been identified that are directly bound and transactivated by Runx2. Further, studies in rat skullcaps have indicated that forced expression of Runx2 induces NELL-1 expression (which is suggestive that Nell-1 is a downstream target of Runx2).

Vascular Endothelial Growth Factor

Vascular endothelial growth factor (VEGF) is a key mediator of angiogenesis in many models (Nenfeld et al., 1999, FASEB J. 13; 9; Dvorak, 1999, Curr. Top Microbiol. Immunol. 237: 97; and Carmeliet & Collen, 1999, Curr. Top Microbiol. Immunol. 237: 133, etc.). VEGF promotes vascular endothelial cell migration, proliferation, inhibition of apoptosis, vasodilation, and increased vascular permeability. In several clinically relevant models of animal and human corneal neovascularization, angiogenesis is driven by increased secretion of VEGF (Amano et al., 1998, Invest Ophthalmol Vis Sci. 18-22; Cursiefen et al., 2004, J. Clin Invest. 113: 1040-50; and Philipp et al., 2000, Invest Ophthalmol Vis Sci. 41: 2514-22), and is also closely linked to infiltrating leukocytes (Amano et al., 1998, Invest Ophthalmol Vis Sci. 18-22).

The human VEGF family contains 6 members: VEGF-A VEGF-B, VEGF-C, VEGF-D, VEGF-E and placental growth factor (P1GF). In addition, multiple isoforms of VEGF-A, VEGF-B and P1GF are generated through alternative RNA splicing (Sullivan and Brekken, MAbs. 2010 March-April; 2(2):165-75). VEGF-A is the prototypic member of the family and is the most well characterized. VEGF-A has been shown to serve as a mitogenic factor to endothelial cells, promote endothelial cell survival and proliferation, induce cell migration and increase microvascular permeability. The VEGF family of proteins activate the VEGF signaling pathway by binding to the extracellular region of cell surface VEGF receptors (VEGFRs) to activate the VEGF signaling pathway.

Three receptors constitute the VEGF receptor family, which includes VEGFR-1 (Flt or Flt-1), VEGFR-2 (KDR), and VEGFR-3 (Flt-4), all of which have tyrosine-kinase activity (Neufeld et al., 1999, FASEB J. 13.9). The cDNA and amino acid sequences of human Flt-1 are found at accession number gi:56385329. Several studies have shown VEGFR-2 (through activation of MAP kinase and P1-3K (phosphatidylinositol 3-kinase) is the signal transducer for VEGF-induced mitogenesis, chemotaxis, and cytoskeletal reorganization and thus the principal receptor involved in angiogenesis (Thakker et al., 1999 J. Biol. Chem. 274; 10002-7; Dimmeler et al., 2000, FEBS Lett 477:258-62; Carmeliet & Collen, 1999, Curr. Top Microbol. Immunol. 237:97; Neufeld et al., 1999 FASEB J. 13:9; and Millauer et al., 1993, Cell 72: 835-46). VEGFR-3 is primarily involved in lymphangiogenesis (Cursiefen et al., 2004, Invest Ophthalmol Vis Sci. 45; 2666-73; Cursiefen et al., 2004, J. Clin Invest 113: 1040-50).

VEGF transcription is amplified in response to oncogenes, hypoxia, and other insults. Transcription factors for VEGF (HIF-1α and HIF-2α) are stabilized during hypoxia (Ahmed et al., 2000, Placenta 21 SA:S16-24; Wenger & Gassman, 1997, Biol. Chem. 378:609). Sensitivity to hypoxia is a major difference between VEGF and other angiogenic factors (Arbiser et al., 1997, Proc. Natl. Acad. Sci USA 94: 861; Okada et al., 1998, Proc. Natl Acad Sci. USA 95: 3609; and Petit et al., 1997, Am. J, Pathol. 151:1523). Elevated VEGF has been associated with a poor prognosis in cancer and with diabetic retinopathy (Ambati et al., 1997, Arch Ophthalmol 115: 1161-66). Strategies to inhibit VEGF have included blocking antibodies, decoy receptors for VEGF, and anti-VEGF antibodies (Kim et al., 1993, Nature 362; 841-44; Yuan, et al., 1996, Proc. Natl. Acad, Sci, USA. 93:14765-70; Lin et al, 1998, Cell Growth Differ. 9: 49-58; and Hasan & Jayson, 2001, Expert Opin Biol Ther. 1: 703-18). These strategies have generally reduced neovascularization by only 30-50% (Robinson et al., 1996, Proc. Natl Acad Sci USA 93; 4851-56; Aiello et al. 1995, Proc. Natl. Acad. Sci USA 92: 10457-61; Shen et al., 2002, Lab Invest 82:167-82; and Honda et al., 2000, Gene Ther. 7:978-75). These levels of neovascularization reduction are insufficient for the cornea, where angiogenesis should be minimized as much as possible for optimal visual clarity.

Further, in the course of normal VEGF signal transduction, membrane Flt heterodimerizes with VEGFR-2 upon VEGF binding (Autiero et al., 2003, Nat. Med.; and Kendall et al., 1996, Biochem Biophy Res Comm. 226:324-28). Physiologic Flt/VEGFR-2 heterodimers stimulate expression of fee genes for the transcription factor Ets-1 and matrix metalloproteinase 1 (MMP-1), phosphorylation of focal adhesive kinase (FAK), vinculin assembly and DNA synthesis (Kanno et al., 2000, Oncogene 19: 2138-46; Sato et al., 2000, Ann NY Acad Sci. 902:201-7). Ets-1 induces expression of Beatrix metalloproteinase 1 (MMP-1), MMP-3, MMP-9, matrix plasminogen activator; and .beta.3 integrin b, all involved, in matrix-neovessel interactions. MMP-1 facilitates digestion, of extracellular matrix to facilitate vascular ingrowth, while FAK helps mediate adhesion among endothelial cells and extracellular matrix. These events are critical to endothelial cell migration and proliferation.

VEGF is also well known to induce blood extravasation. This is also called a vascular permeability factor. This action is known to be due to its combination with a vascular endothelial growth factor receptor (VEGFR2), but interestingly, the mutation experiment of vascular endothelial growth factor showed that the vascular penetration of vascular endothelial growth factor was increased even though vascular endothelial growth factor-A did not bind to the vascular endothelial growth factor receptor. This suggested that there is another receptor for vascular endothelial growth factor (Stacker et al., 1999. J. Biol. Chem.). Other contemporary researchers established that this receptor is neuropilin (NRP) (Makinen et al., 1999. J. Biol. Chem.).

Neuropilin was first found in the Xenopus nervous system. Neuropilin is a transmembrane glycoprotein, and has two types: NRP1 and NRP2. Neuropilin acts as a coreceptor for VEGF receptors (VEGFRs) by VEGF family ligand binding. In particular, NRP1 binds to various VEGF ligands by acting as a co-receptor for VEGFR1, VEGFR2, and VEGFR3. On the other hand, NRP2 contributes to lymphangiogenesis and cell adhesion by acting as a co-receptor for VEGFR2 and VEGFR3. In addition, NRP1/NRP2 (NRP1/2) act as a co-receptor for the Plexin family receptors and bind to secreted class 3 semaphorin ligands (Sema3A, Sema3B, Sema3C, Sema3D, Sema3E, Sema3F and Sema3G).

Platelet-Derived Growth Factor

Platelet-derived growth factor (PDGF) plays a significant role in blood vessel formation (angiogenesis), the growth of blood vessels from already-existing blood vessel tissue. PDGF is a potent mitogen for cells of mesenchymal origin, including fibroblasts, smooth muscle cells, and glial cells. It has significant functions during embryonal development and in the control of blood vessel formation as an adult. PDGF plays an important role in driving the proliferation of undifferentiated mesenchyme and some progenitor populations. Overactivity or inappropriate PDGF signaling is associated with the development of certain malignant diseases, as well as non-malignant diseases characterized by excessive cell proliferation and other inflammatory disorders. In various embodiments, the binding proteins disclosed herein can bind one or more of the PDGF isoforms, and/or can bind one or more of the cognate PDGF receptors.

The human PDGF family contains four members: PDGF-A, PDGF-B, PDGF-C and PDGF-D. The four PDGF proteins form either homo- or heterodimers (for example, PDGF-AA, PDGF-AB, PDGF-BB, PDGF-CC and PDGF-DD), and they are inactive in their monomeric forms. The dimeric proteins bind to the extracellular region of cell surface PDGF receptors (PDGFRs) to activate the PDGF signaling pathway.

There are two types of PDGF receptors, PDGFR-α and PDGFR-β that form homo- or heterodimers (for example, PDGFR-αα, PDGFR-ββ and PDGFR-αβ) and contain extracellular regions comprising five Ig-like domains. The ligand-binding sites of the receptors are located to the first three Ig-like domains (D1 to D3).

The extracellular regions of the PDGFR dimers bind to different PDGF proteins. For example, PDGFR-αα specifically interacts with PDGF-AA, PDGF-AB, PDGF-BB and PDGF-CC. PDGFR-αβ specifically interacts with PDGF-AB, PDGF-BB, PDGF-CC and PDGF-DD. PDGFR-ββ specifically interacts with PDGF-BB, and PDGF-DD. PDGF-BB, the only PDGF that can bind to all three receptor dimer forms with high affinity, has been shown to be able to induce pericytes proliferation and migration both in vitro and in vivo. An extracellular region consisting of all five Ig-like domains of PDGFR-β (D1 to D5) was previously shown to antagonize responses stimulated by PDGF-B (Duan et al., J Biol Chem. 1991 Jan. 5; 266(1):413-8; Ueno et al., Science. 1991 May 10; 252(5007):844-8). Studies using PDGFRβ-Fc chimeric proteins demonstrated that D1 to D3 of human PDGFR-β are sufficient for high-affinity PDGF-B ligand binding (Heidaran et al., FASEB J. 1995 January; 9(1):140-5; Lokker et al., J Biol Chem. 1997 Dec. 26; 272(52):33037-44). Additionally, pre-dimerization of D1 to D3 of PDGFR-β fused to glutathione S-transferase (GST) improved binding affinity to PDGF-BB ligand compared to recombinant PDGFR-β D1-D3 protein (Leppanen et al., Biochemistry. 2000 Mar. 7; 39(9):2370-5).

Interleukin-1

The original members of the IL-1 superfamily are IL-1α, IL-1β, and the IL-1 Receptor antagonist (IL-1Rα, IL-1RA, IL-1ra, IL-1Rα). IL-1α and IL-1β are pro-inflammatory cytokines involved in immune defense against infection. IL-1Rα is a molecule that competes for receptor binding with IL-1α and IL-1β, blocking their role in immune activation. Recent years have seen the addition of other molecules to the IL-1 superfamily including IL-18 (see Dinarello et al., FASEB J., 8(15):1314-3225 (1994); Huising et al., Dev. Comp. Immunol., 28(5):395-413 (2004)) and six more genes with structural homology to IL-1α, IL-1β, or IL-1 RA. These latter six members are named IL1F5, IL1F6, IL1F7, IL1F8, IL1F9, and IL1F10. In accordance, IL-1α, IL-1β, and IL-1RA have been renamed IL-1F1, IL-1F2, and IL-1F3, respectively (see Sims et al., Trends Immunol., 22(10): 536-537 (2001); Dunn et al., Trends Immunol., 22(10): 533-536 (2001)). A further putative member of the IL-1 family has been described called IL-33 or IL-1F11, although this name is not officially accepted in the HGNC gene family nomenclature database.

Both IL-1α and IL-1β are produced by macrophages, monocytes and dendritic cells. They form an important part of the inflammatory response of the body against infection. These cytokines increase the expression of adhesion factors on endothelial cells to enable transmigration of leukocytes, the cells that fight pathogens, to sites of infection and re-set the hypothalamus thermoregulatory center, leading to an increased body temperature which expresses itself as fever. IL-1 is therefore called an endogenous pyrogen. The increased body temperature helps the body's immune system to fight infection. IL-1 is also important in the regulation of hematopoiesis. IL-1β production in peripheral tissue has also been associated with hyperalgesia (increased sensitivity to pain) associated with fever (Morgan et al., Brain Res., 1022(1-2): 96-100 (2004)). For the most part, these two forms of IL-1 bind to the same cellular receptor. This receptor is composed of two related, but non-identical, subunits that transmit intracellular signals via a pathway that is mostly shared with certain other receptors. These include the Toll family of innate immune receptors and the receptor for IL-18. IL-1α and IL-1β also possess similar biological properties, including induction of fever, slow wave sleep, and neutrophilia, T- and B-lymphocyte activation, fibroblast proliferation, cytotoxicity for certain cells, induction of collagenases, synthesis of hepatic acute phase proteins, and increased production of colony stimulating factors and collagen.

IL-1β is the predominant form produced by human monocytes both at the mRNA and protein levels. The two forms of human IL-1 share only 26% amino acid homology. Despite their distinct polypeptide sequences, the two forms of IL-1 have structural similarities (Auron et al., J. Mol. Cell Immunol., 2: 169-177 (1985)), in that the amino acid homology is confined to discrete regions of the IL-1 molecule.

IL-1α and IL-1β are produced as precursor peptides. In other words, they are made as a long protein that is then processed to release a shorter, active molecule, which is called the mature protein. Mature IL-1β, for example, is released from Pro-IL-1β following cleavage by a certain member of the caspase family of proteins, called caspase-1 or the interleukin-1 converting enzyme (ICE). The 3-dimensional structure of the mature forms of each member of the human IL-1 superfamily is composed of 12-14 β-strands producing a barrel-shaped protein.

Epidermal Growth Factor

Epidermal growth factor (EGF) is a 6.2 kDa polypeptide that specifically binds to the epidermal growth factor receptor (EGFR). EGF contains 53 amino acids with three internal disulfide bridges. EGF is one of the main growth factors that stimulates cell proliferation and motility during tissue regeneration. It also helps maintain tissue hemostasis through the regulation of epithelial cell proliferation and migration. Furthermore, EGF induces angiogenesis, which provides nutritional support to the tissue (Hudson and McCawley, Microsc. Res. Tech. 1998, 43: 444-455; Koivisto et al., Exp. Cell Res. 2006, 312: 2791-2805; Liang et al., Wound Repair Regen. 2008, 16: 691-698). This growth factor has multiple applications in the pharmaceutical field (Wong et al., Biotechnol. Genet. Eng. Rev. 2001, 18: 51-71; Girdler et al., Am. J. Clin. Oncol. 1995, 18: 403-406; Haedo et al., Rev. Esp. Enferm. Dig. 1996, 88: 409-413; Majima, Ophthalmologica 1998, 212:250-256); in cosmetics (Hasegawa and Yamamoto, Mech. Ageing. Dev. 1992, 66:107-114, U.S. Pat. No. 5,618,544) and in tissue engineering (Christopher et al., Biomacromolecules 2011, 12: 3139-3146).

EGF stimulates proliferation and differentiation of epidermal and epithelial tissues. EGF is a known mitogen for adult and fetal hepatocytes grown in culture, and its expression is up-regulated during liver regeneration. Evidence supports a role for EGF in malignant transformation and tumor progression. EGF enhances in vitro growth of human epithelial and mesenchymal-derived tumors. Over-expression of a secreted human EGF fusion protein (IgEGF) in fibroblasts enhances their transformation to fibrosarcomas. Transgenic mice with liver-specific over-expression of IgEGF develop hepatocellular carcinoma. Gene expression profiles comparing normal liver tissue to liver tumors in these mice suggest a role for an autocrine mechanism during EGF-induced hepatocarcinogenesis.

EGFR is a cell surface transmembrane receptor of the HER/ErbB receptor family that transmits signals (including mitogenic signals that drive cell proliferation) to the interior of a cell when activated, typically by the binding of any of a number of extracellular ligands such as EGR. EGFR ligands vary in their affinity for EGFR and are categorized as either high- or low-affinity ligands. It is thought that the high- and low-affinity interactions between EGFR and its ligands activate different signaling pathways. This signal transmission occurs through a cascade of intracellular events beginning with protein phosphorylation mediated by receptor tyrosine kinase activity.

Fibronectin

Fibronectin is a high-molecular weight glycoprotein of the extracellular matrix that binds to membrane-spanning receptor integrin proteins. Soluble fibronectin is composed of two nearly identical subunits that are joined by disulfide bonds (Petersen et al., Proc. Natl. Acad. Sci. U.S.A. 80:137-141 (1983)). The primary structure of each subunit is organized into three types of repeating homologous units, termed types I, II, and Ill. Fibronectin type Ill repeats are found in a number of extracellular matrix (ECM) proteins and consist of two overlapping β sheets.

The polymerization of fibronectin into the ECM is a cell-dependent process that is mediated by coordinated events involving the actin cytoskeleton and integrin receptors (Mao et al., Matrix Biol. 24(6):389-399 (2005) and Magnusson et al., Arterio. Thromb. Vasc. Biol. 18:1363-1370 (1998)). Most adherent cells, including epithelial cells, endothelial cells, fibroblasts, and smooth muscle cells, polymerize a fibrillar fibronectin matrix (Hynes et al., J. Cell Biol. 95:369-377 (1982)). There is evidence that the interaction of cells with either the soluble or ECM form of fibronectin gives rise to distinct cellular phenotypes (Morla et al., Nature 367:193-196 (1994) and Hocking et al., J. Biol. Chem. 275:10673-10682 (2000)). ECM fibronectin stimulates cell spreading (Gui et al., J. Biol. Chem. 281(46): 34816-34825 (2006)), growth (Sottile et al., J. Cell Sci. 111:2933-2943 (1998) and Sottile et al., J. Cell Sci. 113: 4287-4299 (2000)), and migration (Hocking et al., Am. J. Physiol. Lung Cell Mol. Physiol. 285:L169-L179 (2003)), as well as collagen deposition (Sottile et al., Mol. Biol. Cell 13:3546-3559 (2002) and Yelling et al., J. Biol. Chem. 277(40):37377-37381 (2002)) and organization (Hocking et al., J. Biol. Chem. 275:10673-10682 (2000)). Others have shown a role for fibronectin matrix assembly in the deposition of fibrinogen (Pereira et al., J. Cell Sci. 115(Pt 3):609-617 (2002)), fibrillin (Sabatier et al., Mol. Biol. Cell 20(3):846-858 (2009)), and tenascin C (Chung et al., J. Biol. Chem. 270:29012-29017 (1995)) into the ECM. Fibronectin matrix polymerization stimulates the formation of endothelial neovessels in collagen lattices (Zhou et al., Genes. Dev. 22(9):1231-1243 (2008)). Moreover, blocking fibronectin matrix polymerization inhibits cell growth (Sottile et al., J. Cell Sci. 111:2933-2943 (1998) and Mercurius et al., Circ. Res. 82:548-556 (1998)) and contractility (Hocking et al., J. Biol. Chem. 275:10673-10682 (2000)), alters actin organization (Hocking et al., J. Biol. Chem. 274:27257-27264 (1999)) and cell signaling (Bourdoulous et al., J. Cell Biol. 143:267-276 (1998)), and inhibits cell migration (Hocking et al., Am. J. Physiol. Lung Cell Mol. Physiol. 285:L169-L179 (2003)). Together, these studies indicate that fibronectin matrix polymerization plays a key role in establishing the biologically-active extracellular environment required for proper tissue function.

Fibronectin is involved in wound healing by contributing to hemostasis and phagocytosis, assisting in control of infection, promoting fibroblast migration and proliferation, enhancing epithelialization and organization of granulation tissue and, ultimately, by modifying the tensile strength of scar tissue (Grinnell, J Cell Biochem. (1984) 26(2):107-16). Plasma fibronectin has been demonstrated to be degraded in diabetic wounds (Wysocki and Grinnell, Lab Invest. (1990) 63(6):825-31) and impaired wound healing in diabetic rats was characterized by a reduction in plasma fibronectin at the wound site (Qiu et al., J Surg Res. (2007) 138(1):64-70).

Fibronectin accumulates at sites of injury and inflammation in vivo (Pettersson et al., Clin. Immunol. Immunopath 11:425-436 (1978); Grinnel et al. J. Invest. Derm. 76:181-189 (1981); Repesh et al. J. Histochem. Cytochem. 30(4):351-58 (1982); Torikata et al., Lab. Invest. 52(4):399-408 (1985); Carsons et al. Arth. Rheum 24(10):1261-67 (1981)) and is produced by cells in blood vessel walls at these sites. Clark et al., J. Exp. Med. 156:646-51 (1982); Clark et al., J. Immunol. 126(2):787-93 (1981); Clark et al., J. Invest. Derm. 79:269-76 (142); Clark et al., J. Clin. Invest. 74:1011-16 (1984).

Alternative splicing of fibronectin pre-mRNA leads to the creation of fibronectin mRNA having a different combination of exons, which in turn leads to the creation of several isoforms of fibronectin protein. In certain instances, alternative splicing of the fibronectin gene results in a fibronectin protein isoform containing the extra type III domain A (EDA). Fibronectin containing extra type III domain A (EDA) is implicated in the formation of fibrosis. See, e.g., Muro et al., Am. J. Resp. Crit. Care Med. 177:638 (2008).

The term "growth factor composition" is used herein to include the contents of platelet alpha, dense, and lambda granules that contain over 400 different bioactive proteins and biochemicals whose complex interactions in the healing process are not yet fully clarified, as well as components of the extracellular fluid or plasma. According to some embodiments, the growth factor composition is substantially free of other components typically found in conventional platelet enriched wound healing products, namely whole platelets, ghost platelets, white blood cells, red blood cells, bacteria, and other cellular debris.

The term "growth induction" as used herein refers to a process by which undifferentiated cells with the potential to differentiate into a mature cell type are stimulated to develop into an ensemble of cells, not necessarily identical, that together carry out a specific function. This ensemble of cells is termed a tissue.

The term "growth-inductive matrix" as used herein refers to a matrix containing a substance or substances capable of recruiting or stimulating local cells with the potential to differentiate into a mature cell type so that the cells are induced (meaning to cause, bring about, bring about, or trigger) to differentiate and/or produce a tissue.

The terms "growth-inductive components", "growth-inductive factors", and "growth-inductive factors" are used interchangeably to refer to the plethora of mediators associated with tissue development and repair. Exemplary growth-inductive factors including, but are not limited to, Adipsin, Alpha 1 acid glycoprotein, Angiogenin, Adiponectin, Colony stimulating factor-1, Angiopoietin 1, Apelin, Complement component inhibitor C1, Angiopoietin 2, ApoE, Complement CI, Angiotensinogen, Cortisol, Complement C2, Calcitonin, IGF-1, Complement C3, Chemerin factor 1, IGF, Complement C4, Cyclophilin A, Binding protein 7, Complement C7, Extracellular SOD, Lipoprotein lipase, Complement factor B, Galectin 1, Leptin, Complement factor C, Growth related oncogene (GRO), Complement factor D, FGF, Fasting induced adipose factor, Plasminogen activated inhibitor-1, C reactive protein, Hepatic growth factor (GF), Resistin, Haptoglobin, Mineralcorticoid releasing factor (MRF), Retinol binding protein 4, IL-1β, Monocytechemoattractant protein 1 (MCP-1), Vaspin, IL-4, Nerve growth factor (NGF), Vistafin, IL-6, Pigment epithelium derived factor (PEDF), IL-7, Prostaglandin E2, IL-8, Prostaglandin I2, IL-10, Prostaglandin 2α, IL-12, Serum transferrin, IL-18, Stromal derived factor 1, Lipocalin 24p3, TGF-β, Macrophage migration inhibitory factor 1, TIMP-1, TIMP-2, Serum amyloid A3 (SAA3), Tissue factor, TNF-α, and VEGF.

The term "hard tissue" as used herein refers to a tissue that has become mineralized, or having a firm intercellular substance, for example, cartilage and bone. In dentistry, the term is used to denote any of the three calcified tissue components of the tooth: enamel, dentin and cementum.

The term "interleukin" as used herein refers to a cytokine secreted by white blood cells as a means of communication with other white blood cells.

The term "implant" refers to any device or material inserted or placed, permanently or temporarily, into or onto a subject as well as those used for the administration or delivery of a therapeutic agent(s) or substance, or refers to the act of implanting such a device or material. The term "implantation" as used herein refers to the process of placing an implant within the body.

The term "improve" (or "improving") as used herein refers to bring into a more desirable or excellent condition.

The terms "in the body", "void volume", "resection pocket", "excavation", "injection site", "deposition site" or "implant site" as used herein are meant to include all tissues of the body without limitation, and may refer to spaces formed therein from injections, surgical incisions, tumor or tissue removal, tissue injuries, abscess formation, or any other similar cavity, space, or pocket formed thus by action of clinical assessment, treatment or physiologic response to disease or pathology as non-limiting examples thereof.

The term "indicator" as used herein refers to any substance, number, or ratio derived from a series of observed facts that may reveal relative changes as a function of time; or a signal, sign, mark, note, or symptom that is visible or evidence of the existence or presence thereof.

The term "injury" as used herein refers to damage or harm to a structure or function of the body caused by an outside agent or force, which may be physical or chemical.

The term "isolate" and its various grammatical forms as used herein refers to placing, setting apart, or obtaining a protein, molecule, substance, nucleic acid, peptide, cell, or particle, in a form essentially free from contaminants or other materials with which it is commonly associated, separate from its natural environment.

The terms "marker" or "cell surface marker" are used interchangeably herein to refer to an antigenic determinant or epitope found on the surface of a specific type of cell. Cell surface markers can facilitate the characterization of a cell type, its identification, and eventually its isolation. Cell sorting techniques are based on cellular biomarkers where a cell surface marker(s) may be used for either positive selection or negative selection, i.e., for inclusion or exclusion, from a cell population.

The term "matrix" refers to a surrounding substance within which something is contained or embedded.

The term "mesenchymal stem cells" or "MSCs" as used herein refers to non-blood adult stem cells found in a variety of tissues. They are characterized by their spindle-shape morphologically, by the expression of specific markers on their cell surface, and by their ability, under appropriate conditions, to differentiate along a minimum of three lineages (osteogenic, chondrogenic, and adipogenic). When referring to bone or cartilage, MSCs commonly are known as osteochondrogenic, osteogenic, or chondrogenic, since a single MSC has shown the ability to differentiate into chondrocytes or osteoblasts, depending on the medium. MSCs secrete many biologically important molecules, including interleukins 6, 7, 8, 11, 12, 14, and 15, M-CSF, Flt-3 ligand, SCF, LIF, bFGF, VEGF, P1GF and MCP1 (Majumdar, et al., J. Cell Physiol. 176:57-66 (1998); Kinnaird et al., Circulation 109:1543-49 (2004)). There is general agreement that MSCs lack typical hematopoietic antigens, namely CD14, CD34, and CD45. (Pittenger et al., Science 284:143-47 (1999)).

The term "mill", and its various grammatical forms, as used herein refers a process of grinding, cutting, shredding, chipping, or pulverizing a substance.

The term "mucosa" as used herein refers to a mucous tissue lining various tubular structures consisting of epithelium, lamina propria, and, in the digestive tract, a layer of smooth muscle.

The term "mucosal graft" as used herein refers to a graft of mucus membrane.

The term "multipotent" as used herein refers to a cell capable of giving rise to a limited number of cell types of a particular cell line.

The term "myogenic" refers to a potential of undifferentiated precursor cells to differentiate into a muscle forming or myocompetent cells.

The term "odontoblasts" as used herein refers to tall columnar cells of pulp derived from ectomesenchymal cells of neural crest origin. Odontoblasts form dentin and express dentin matrix protein 1 (DMP-1) and Dentin sialophosphoprotein (DSPP).

The term "osteoblasts" as used herein refers to cells that arise when osteoprogenitor cells or mesenchymal cells, which are located near all bony surfaces and within the bone marrow, differentiate under the influence of growth factors. Osteoblasts, which are responsible for bone matrix synthesis, secrete a collagen rich ground substance essential for later mineralization of hydroxyapatite and other crystals, called osteoid. Osteoblasts cause calcium salts and phosphorus to precipitate from the blood, which bond with the newly formed osteoid to mineralize the bone tissue. Once osteoblasts become trapped in the matrix they secrete, they become osteocytes. From least to terminally differentiated, the osteocyte lineage is (i) Colony-forming unit-fibroblast (CFU-F); (ii) mesenchymal stem cell/marrow stromal cell (MSC); (iii) osteoblast; and (iv) osteocyte.

The term "osteoclast" as used herein refers to large multinucleate cells associated with areas of bone resorption (breakdown).

The term "osteoconduction" as used herein refers to a process by which bone is directed so as to conform to a material's surface. An osteoconductive environment facilitates the spontaneous formation of bone. An osteoconductive surface is one that permits bone growth on its surface or down into pores, channels, or pipes. Osteoconductive material facilitates the spontaneous formation of bone by furnishing a microenvironment that supports the ingrowth of blood vessels, perivascular tissue, and osteoprogenitor cells into the site where it is deposited. Examples of osteoconductive materials, include, without limitation, the particulate granular matrix of the described invention.

The term "osteoconductive matrix" as used herein refers to a matrix that is inert in and of itself but on which cells can climb and grow bone. According to some embodiments, the particulate granular matrix of the described invention is an osteoconductive matrix, The term "osteogenic" refers to a potential of undifferentiated precursor cells to differentiate into bone forming or osteocompetent cells.

The term "osteogenesis" as used herein refers to the development or formation of new bone by bone forming or osteocompetent cells.

The term "osteoinduction" as used herein refers to a process by which primitive, undifferentiated, and pluripotent cells are stimulated to develop into a bone forming cell lineage thereby inducing osteogenesis. For example, the majority of bone healing in a fracture is dependent on osteoinduction. Osteoinductive materials can be generated by combining a porous scaffold with osteogenic cells and/or osteoinductive components, including, but are not limited to, growth factors such as BMP-2 and 4, VEGF, bFGF, TGF-β, and PDGF.

The term "osteoinductive matrix" as used herein refers to a matrix containing a substance or substances that recruit local cells to induce (meaning to cause, bring about, bring about, or trigger) local cells to produce bone.

The terms "osteoinductive components" and "osteogenic factors" are used interchangeably to refer to the plethora of mediators associated with bone development and repair, including, but not limited to, bone morphogenic proteins (BMPs), vascular endothelial growth factor (VEGF), basic fibroblast growth factor (bFGF), transforming growth factor beta (TGF-β), and platelet-derived growth factor (PDGF).

The term "osteointegration" refers to an anchorage mechanism whereby nonvital components can be incorporated reliably into living bone and that persist under all normal conditions of loading.

As used herein, the terms "osteoprogenitor cells," "mesenchymal cells," "mesenchymal stem cells (MSC)," or "marrow stromal cells" are used interchangeably to refer to multipotent stem cells that differentiate from CFU-F cells capable of differentiating along several lineage pathways into osteoblasts, chondrocytes, myocytes and adipocytes. When referring to bone or cartilage, MSCs commonly are known as osteochondrogenic, osteogenic, chondrogenic, or osteoprogenitor cells, since a single MSC has shown the ability to differentiate into chondrocytes or osteoblasts, depending on the medium.

The term "particle" as used herein refers to a piece, chip, fragment, slice, or small constituent of a larger body (e.g., picoparticles, nanoparticles, microparticles, milliparticle, centiparticle, deciparticle; fractions thereof, or, in some instances, a larger segment or piece).

The term "peptide" is used herein to refer to two or more amino acids joined by a peptide bond.

The term "periosteum" as used herein refers to the normal investment of bone, consisting of a dense, fibrous outer layer, to which muscles attach, and a more delicate, inner layer capable of forming bone.

Platelets (thrombocytes), a nucleate discoid-shaped cell fragments generated from large (50 to 100 μm in diameter) multinucleated (up to 128 N) megakaryocytes (MK), play a central role in hemostasis (meaning the stoppage of blood loss at sites of vascular injury) and vascular repair. Principles of Tissue Engineering, 4th Ed., Robert Lanza, Robert Langer, Joseph Vacanti, Eds, Elsevier, Inc.: New York, 2014 at 1047-1048. They represent about $3 \times 10^{11}$ cells/liter in peripheral blood, i.e., second only to those of RBCs. Platelets have a short life span, lasting only 7-9 days in the circulation.

Primary hemostasis is achieved through a synergistic network of receptor/ligand interactions that result in platelet adhesion and simultaneous platelet activation, platelet secretion to activate nearby platelets, platelet aggregation, and ultimately formation of a platelet plug and generation of a surface amenable to assembly of coagulation factor complexes. Haley, K M et al, "Neonatal platelets: mediators of primary hemostasis in the developing hemostatic system," Pediatr. Res. 2014; 76(3): 230-37.

Platelet a granules contain several different growth factors, including platelet-derived growth factors (PDGF-AA, PDGF-BB, BDGF-AB), transforming growth factor-β (TGF-β1 and TGF-β2), fibroblast growth factor (FGF), vascular endothelial growth factor (VEGF), epithelial growth factor (EGF), and insulin-like growth factor-1 (IGF-1), which are actively secreted by platelets (Aghideh, A N et al, "Platelet growth factors suppress ex vivo expansion and enhance differentiation of umbilical cord blood CD133+ stem cells to megakaryocyte progenitor cells," Growth Factors 2010; 28(6): 409-16, citing Martieau, I., et al, "Effects of calcium and thrombin on growth factor release from platelet concentrates: kinetics and regulation of endothelial cell proliferation," Biomaterials 2004; 25: 4489-4502).

The term "platelet-rich fibrin (PRF) as used herein refers to a matrix of autologous fibrin in which platelet cytokines, growth factors and cells are trapped. (See Agrawal, M., Agrawal, V., "Platelet Rich Fibrin and its applications in dentistry—a review article," Natl J. Med. Dent. Res. (2014) 2(3): 51-58; Gupta, V. et al, "Regenerative potential of platelet rich fibrin in dentistry: literature review. AJOHAS (2011) 1 (1): 22-28). The classic technique for preparation of PRF is as follows: a blood sample is collected without anticoagulants, which is immediately centrifuged on a table-top centrifuge at 3,000 rpm for 10 minutes to obtain three layers. The topmost layer consists of acellular platelet poor plasma (PPP); the second layer is the PRF clot; the third layer are the RBCs at the bottom of the test tube. The PRF clot is removed with sterile tweezers and separated from the underlying RBC layer with scissors, transferred on a sterile dish and stored at 4 C.

The term "platelet-rich plasma (PRP)" also referred to as "autologous platelet gel, plasma rich in growth factors (PGRF) or platelet concentrate (PC) as used herein refers to an increased concentration of autologous platelets suspended in a small amount of plasma after centrifugation. Briefly, a patient's blood is collected and centrifuged at varying speeds until it separates into three layers: platelet poor plasma (PPP); PRP; and red blood cells. Usually, two spins are used. A first hard spin separates the platelet poor plasma from the red fraction and PRP. The second soft spin separates the red fraction from the PRP. The material with the highest specific gravity (PRP) will be deposited at the bottom of the tube. Immediately before application, a platelet activator/agonist (e.g., thrombin and 10% calcium chloride) is added to activate the clotting cascade, producing a platelet gel. The process produces a platelet concentration of three to five times that of native plasma. (Marx, R E, et al, "Platelet-rich plasma: growth factor enhancement for bond grafts," Oral Surg. Oral Med. Oral Pathol. Oral Radiol. Endod. (1998) 85: 638-646; Petrungaro, P S, "Using platelet-rich plasma to accelerate soft tissue maturation in esthetic periodontal surgery," Compend. Contin. Edu. Dent. (2001) 22: 729-736).

The term "pluripotent" as used herein refers to the ability to develop into multiple cells types, including all three embryonic lineages, forming the body organs, nervous system, skin, muscle, and skeleton. A "pluripotent stem cell" or "pluripotent cell" is a cell that has the ability under appropriate conditions of producing progeny of several different cell types that are derivatives of all of the three germinal layers (endoderm, mesoderm, and ectoderm). Examples of pluripotent stem cells are embryonic stem (ES) cells, embryonic germ stem (EG) cells, embryonic Carcinoma (EC) cells, induced pluripotent stem (iPS) cells, and adult stem cells. PSCs cells may be derived from any organism of interest, including, primate, e.g., human, canine, feline, murine, equine, porcine, avian, camel, bovine, ovine, etc.

The term "progenitor cell" as used herein refers to an early descendant of a stem cell that can only differentiate, but can no longer renew itself. Progenitor cells mature into precursor cells that mature into mature phenotypes. Hematopoietic progenitor cells are referred to as colony-forming units (CFU) or colony-forming cells (CFC). The specific lineage of a progenitor cell is indicated by a suffix, such as, but not limited to, CFU-E (erythrocytic), CFU-F (fibroblastic), CFU-GM (granulocytic/macrophage), and CFU-GEMM (pluripotent hematopoietic progenitor). Osteoclasts arise from hematopoietic cells of the monocyte/neutrophil lineage (CFU-GM). Osteoprogenitor cells arise from mesenchymal stem cells and are committed to an osteocyte lineage.

The term "propagate" as used herein refers to reproduce, multiply, or to increase in number, amount, or extent by any process.

The term "pulp" as used herein refers to the connective, vascular, lymphatic, and nervous tissues occupying a chamber in the center of a tooth. Pulp is derived from proliferation and condensation of neural crest cells, which leads to the formation of dental papilla. The lateral portions of pulp contain peripheral odontoblasts and the sub-odontoblastic Hoehl's cell layer. The ECM of pulp contains, inter alia, fibronectin; collagen types I, III, V, and VI; dentin sialophosphoprotein (DSPP); dentin matrix protein 1 (DMP1); bone sialoprotein; osteopontin; matrix extracellular phosphoglycoprotein (MEPE); osteocalcin; osteonectin; tenascin; versican; hepatocyte growth factor; FGF-2; TGF-β; TNF-α; BMP2; and lymphocyte enhancer-binding factor 1 (LEF1).

The term "purification" as used herein refers to a process of isolating or freeing from foreign, extraneous, or objectionable elements so that the proportion of the desired substance or material is increased (enriched) relative to the starting material.

The term "reduced" or "to reduce" as used herein refers to a diminishing, a decrease in, an attenuation, or abatement of the degree, intensity, extent, size, amount, density, or number of.

The term "regeneration" or "regenerate" as used herein refers to a process of recreation, reconstitution, renewal, revival, restoration, differentiation, and growth to form a tissue with characteristics that conform with a natural counterpart of the tissue.

The term "relative" as used herein refers to something having, or standing in, some significant association to something else. The term "relative frequency" as used herein refer to the rate of occurrence of something having or standing in some significant association to the rate of occurrence of something else. For example, two cell types, X cells and Y cells occupy a given location. There are 5 X cells and 5 Y cells in that location. The relative frequency of cell type X is 5/10; the relative frequency of cell type Y is 5/10 in that location. Following processing, there are 5 X cells, but only 1 Y cell in that location. The relative frequency of cell type X following processing is 5/6, and the relative frequency of cell type Y following processing is 1/6 in that location.

The term "repair" as used herein as a noun refers to any correction, reinforcement, reconditioning, remedy, making up for, making sound, renewal, mending, patching, or the like that restores function. When used as a verb, it means to correct, to reinforce, to recondition, to remedy, to make up for, to make sound, to renew, to mend, to patch, or to otherwise restore function. According to some embodiments, "repair" includes full repair and partial repair.

The term "resident", and its various grammatical forms, as used herein refers to being present habitually, existing in or intrinsic to, or incorporated therein.

The term "reticular fibers" as used herein refers to small, branching fibers secreted by reticular cells. Reticular fibers frequently form a netlike supporting framework or reticulum that stain black after silver impregnation.

The term "scaffold" as used herein refers to a structure capable of supporting a three-dimensional tissue formation. A three-dimensional scaffold is believed to be critical to replicate the in vivo milieu and to allow the cells to influence their own microenvironment. Scaffolds may serve to promote cell attachment and migration, to deliver and retain cells and biochemical factors, to enable diffusion of vital cell nutrients and expressed products, and to exert certain mechanical and biological influences to modify the behavior of the cell phase. A scaffold utilized for tissue reconstruction has several requisites. Such a scaffold should have a high porosity and an adequate pore size to facilitate cell seeding and diffusion of both cells and nutrients throughout the whole structure. Biodegradability of the scaffold is also an essential requisite. The scaffold should be absorbed by the surrounding tissues without the necessity of a surgical removal, such that the rate at which degradation occurs coincides as closely as possible with the rate of tissue formation. As cells are fabricating their own natural matrix structure around themselves, the scaffold provides structural integrity within the body and eventually degrades leaving the neotissue (newly formed tissue) to assume the mechanical load.

The term "similar" is used interchangeably with the terms analogous, comparable, or resembling, meaning having traits or characteristics in common.

The term "soft tissue" as used herein refers to tissues that connect, support, or surround other structures and organs of the body. Soft tissue includes muscles, tendons, ligaments, fascia, nerves, fibrous tissues, fat, blood vessels, and synovial membranes. It gives shape to and supports the body, protects other body tissues and structures, and hold them together.

A "solution" generally is considered as a homogeneous mixture of two or more substances. It is frequently, though not necessarily, a liquid. In a solution, the molecules of the solute (or dissolved substance) are uniformly distributed among those of the solvent.

The term "solvent" as used herein refers to a substance capable of dissolving another substance (termed a "solute") to form a uniformly dispersed mixture (solution).

The term "stem cells" refers to undifferentiated cells having high proliferative potential with the ability to self-renew that can generate daughter cells that can undergo terminal differentiation into more than one distinct cell phenotype.

The term "stimulate" as used herein refers to activate, provoke, or spur. The term "stimulating agent" as used herein refers to a substance that exerts some force or effect.

The term "subject in need thereof" as used herein refers to a patient that (i) will be administered at least one graft; (ii) ire receiving at least one graft; or (iii) has received at least one graft, unless the context and usage of the phrase indicates otherwise.

The term "substantially freer" as used herein means that a first value, aspect, trait, feature, number, or amount is of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of a second value, aspect, trait, feature, number, or amount, or that the first value, aspect, trait, feature, number or amount. contains less than 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4$, 3%, 2%, or 1% of the second value, aspect, trait, feature, number or amount.

The term "saturation" and its various grammatical forms as used herein mean the state of a carrier matrix when it holds the maximum equilibrium quantity of cells at a given temperature and pressure.

The term "supersaturation" and its various grammatical forms as used herein mean a condition in which a carrier matrix contains more cells than are present in a saturated condition of the same components at equivalent temperature and pressure.

The term "symptom" as used herein refers to a sign or an indication of disorder or disease, especially when experienced by an individual as a change from normal function, sensation, or appearance.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect also may include, directly or indirectly, the arrest reduction or elimination of the progression of a disease manifestation.

The term "tooth demineralization" or "tooth erosion" as used herein refers to the wearing away or destruction (erosion) of tooth enamel. This erosion may be caused by any number of factors, including bacterial infection, teeth grinding, abrasion, and abfraction (meaning an angular notch at the gumline caused by bending forces applied to the tooth).

The term "tooth resorption" as used herein refers to a process by which all or part of a tooth structure is lost. In "external resorption" the root surface is lost; this can be caused, for example, by chronic inflammation, cysts, tumors, trauma, reimplantation of a tooth, or by unknown causes. "Internal resorption" involves resorption of dentin and pulpal walls centrally within the root canal; the cause can sometimes be attributed to tooth trauma, but often there is no known cause.

The term "transforming growth factor beta (TGFβ) signaling pathway" is used herein to refer to the signaling pathway is involved in many cellular processes in both the adult organism and the developing embryo including cell growth, cell differentiation, apoptosis, cellular homeostasis, and other cellular functions. TGFβ superfamily ligands bind to a type II receptor, which recruits and phosphorylates a type I receptor. The type I receptor then phosphorylates receptor-regulated SMADs (R-SMADs) which can now bind the coSMAD SMAD4. R-SMAD/coSMAD complexes accumulate in the nucleus where they act as transcription factors and participate in the regulation of target gene expression.

The term "treat" or "treating" includes abrogating, substantially inhibiting, slowing, or reversing the progression of a disease, condition, or disorder; substantially ameliorating clinical or esthetical symptoms of a condition; substantially preventing the appearance of clinical or esthetical symptoms of a disease, condition, or disorder; and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "vascularization" as used herein refers to a process of ingrowth of blood vessels and perivascular tissue within a growth-conductive matrix to support the deposition and adhesion of cells with the potential to differentiate into a mature cell type to effect tissue regeneration.

The term "viable" as used herein refers to having the ability to grow, expand and develop.

1. Implant or Graft

The described invention provides graft products for implantation for the repair and regeneration of hard tissue and soft tissue.

Each product comprises one or more three dimensional scaffold/carrier matrix, a growth factor composition, and one or more cell compositions.

1.1 Three-Dimensional Carrier Matrix

According to some embodiments where hard tissue grafts are desired, the three-dimensional carrier matrix can comprise aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, α-tricalcium phosphate, dicalcium phosphate, β-tricalcium phosphate, tetracalcium phosphate, amorphous calcium phosphate, octacalcium phosphate, Bioglass® (borosilicate glass), fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), coral, silicate or silicate derived materials, or combinations or derivatives thereof.

According to some embodiments, the three-dimensional carrier matrix for hard tissue grafts can comprise a collagen. According to some embodiments, the collagen can comprise one or more of type I collagen, fibrillary Type II, III, and V collagen, and type IV collagen. According to some embodiments, the collagen is human. According to some embodiments, the collagen is bovine. According to some embodiments, the scaffold/carrier matrix comprises a synthetic collagen. According to some embodiments the synthetic collagen is one or more of synthetic type I, type II, type III, type IV, or type V collagen. According to some embodiments, the one or more synthetic type 1, type II, type III, type V or type IV collagen is human. According to some embodiments, the on or more synthetic type I, type II, III, type V or type IV collagen is bovine.

According to some embodiments, the scaffold/carrier matrix comprises a natural collagen matrix.

According to some embodiments, the three-dimensional carrier matrix for hard tissue grafts can comprise tri-calcium phosphate (α-tricalcium phosphate and/or β-tricalcium phosphate).

According to some embodiments, the three-dimensional carrier matrix for hard tissue grafts can comprise de-mineralized bone. According to some embodiments, the demineralized bone can be in form of strips. According to some embodiments, the demineralized bone can be in form of demineralized bone particles [need dimensions].

According to some embodiments, the three-dimensional carrier matrix for hard tissue grafts can comprise dentin. According to some such embodiments the dentin is prepared by autologous extraction from the pulp and core of vital teeth. According to some embodiments, the dentin is granular. According to some embodiments, the dentin is hydrated.

According to some embodiments, the three-dimensional carrier matrix for hard tissue grafts can comprise amnion membrane, chorion membrane or both amnionchorion membrane. According to some such embodiments, the membrane is intact. According to some such embodiments, the membrane is dehydrated. According to some such embodiments, the membrane is fresh. According to some such embodiments, the membrane is morcellized, meaning prepared as small bits or portions.

Thus, according to some embodiments, the three-dimensional carrier matrix can comprise morcelized amnion membrane in addition to one or more collagens selected from type I, type II, type III, type V, or type IV collagen, tri-calcium phosphate, de-mineralized bone strips, de-mineralized bone particles, or dentin. According to some embodiments, the three-dimensional carrier matrix can comprise morcelized chorion membrane in addition to one or more collagen selected from type I, type II, type III, type V, or type IV collagen, tri-calcium phosphate, de-mineralized bone strips, de-mineralized bone particles, or dentin. According to some embodiments, the three-dimensional carrier matrix can comprise morcelized amnionchorion membrane in addition to one or more collagen selected from type I, type II, type III, type V, or type IV collagen, tri-calcium phosphate, de-mineralized bone strips, de-mineralized bone particles, or dentin.

Three-dimensional carrier matrices for hard tissues can be produced, e.g., as described in US20160000974, the entire contents of which are incorporated herein by reference. For example, the three-dimensional carrier matrices can be prepared with a single polymer or blended polymers. Exemplary polymers include poly(α-hydroxy acids), such as the polyesters, polylactic acid (PLA), poly L-lactic acid (PLLA), polyglycolic acid (PGA), polylactic co-glycolic acid (PLGA), poly ε-caprolactone (PCL), poly methacrylate co-n-butyl methacrylate (PMMA), polydimethylsiloxane (PDMS), and polyethylene oxide (PEO). Polymer blending can be used to increase or decrease the degradation time of a matrix. For example, PCL degrades more slowly (1-1.5 years) than PGA (three months) and the rate of degradation can be adjusted by using a blended combination of these polymers to form the matrix. The matrices can have a final total concentration of polymer of about 5%-30%, e.g., 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%.

Suitable nanoceramics include, but are not limited to, hydroxyapatite, tricalcium phosphate, biphasic calcium phosphate, calcium carbonate, calcium sulfate, bioactive glass, and biphasic bioceramics. A matrix may contain one or more nanoceramics.

Three-dimensional carrier matrices can be prepared from a matrix solution by electrospinning or solvent casting. The matrix solution comprises any of the aforementioned compounds in any combination. To produce the matrix solution, for example, the polymer(s) is added to an appropriate solvent and the nanoceramic(s) is subsequently added, if present, to form a matrix solution. Appropriate solvents for specific polymers are known in the art and include methylene chloride (MC), 1,1,1,3,3,3-hexafluoro-2-propanol (HFIP), acetone, chloroform, dimethyl formamide (DMF), tetrahydrofuran (THF), and ethyl acetate.

According to some embodiments where soft tissue grafts are desired, the three-dimensional carrier matrix comprises physiologically-compatible and optionally biodegradable polymers. Examples of polymers that are employable in the devices are known in the art (see, e.g., US2011/0020216, incorporated herein by reference in its entirety). Representative examples of such polymers include, but are not limited to, poly(lactide)s, poly(glycolide)s, poly(lactic acid)s, poly(glycolic acid)s, polyanhydrides, polyorthoesters, polyetheresters, polycaprolactones, polyesteramides, polycarbonates, polycyanoacrylates, polyurethanes, polyacrylates, and blends or copolymers thereof. Biodegradable scaffolds may comprise biodegradable materials, e.g., one or more collagen selected from a, Type I collagen, a Type II collagen, a Type III collagen, a type V collagen, or a type 4 collagen, alginates, polysaccharides, polyethylene glycol (PEG), poly(glycolide) (PGA), poly(L-lactide) (PLA), or poly(lactide-co-glycolide) (PLGA) or silk. According to some embodiments, the three-dimensional carrier matrix comprises a biocompatible polymer matrix that is wholly or partly biodegradable. A hydrogel is one example of a suitable polymer matrix material. Examples of materials which can form hydrogels include polylactic acid, polyglycolic acid, PLGA polymers, alginates and alginate derivatives, gelatin, one or more collagen (e.g., a type I collagen, a fibrillary collagen (e.g., selected from types II, III, and V, or a type IV collagen), agarose, natural and synthetic polysaccharides, polyamino acids such as polypeptides particularly poly(lysine), polyesters such as polyhydroxybutyrate and poly-ε-caprolactone, polyanhydrides; polyphosphazines, poly(vinyl alcohols), poly(alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers. According to another embodiment, the three-dimensional carrier matrix may be fabricated from a variety of synthetic polymers and naturally-occurring polymers such as, but not limited to, one or more collagen (e.g., a type I collagen, a fibrillary collagen (e.g., selected from types II, III, and V), or a type IV collagen), fibrin, hyaluronic acid, agarose, and laminin-rich gels. In the case of biodegradable structures, the composition is degraded by physical or chemical action, e.g., level of hydration, heat or ion exchange or by cellular action, e.g., elaboration of enzyme, peptides, or other compounds by nearby or resident cells. The consistency varies from a soft/pliable (e.g., a gel) to glassy, rubbery, brittle, tough, elastic, stiff. The structures contain pores, which are nanoporous, microporous, or macroporous, and the pattern of the pores is optionally homogeneous, heterogeneous, aligned, repeating, or random.

According to some embodiments, the polymers are hydrogel-forming agents, e.g., glycolides and/or alginates. Alginates are versatile polysaccharide based polymers that may be formulated for specific applications by controlling the molecular weight, rate of degradation and method of scaffold formation. Coupling reactions can be used to covalently attach bioactive epitopes, such as the cell adhesion sequence RGD to the polymer backbone. Glycolide/alginate polymers can be formed into a variety of scaffold types. Injectable hydrogels can be formed from low MW alginate solutions upon addition of a cross-linking agents, such as calcium ions, while macroporous scaffolds are formed by lyophilization of high MW alginate discs. Differences in three-dimensional carrier matrix formulation control the kinetics of three-dimensional carrier matrix degradation. Release rates of morphogens or other bioactive substances from alginate three-dimensional carrier matrices is controlled by three-dimensional carrier matrix formulation to present morphogens in a spatially and temporally controlled manner. This controlled release not only eliminates systemic side effects and the need for multiple injections, but can be used to create a microenvironment that activates host cells at the implant site and transplanted cells seeded onto a three-dimensional carrier matrix.

Methods for fabricating a three-dimensional carrier matrix compositions have been described (See, e.g., Martinsen et al., Biotech. Bioeng. 33:79-89 (1989), Matthew et al., Biomaterials 16:265-74 (1995), Atala et al., J. Urology 152:641-43 (1994), and Smidsrod, TIBTECH 8:71-78 (1990), the disclosure of each reference is incorporated by reference herein in its entirety. For example, in some embodiments, a three-dimensional carrier matrix can be fabricated by suspending an aqueous solution of the matrix polymer in distilled water or a buffer followed by sterilization of the suspension by, e.g., autoclaving and/or filtration. The sterile suspension is then mixed with the cell culture composition and/or growth factor composition, with the resultant composition formed into gel beads, e.g., by dripping the composition from a syringe into a calcium chloride solution followed by hardening period, e.g., 5, 10, 20, 30 or minutes depending on the size of the gel beads. In some embodiments, cells and/or growth factors can be recovered from the three-dimensional carrier matrix by gentle dissolution of the gel beads by immersing the beads in a phosphate or citrate solution.

According to some embodiments where soft tissue grafts are desired, the three-dimensional carrier matrix can comprise one or more of a collagen (e.g., a type I collagen, a fibrillary collagen selected from types II, III, and V, or a type IV collagen)), a fibrin gel, a fibrin membrane, a fibrin matrix, hyaluronic acid, an amnion membrane (e.g., a morcelized amnion membrane), a chorion membrane, an amnion/chorion three dimensional matrixs, a PLA mesh, a PLA membrane, a PLGA membrane, a PLGA mesh, a PLA/PGLA mesh, a PLA/PGLA membrane, a PLA mesh/PGLA membrane, and a PLA membrane/PGLA mesh.

According to some such embodiments of the soft tissue graft, the three dimensional carrier matrix comprises collagen. According to some such embodiments, the three dimensional carrier matrix comprises fibrin gel. According to some such embodiments, the three dimensional carrier matrix comprises fibrin membrane. According to some such embodiments, the three dimensional carrier matrix comprises amnion membrane. According to some such embodiments, the three dimensional carrier matrix comprises chorion membrane. According to some such embodiments, the three dimensional carrier matrix comprises PLA mesh. According to some such embodiments, the three dimensional carrier matrix comprises PLA membrane. According to some such embodiments, the three dimensional carrier matrix comprises PLGA membrane. According to some such embodiments, the three dimensional carrier matrix comprises PLGA mesh. According to some such embodiments, the three dimensional carrier matrix comprises PLA/PGLA mesh. According to some such embodiments, the three dimensional carrier matrix comprises PLA/PLGA membrane. According to some such embodiments, the three dimensional carrier matrix comprises PLA mesh/PLGA membrane. According to some such embodiments, the three dimensional carrier matrix comprises PLA membrane/PLGA mesh.

Thus, the three-dimensional carrier matrix can comprise collagen, fibrin gel, fibrin membrane, amnion membrane, chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; collagen and fibrin gel, fibrin membrane, amnion membrane, chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; fibrin gel and fibrin membrane, amnion membrane, chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; fibrin membrane and amnion membrane, chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; amnion membrane and chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; chorion membrane and PLA mesh, PLA membrane, PLGA membrane, PLGA mesh, PLA/PGLA mesh, PLA/PGLA membrane, PLA mesh/PGLA membrane, or PLA membrane/PGLA mesh; collagen and fibrin gel and fibrin membrane, amnion membrane, chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; collagen and fibrin membrane and amnion membrane, chorion membrane, PLA mesh, PLA membrane, PLGA membrane, PLGA mesh, PLA/PGLA membrane, PLA mesh/PGLA membrane, or PLA membrane/PGLA mesh; collagen and amnion membrane and chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; collagen and chorion membrane and PLA mesh, PLA membrane, PLGA membrane, PLGA mesh, PLA/PGLA mesh, PLA/PGLA membrane, PLA mesh/PGLA membrane, or PLA membrane/PGLA mesh; fibrin gel and fibrin membrane and amnion membrane, chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; fibrin gel and amnion membrane and chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; fibrin gel and chorion membrane and PLA mesh, PLA membrane, PLGA membrane, PLGA mesh, PLA/PGLA mesh, PLA/PGLA membrane, PLA mesh/PGLA membrane, or PLA membrane/PGLA mesh; fibrin membrane and amnion membrane and chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; fibrin membrane and chorion membrane and PLA mesh, PLA membrane, PLGA membrane, PLGA mesh, PLA/PGLA mesh, PLA/PGLA membrane, PLA mesh/PGLA membrane, or PLA membrane/PGLA mesh; amnion membrane and chorion membrane and PLA mesh, PLA membrane, PLGA membrane, PLGA mesh, PLA/PGLA mesh, PLA/PGLA membrane, PLA mesh/PGLA membrane, or PLA membrane/PGLA mesh; collagen, fibrin gel, and fibrin membrane and amnion membrane, chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; collagen, fibrin membrane, and amnion membrane and chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; collagen, amnion membrane, and chorion membrane and PLA mesh, PLA membrane, PLGA membrane, PLGA mesh, PLA/PGLA mesh, PLA/PGLA membrane, PLA mesh/PGLA membrane, or PLA membrane/PGLA mesh; fibrin gel, fibrin membrane, and amnion membrane and chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; fibrin gel, amnion membrane, and chorion membrane and PLA mesh, PLA membrane, PLGA membrane, PLGA mesh, PLA/PGLA mesh, PLA/PGLA membrane, PLA mesh/PGLA membrane, or PLA membrane/PGLA mesh; fibrin membrane, amnion membrane, and chorion membrane and PLA mesh, PLA membrane, PLGA membrane, PLGA mesh, PLA/PGLA mesh, PLA/PGLA membrane, PLA mesh/PGLA membrane, or PLA membrane/PGLA mesh; collagen, fibrin gel, fibrin membrane, and amnion membrane and chorion membrane, PLA mesh, PLA membrane, PLGA membrane, PLGA mesh, PLA/PGLA mesh, PLA/PGLA membrane, PLA mesh/PGLA membrane, or PLA membrane/PGLA mesh; collagen, fibrin membrane, amnion membrane, and chorion membrane and PLA mesh, PLA membrane, PLGA membrane, PLGA mesh, PLA/PGLA membrane, PLA mesh/PGLA membrane, or PLA membrane/PGLA mesh; or fibrin gel, fibrin membrane, amnion membrane, and chorion membrane and PLA mesh, PLA membrane, PLGA membrane, PLGA mesh, PLA/PGLA mesh, PLA/PGLA membrane, PLA mesh/PGLA membrane, or PLA membrane/PGLA mesh.

1.2 Growth Factor Composition

According to some embodiments, the growth factor composition comprises one or more of VEGF, PDGF, TGF-β, BMP-2, BMP-7, IL-1, EGF, IGF-1, fibronectin, FGF, and NELL1. Thus, the growth factor composition can comprise VEGF, PDGF, TGF-β, BMP-2, BMP-7, IL-1, EGF, IGF-1, fibronectin, FGF, or NELL1; VEGF and PDGF, TGF-β, BMP-2, BMP-7, IL-1, EGF, IGF-1, fibronectin, FGF, or NELL1; PDGF and TGF-β, BMP-2, BMP-7, IL-1, EGF, IGF-1, fibronectin, FGF, or NELL1; TGF-β and BMP-2, BMP-7, IL-1, EGF, IGF-1, fibronectin, FGF, or NELL1; BMP-2 and BMP-7, IL-1, EGF, IGF-1, fibronectin, FGF, or NELL1; BMP-7 and IL-1, EGF, IGF-1, fibronectin, FGF, or NELL1; IL-1 and EGF, IGF-1, fibronectin, FGF, or NELL1; EGF and IGF-1, fibronectin, FGF, or NELL1; IGF-1 and fibronectin, FGF, or NELL1; fibronectin and FGF or NELL1; FGF and NELL1; VEGF and PDGF and TGF-β, BMP-2, BMP-7, IL-1, EGF, IGF-1, fibronectin, FGF, or NELL1; VEGF and TGF-β and BMP-2, BMP-7, IL-1, EGF, IGF-1, fibronectin, FGF, or NELL1; VEGF and BMP-2 and BMP-7, IL-1, EGF, IGF-1, fibronectin, FGF, or NELL1; VEGF and BMP-7 and IL-1, EGF, IGF-1, fibronectin, FGF, or NELL1; VEGF and IL-1 and EGF, IGF-1, fibronectin, FGF, or NELL1; VEGF and EGF and IGF-1, fibronectin, FGF, or NELL1; VEGF and IGF-1 and fibronectin, FGF, or NELL1; VEGF and fibronectin and FGF or NELL1; VEGF, FGF, and NELL1; PDGF and TGF-β and BMP-2, BMP-7, IL-1, EGF, IGF-1, fibronectin, FGF, or NELL1; PDGF and BMP-2 and BMP-7, IL-1, EGF, IGF-1, fibronectin, FGF, or NELL1; PDGF and BMP-7 and IL-1, EGF, IGF-1, fibronectin, FGF, or NELL1; PDGF and IL-1 and EGF, IGF-1, fibronectin, FGF, or NELL1; PDGF and EGF and IGF-1, fibronectin, FGF, or NELL1; PDGF and IGF-1 and fibronectin, FGF, or NELL1; PDGF and fibronectin and FGF or NELL1; PDGF, FGF, and NELL1; TGF-β and BMP-2 and BMP-7, IL-1, EGF, IGF-1, fibronectin, FGF, or NELL1; TGF-β and BMP-7 and IL-1, EGF, IGF-1, fibronectin, FGF, or NELL1; TGF-β and IL-1 and EGF, IGF-1, fibronectin, FGF, or NELL1; TGF-β and EGF and IGF-1, fibronectin, FGF, or NELL1; TGF-β and IGF-1 and fibronectin, FGF, or NELL1; TGF-β and fibronectin and FGF or NELL1; TGF-β, FGF, and NELL1; BMP-2, BMP-7, IL-1, EGF, IGF-1, fibronectin, FGF, or NELL1; BMP-2 and BMP-7 and IL-1, EGF, IGF-1, fibronectin, FGF, or NELL1; BMP-2 and IL-1 and EGF, IGF-1, fibronectin, FGF, or NELL1; BMP-2 and EGF and IGF-1, fibronectin, FGF, or NELL1; BMP-2 and IGF-1 and fibronectin, FGF, or NELL1; BMP-2 and fibronectin and FGF or NELL1; BMP-7 and IL-1 and EGF, IGF-1, fibronectin, FGF, or NELL1; BMP-7 and EGF and IGF-1, fibronectin, FGF, or NELL1; BMP-7 and IGF-1 and fibronectin, FGF, or NELL1; BMP-7 and fibronectin and FGF or NELL1; BMP-7, FGF, and NELL1; IL-1 and EGF and IGF-1, fibronectin, FGF, or NELL1; IL-1 and IGF-1 and fibronectin, FGF, or NELL1; IL-1 and fibronectin and FGF or NELL1; IL-1, FGF, and NELL1; EGF and IGF-1 and fibronectin, FGF, or NELL1; EGF and fibronectin and FGF or NELL1; EGF, FGF, and NELL1; IGF-1, and fibronectin and FGF or NELL1; IGF-1, FGF, and NELL1; fibronectin, FGF, and NELL1; VEGF, PDGF, and TGF-β and BMP-2, BMP-7, IL-1, EGF, IGF-1, fibronectin, FGF, or NELL1; VEGF, TGF-β, and BMP-2 and BMP-7, IL-1, EGF, IGF-1, fibronectin, FGF, or NELL1; VEGF, BMP-2, and BMP-7 and IL-1, EGF, IGF-1, fibronectin, FGF, or NELL1; VEGF, BMP-7, and IL-1 and EGF, IGF-1, fibronectin, FGF, or NELL1; VEGF, IL-1, and EGF and IGF-1, fibronectin, FGF, or NELL1; VEGF, EGF, and IGF-1 and fibronectin, FGF, or NELL1; VEGF, IGF-1, and fibronectin and FGF or NELL1; VEGF, fibronectin, FGF, and NELL1; PDGF, TGF-β, and BMP-2 and BMP-7, IL-1, EGF, IGF-1, fibronectin, FGF, or NELL1; PDGF, BMP-2, and BMP-7 and IL-1, EGF, IGF-1, fibronectin, FGF, or NELL1; PDGF, BMP-7, and IL-1 and EGF, IGF-1, fibronectin, FGF, or NELL1; PDGF, IL-1, and EGF and IGF-1, fibronectin, FGF, or NELL1; PDGF, EGF, and IGF-1 and fibronectin, FGF, or NELL1; PDGF, IGF-1, and fibronectin and FGF or NELL1; PDGF, fibronectin, FGF, and NELL1; TGF-β, BMP-2, and BMP-7 and IL-1, EGF, IGF-1, fibronectin, FGF, or NELL1; TGF-β, BMP-7, and IL-1 and EGF, IGF-1, fibronectin, FGF, or NELL1; TGF-β, IL-1, and EGF and IGF-1, fibronectin, FGF, or NELL1; TGF-β, EGF, and IGF-1 and fibronectin, FGF, or NELL1; TGF-β, IGF-1, and fibronectin and FGF or NELL1; TGF-β, fibronectin, FGF, and NELL1; BMP-2, BMP-7, and IL-1 and EGF, IGF-1, fibronectin, FGF, or NELL1; BMP-2, IL-1, and EGF and IGF-1, fibronectin, FGF, or NELL1; BMP-2, EGF, and IGF-1 and fibronectin, FGF, or NELL1; BMP-2, IGF-1, and fibronectin and FGF or NELL1; BMP-2, fibronectin, FGF, and NELL1; BMP-7, IL-1, and EGF and IGF-1, fibronectin, FGF, or NELL1; BMP-7, EGF, and IGF-1 and fibronectin, FGF, or NELL1; BMP-7, IGF-1, and fibronectin and FGF or NELL1; BMP-7, fibronectin, FGF, and NELL1; IL-1, EGF, and IGF-1 and fibronectin, FGF, or NELL1; IL-1, IGF-1, and fibronectin and FGF or NELL1; IL-1, fibronectin, FGF, and NELL1; EGF, IGF-1, and fibronectin and FGF or NELL1; EGF, fibronectin, FGF, and NELL1; IGF-1, fibronectin, FGF, and NELL1; VEGF, PDGF, TGF-β, and BMP-2 and BMP-7, IL-1, EGF, IGF-1, fibronectin, FGF, or NELL1; VEGF, TGF-β, BMP-2, and BMP-7 and IL-1, EGF, IGF-1, fibronectin, FGF, or NELL1; VEGF, BMP-2, BMP-7, and IL-1 and EGF, IGF-1, fibronectin, FGF, or NELL1; VEGF, BMP-7, IL-1, and EGF and IGF-1, fibronectin, FGF, or NELL1; VEGF, IL-1, EGF, and IGF-1 and fibronectin, FGF, or NELL1; VEGF, EGF, IGF-1, and fibronectin and FGF or NELL1; VEGF, IGF-1, fibronectin, FGF, and NELL1; PDGF, TGF-β, BMP-2, and BMP-7 and IL-1, EGF, IGF-1, fibronectin, FGF, or NELL1; PDGF, BMP-2, BMP-7, and IL-1 and EGF, IGF-1, fibronectin, FGF, or NELL1; PDGF, BMP-7, IL-1, and EGF and IGF-1, fibronectin, FGF, or NELL1; PDGF, IL-1, EGF, and IGF-1 and fibronectin, FGF, or NELL1; PDGF, EGF, IGF-1, and fibronectin and FGF or NELL1; PDGF, IGF-1, fibronectin, FGF, and NELL1; TGF-β, BMP-2, BMP-7, and IL-1 and EGF, IGF-1, fibronectin, FGF, or NELL1; TGF-β, BMP-7, IL-1, and EGF and IGF-1, fibronectin, FGF, or NELL1; TGF-β, IL-1, EGF, and IGF-1 and fibronectin, FGF, or NELL1; TGF-β, EGF, IGF-1, and fibronectin and FGF or NELL1; TGF-β, IGF-1, fibronectin, FGF, and NELL1; BMP-2, BMP-7, IL-1, and EGF and IGF-1, fibronectin, FGF, or NELL1; BMP-2, IL-1, EGF, and IGF-1 and fibronectin, FGF, or NELL1; BMP-2, EGF, IGF-1, and fibronectin and FGF or NELL1; BMP-2, IGF-1, fibronectin, FGF, and NELL1; BMP-7, IL-1, EGF, and IGF-1 and fibronectin, FGF, or NELL1; BMP-7, EGF, IGF-1, and fibronectin and FGF or NELL1; BMP-7, IGF-1, fibronectin, FGF, and NELL1; IL-1, EGF, IGF-1, and fibronectin and FGF or NELL1; IL-1, IGF-1, fibronectin, FGF, and NELL1; EGF, IGF-1, fibronectin, FGF, and NELL1; VEGF, PDGF, TGF-β, BMP-2, and BMP-7 and IL-1, EGF, IGF-1, fibronectin, FGF, or NELL1; VEGF, TGF-β, BMP-2, BMP-7, and IL-1 and EGF, IGF-1, fibronectin, FGF, or NELL1; VEGF, BMP-2, BMP-7, IL-1, and EGF and IGF-1, fibronectin, FGF, or NELL1; VEGF, BMP-7, IL-1, EGF, and IGF-1 and fibronectin, FGF, or NELL1; VEGF, IL-1, EGF, IGF-1, and fibronectin and FGF or NELL1; VEGF, EGF, IGF-1, fibronectin, FGF, and NELL1; PDGF, TGF-β, BMP-2, BMP-7, and IL-1 and EGF, IGF-1, fibronectin, FGF, or NELL1; PDGF, BMP-2, BMP-7, IL-1, and EGF and IGF-1, fibronectin, FGF, or NELL1; PDGF, BMP-7, IL-1, EGF, and IGF-1 and fibronectin, FGF, or NELL1; PDGF, IL-1, EGF, IGF-1, and fibronectin and FGF or NELL1; PDGF, EGF, IGF-1, fibronectin, FGF, and NELL1; TGF-β, BMP-2, BMP-7, IL-1, and EGF and IGF-1, fibronectin, FGF, or NELL1; TGF-β, BMP-7, IL-1, EGF, and IGF-1 and fibronectin, FGF, or NELL1; TGF-β, IL-1, EGF, IGF-1, and fibronectin and FGF or NELL1; TGF-β, EGF, IGF-1, fibronectin, FGF, and NELL1; BMP-2, BMP-7, IL-1, EGF, and IGF-1 and fibronectin, FGF, or NELL1; BMP-2, IL-1, EGF, IGF-1, and fibronectin and FGF or NELL1; BMP-2, EGF, IGF-1, fibronectin, FGF, and NELL1; BMP-7, IL-1, EGF, IGF-1, and fibronectin and FGF or NELL1; BMP-7, EGF, IGF-1, fibronectin, FGF, and NELL1; IL-1, EGF, IGF-1, fibronectin, FGF, and NELL1; VEGF, PDGF, TGF-β, BMP-2, BMP-7, and IL-1 and EGF, IGF-1, fibronectin, FGF, or NELL1; VEGF, TGF-β, BMP-2, BMP-7, IL-1, and EGF and IGF-1, fibronectin, FGF, or NELL1; VEGF, BMP-2, BMP-7, IL-1, EGF, and IGF-1 and fibronectin, FGF, or NELL1; VEGF, BMP-7, IL-1, EGF, IGF-1, and fibronectin and FGF or NELL1; VEGF, IL-1, EGF, IGF-1, fibronectin, FGF, and NELL1; PDGF, TGF-β, BMP-2, BMP-7, IL-1, and EGF and IGF-1, fibronectin, FGF, or NELL1; PDGF, BMP-2, BMP-7, IL-1, EGF, and IGF-1 and fibronectin, FGF, or NELL1; PDGF, BMP-7, IL-1, EGF, IGF-1, and fibronectin and FGF or NELL1; PDGF, IL-1, EGF, IGF-1, fibronectin, FGF, and NELL1; TGF-β, BMP-2, BMP-7, IL-1, EGF, and IGF-1 and fibronectin, FGF, or NELL1; TGF-β, BMP-7, IL-1, EGF, IGF-1, and fibronectin and FGF, or NELL1; TGF-β, IL-1, EGF, IGF-1, fibronectin, FGF, and NELL1; BMP-2, BMP-7, IL-1, EGF, IGF-1, and fibronectin and FGF or NELL1; BMP-2, IL-1, EGF, IGF-1, fibronectin, FGF, and NELL1; BMP-7, IL-1, EGF, IGF-1, fibronectin, FGF, and NELL1; VEGF, PDGF, TGF-β, BMP-2, BMP-7, IL-1, and EGF and IGF-1, fibronectin, FGF, or NELL1; VEGF, TGF-β, BMP-2, BMP-7, IL-1, EGF, and IGF-1 and fibronectin, FGF, or NELL1; VEGF, BMP-2, BMP-7, IL-1, EGF, IGF-1, and fibronectin and FGF or NELL1; VEGF, BMP-7, IL-1, EGF, IGF-1, fibronectin, FGF, and NELL1; PDGF, TGF-β, BMP-2, BMP-7, IL-1, EGF, and IGF-1 and fibronectin, FGF, or NELL1; PDGF, BMP-2, BMP-7, IL-1, EGF, IGF-1, and fibronectin and FGF or NELL1; PDGF, BMP-7, IL-1, EGF, IGF-1, fibronectin, FGF, and NELL1; TGF-β, BMP-2, BMP-7, IL-1, EGF, IGF-1, and fibronectin and FGF or NELL1; TGF-β, BMP-7, IL-1, EGF, IGF-1, fibronectin, FGF, and NELL1; BMP-2, BMP-7, IL-1, EGF and IGF-1 and fibronectin, FGF, or NELL1; VEGF, TGF-β, BMP-2, BMP-7, IL-1, EGF, IGF-1, and fibronectin and FGF or NELL1; VEGF, BMP-2, BMP-7, IL-1, EGF, IGF-1, fibronectin, FGF, and NELL1; PDGF, TGF-β, BMP-2, BMP-7, IL-1, EGF, IGF-1, and fibronectin and FGF or NELL1; PDGF, BMP-2, BMP-7, IL-1, EGF, IGF-1, fibronectin, FGF, and NELL1; TGF-β, BMP-2, BMP-7, IL-1, EGF, IGF-1, fibronectin, FGF, and NELL1; PDGF, TGF-β, BMP-2, BMP-7, IL-1, EGF, IGF-1, fibronectin, FGF, and NELL1; or VEGF, PDGF, TGF-β, BMP-2, BMP-7, IL-1, EGF, IGF-1, fibronectin, FGF, and NELL1.

According to some aspects, the growth factor composition is derived from a blood product from a subject. For example, the blood product can be whole blood, plasma, platelet-rich plasma, platelet-poor plasma, platelet-rich fibrin, or a combination thereof.

Blood can be collected in any suitable manner, including, without limitation, by having blood drawn (e.g., with a syringe or other vessel comprising a blood thinner (such as heparin), an anticoagulant (e.g., citrate dextrose ("ACDA") or buffered trisodium citrate), and/or any other suitable material) from the subject and/or one or more other individuals, and then extracting plasma (e.g., PRP, concentrated plasma, plasma, platelet concentrate, super concentrated plasma, growth factors, and/or any other suitable form of plasma and/or other materials) from the blood. In this regard, the plasma (e.g., PRP, concentrated plasma, etc.) can be extracted from collected blood in any suitable manner. Some examples of suitable methods for extracting plasma include, but are not limited to, the use of conventional plasma extraction kits (e.g., a plasma and serum preparation kit provided by Life Technologies of Grand Island N.Y., USA), a plasma concentration kit (e.g., a PLASMAX® and/or a PLASMAX® Plus plasma concentration system, produced by Biomet Biologics, LLC of Warsaw, Ind., USA); a Harvest PRP kit, produced by Harvest Technologies, Corp. of Plymouth, Mass., USA; etc.), centrifugation of whole blood and collecting the plasma supernatant, centrifugation of plasma supernatant to obtain platelet concentrate, and/or any other technique. According to some embodiments, however, a plasma concentration kit is used to obtain PRP and plasma that is relatively rich with growth factors.

Plasma can be concentrated to any suitable concentration, including, without limitation, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more times more concentrated than it was in the blood from which the plasma is obtained (including with any blood thinner and/or other materials used in the collection process).

According to some embodiments, the growth factor composition comprises platelet rich fibrin (PRF). According to some embodiments the growth composition comprises an autologous re-calcified liquid platelet-rich plasma (PRP). Exemplary platelet plasma products are disclosed in U.S. Pat. Nos. 6,214,338; 6,010,627; 5,165,928; 6,303,112; 6,979,307; and 6,649,072, and Published U.S. Patent Application Nos. 2004/0071786 and 2006/0128016, each of which is incorporated herein by reference in its entirety. The more concentrated the platelets are in the plasma, the greater the concentration of growth factors will be.

"Platelet-rich plasma" or "PRP" is plasma concentrated from whole blood to remove erythrocytes and concentrate the plasma in leucocytes, thrombocytes, and adhesion proteins as compared to whole blood. According to some embodiments, the PRP is autologous PRP. According to some embodiments, the PRP is allogeneic." According to some embodiments, the PRP can be prepared from whole blood by, centrifugation, using the devices and techniques described in U.S. Pat. No. 8,317,672, incorporated herein by reference. According to some embodiments, the platelet concentration of PRP is specifically increased by, centrifugation, fractionation or separation of the red blood cell fraction by any method. According to some embodiments, the method comprises. centrifuging whole blood first by a soft spin such as 8 min at 460 g, wherein the buffy coat is used or further pelleted by a hard spin at higher g values.

According to some embodiments, the concentration of platelets in the PRP so prepared is about a 1.5-20 fold (i.e., 1.5, 2.0, 2.5, 3.0, 3.5, 4.0, 4.5, 5.0, 5.5, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20-fold increase as compared to venous blood, where normal platelet counts in blood range between 150,000/microliter and 350,000/microliter.

According to some embodiments, the growth factor composition comprises a platelet-rich fibrin (PRF) network. According to some embodiments, the PRF is prepared from whole blood without adding any additives or reagents (David M. Dohan, et al, Part I: Technological concepts and evolution, Oral Surg Oral Med Oral Pathol Oral Radiol Ended 2006; 101:E37-44). The method comprises the steps: (1) placing a blood sample without anticoagulant in 10-mL glass or glass coated plastic tubes, which are immediately centrifuged at approximately 400 g for 10 minutes. The absence of anticoagulant implies the activation, within a few minutes, of most of the platelets in contact with the glass tube walls and the release of the coagulation cascades. Fibrinogen is initially concentrated in the top part of the tube, before the circulating thrombin transforms it into fibrin. A fibrin clot is then obtained in the middle of the tube, extending from the upper part of the red corpuscles at the bottom of the tube to the cellular plasma at the top. Platelets are trapped massively in the fibrin meshes. (2) removing the clot from the tube, (3) manually cutting the red cells apart, and (4) manually driving out the fluids trapped in the fibrin matrix (serum). According to some embodiments, in step (1), a buffered anticoagulant is utilized (e.g., anticoagulant citrate dextrose A (ACDA), EDTA, or buffered citrate) to collect blood prior to obtaining PRF. See, e.g., Dohan et al., Trends Biotechnol. 27:158-67 (2009); Correa do Amaral et al., Stem Cells Int., Article ID 7414036 (2016).

An alternative exemplary process comprises the steps: collecting whole blood in a container which holds a separator polyester gel, and centrifuging the container at a speed in the range of 1000 to 5000 rpm for 1 to 20 minutes. The centrifuge time is adjusted according to the centrifuge speed. Optionally, the blood may be centrifuged a second time so as to obtain different concentrations of PRF.

During this process, because blood is collected without any anticoagulant and immediately centrifuged, a natural coagulation process then occurs and allows for the easy collection of a leucocyte- and platelet-rich fibrin (L-PRF) clot, without the need for any biochemical modification of the blood, that is, no anticoagulants, thrombin or calcium chloride are required.

1.3 Cell Culture Compositions

According to some embodiments, the cell culture composition comprises a viable cell culture comprising a population of cells suspended in a culture medium. According to some embodiments, the population of cells suspended in a culture medium have been expanded in vitro. According to some embodiments, the suspended population of cells is one or more selected from the group consisting of fibroblasts, epithelial keratinocytes, stromal cells, or mesenchymal stem cells. According to some embodiments, the suspended population of cells can be one or more of fetal (meaning before birth), infant (meaning from two months to one year old), newborn (meaning birth to about two months of age), neonatal, (meaning during the first month after birth), or adult in origin. According to some embodiments, the fetal cells can be of placental origin. According to some embodiments, the carrier matrix is supersaturated by the suspended population of cells. According to some embodiments, the carrier matrix is supersaturated by the suspended population of cells by centrifugation. According to some embodiments, the carrier matrix supersaturated by the population of cells comprises 10,000,000, 20,000,000, 30,000,000, 40,000,000, 50,000,000, 60,000,000, 70,000,000, 80,000,000, 90,000,000, 100,000,000 or more cells.

Fibroblasts

According to some embodiments, the population of cells is a population of fibroblasts. According to some embodiments, the fibroblasts are effective to synthesize extracellular matrix and collagen. Fibroblasts are the most common cells of connective tissue in humans. Vimentin is the most frequently found intermediate filament in fibroblasts. Thus, fibroblasts may be identified by staining for vimentin, for example by immunohistochemistry using an antibody against vimentin. Furthermore or alternatively, fibroblasts can be identified by producing CXCL-8/IL-8 in response to (recombinant) IL-1α. Fibroblasts are morphologically heterogeneous with diverse appearances depending on their location and activity.

According to some embodiments, the fibroblasts may be fetal, infant, newborn, neonatal, or adult in origin, and may be derived from convenient sources such as skin, cardiac muscle, smooth muscle, skeletal muscle, liver, pancreas, brain, adipose tissue (fat) etc. Such tissues and or organs can be obtained by appropriate biopsy or upon autopsy. According to some embodiments, the fibroblasts are human cells. According to some embodiments, the three dimensional fibroblast culture is a matrix-embedded human dermal construct of newborn dermal fibroblasts cultured in vitro onto a bioabsorbable mesh to produce living, metabolically active tissue. The fibroblasts proliferate across the mesh and secrete a large variety of growth factors and cytokines, including human dermal collagen, fibronectin, and glycosaminoglycans (GAGs), embedding themselves in a self-produced dermal matrix. In culture the fibroblasts produce angiogenic growth factors: VEGF (vascular endothelial growth factor), HGF (hepatocyte growth factor), bFGF (basic fibroblast growth factor), and angiopoietin-1 (See, for example, J. Anat. (2006) 209, pp 527-532).

Epithelial Keratinocytes

According to some embodiments, the population of cells is a population of epithelial keratinocytes. As used herein, the term "keratinocyte" as used herein refers to a cell which expresses cytokeratin. Keratinocytes, which constitute most of the cells in the epidermis or epithelium, may be derived from humans, mice, rats, etc., but are not limited thereto. According to some embodiments, the keratinocytes may be keratinocytes derived from human epidermis. According to some embodiments, the keratinocytes are derived from normal tissue. According to some embodiments, the keratinocytes may be derived from lesions such as chemical and flame burns, wounds, scars, ulcers, etc., but are not limited thereto.

According to some embodiments, the epidermal keratinocytes may be keratinocytes isolated from skin, hair, or nails), keratinocytes derived from induced pluripotent cells (iPS), keratinocytes derived from human embryonic stem cells (hESCs), or a combination thereof. According to some embodiments, the keratinocytes are human primary keratinocytes.

Stromal Cells

According to some embodiments, the population of cells is a population of stromal cells.

Mesenchymal stromal cells are a heterogeneous population of cells, capable of differentiating into different types of mesenchymal mature cells. The differentiation of these cells to reticular endothelial cells, fibroblasts, adipocytes, and osteogenic precursor cells, depend upon influences from various bioactive factors. Multipotent stromal cells, or alternatively mesenchymal stem cells (MSCs), are multipotent cells that can differentiate into a variety of cell types, including: osteoblasts, chondrocytes, adipocytes, pericytes. MSCs have a large capacity for self-renewal while maintaining their multipotency.

Multipotent stromal cells are long, thin cells with a small cell body. The cells have a round nucleus with a prominent nucleolus. The nucleus is surrounded by finely dispersed chromatin particles. The cells also have a small amount of Golgi apparatus, rough endoplasmic reticulum, mitochondria, and polyribosomes.

No single marker that definitely delineates MSCs in vivo has been identified due to the lack of consensus regarding the MSC phenotype, but it generally is considered that MSCs are positive for cell surface markers CD105, CD166, CD90, and CD44 and that MSCs are negative for typical hematopoietic antigens, such as CD45, CD34, and CD14. As for the differentiation potential of MSCs, studies have reported that populations of bone marrow-derived MSCs have the capacity to develop into terminally differentiated mesenchymal phenotypes both in vitro and in vivo, including bone, cartilage, tendon, muscle, adipose tissue, and hematopoietic-supporting stroma. Studies using transgenic and knockout mice and human musculoskeletal disorders have reported that MSC differentiate into multiple lineages during embryonic development and adult homeostasis.

Analyses of the in vitro differentiation of MSCs under appropriate conditions that recapitulate the in vivo process have led to the identification of various factors essential for stem cell commitment. Among them, secreted molecules and their receptors (e.g., transforming growth factor-(3), extracellular matrix molecules (e.g., collagens and proteoglycans), the actin cytoskeleton, and intracellular transcription factors (e.g., CbfaI/Runx2, PPARy, Sox9, and MEF2) have been shown to play important roles in driving the commitment of multipotent MSCs into specific lineages, and maintaining their differentiated phenotypes.

Mesenchymal stromal cells can be isolated from placenta, umbilical cord tissue, namely Wharton's jelly and the umbilical cord blood, amniotic membrane (AM), amniotic fluid, adipose tissue, the corneal limbus, bone marrow, peripheral blood, liver, skin, and the corneal limbus. Currently, efforts to isolate mesenchymal stromal cells focus on the perivascular space and the pericytes; however, basement membranes can be an alternative source of MSCs. Mesenchymal stromal cells also can be isolated from the avascular stroma of the amniotic membrane.

According to some embodiments, the stromal cells are derived from amniotic fluid, or a bone marrow aspirate.

Amniotic fluid stromal cells can be isolated according to the method described in Moraghebi, R. et al, Stem Cell Res. Ther. (2017) 8:190. Processing of the cellular material from the fluid is performed within 2-4 hours. Amniotic fluid is filtered through a sterile mesh gauze pad to remove residual vernix or other large particulates, and then through a 100-μm nylon cell strainer (Fisher Scientific). Filtered samples are centrifuged at 850×g for 5 min and the cell pellet is resuspended in 20-50 ml DMEM+10% FCS depending on the sample volume. Further separation of mononuclear cells from possible red blood cell contamination is done by density gradient centrifugation of the sample over lymphoprep (Medinor AB or AXIS-SHIELD) at 850×g for 20 min at room temperature. The isolated mononuclear cells are counted by Trypan blue exclusion (Sigma-Aldrich), and evaluated for their clonogenic potential (CFU-F assay) or expansion activity. The MNCs are plated at different plating densities of $1\times10^4$-$6\times10^4$ cells per $cm^2$ on collagen I pre-coated six-well plates. At days 11-14, fibroblastic colony forming units are counted and then individual cell colonies are picked for clonal cell expansion. Cells are split every 3 days at a seeding density of $3\times10^3$-$7\times10^3$ cells per $cm^2$ depending on their passage number.

Bone marrow consists of a variety of precursor and mature cell types, including hematopoietic cells (the precursors of mature blood cells) and stromal cells (the precursors of a broad spectrum of connective tissue cells), both of which appear to be capable of differentiating into other cell types. Since the mononuclear fraction of bone marrow contains stromal cells, hematopoietic precursors, and endothelial precursors, the stromal cell components can be purified from the cellular components of a bone marrow aspirate harvested from the subject. According to some embodiments, fresh bone marrow is collected using an aspiration needle, filtered to remove bone fragments and clumps and diluted with buffer. The diluted cell suspension is layered over Ficoll-Paque in a 50 ml conical tube and centrifuged at 445×6 for 35 minutes at 20 C in a swinging bucket rotor without brake. The upper layer is aspirated off, leaving the mononuclear layer undisturbed at the interphase. The mononuclear cell fraction is transferred to a new 50 mL conical tube, and washed by adding buffer, mixing gently and centrifuging at 300×g for 10 minutes at 20 C. The supernatant is removed and discarded. The cell pellet is resuspended in 50 mL buffer and centrifuged at 200×g for 10-15 minutes at 20 C to remove platelets. The supernatant is removed completely. The cell pellet is resuspended in an appropriate amount of buffer for further purification of the bone marrow aspirate stromal cells.

Examples of stromal cell surface markers (positive and negative) include but are not limited to CD105+, CD29+, CD44+, CD73+, CD90+, CD34−, CD45−, CD80−, CD19−, CD5−, CD20−, CD11B−, CD14−, CD19−, CD79−, HLA-DR−, and FMC7−. Other stromal stem cell markers include but are not limited to tyrosine hydroxylase, nestin, and H-NF.

Mesenchymal Stem Cells

According to some embodiments, the population of cells is a population of mesenchymal stem cells.

According to some embodiments, the population of cells comprising stromal stem cells obtained, and/or derived or arising from, placenta, umbilical cord, umbilical cord blood, tooth bud tissue, dentine/pulp tissue, periodontal ligament, gingival, skin, hair, follicle, amniotic fluid, adipose tissue, smooth muscle, skeletal muscle, tendon, ligament, bone, cartilage, bone marrow and/or peripheral blood. According to some embodiments, the mesenchymal stem cells are derived from adipose tissue or from umbilical cord. Other sources also are contemplated.

Methods for producing such cells are known in the art, for example as described in Gronthos S., Zannettino A C W, Kortesidis A, Shi S, Graves S E, Hay S J, Simmons P J (2003) Molecular and cellular characterisation of highly purified human bone marrow stromal stem cells. Journal of Cell Science 116: 1827-1835; Shi S. and Gronthos S. (2003) Perivascular Niche of Postnatal Mesenchymal Stem Cells in Human Bone Marrow and Dental Pulp. Journal of Bone and Mineral Research 18(4): 696-704; Zannettino A C W, Paton S, Kortesidis A, Khor F, Itescu S, Gronthos S (2007) Human Mulipotential Stromal Stem Cells are Derived from a Discrete Subpopulation of STRO-1 bright/CD34−/CD45−/Glycophorin-A-Bone Marrow Cells. Haematologica 92 1707-

1708; and Zannettino A C, Paton S, Arthur A, Khor F, Itescu S, Gimble J M, Gronthos S (2008) Multipotential human adipose-derived stromal stem cells exhibit a perivascular phenotype in vitro and in vivo. Journal of Cellular Physiology 214(2):413-421.

The following table correlates the exemplary protein expression profile of adipose derived stem cells (ASCs) with the corresponding surface markers (Flynn et. al., 2208 Organogenesis, 4(4): 228-235; Gronthos et. al., 2011, J. Cell. Physiol., 189: 54-63).

TABLE 1

Adipose-derived Stem Cell Protein Expression and Surface Marker Profile

| Class | Protein | Marker |
|---|---|---|
| Cell Adhesion | Integrin 131 | CD29 |
| | Integrin ct4 | CD49d |
| | Integrin $a_s$ | $CD49_e$ |
| | Vascular Cell Adhesion Molecule | VCAM; CD106 |
| | Intracellular Adhesion Molecule-1 | ICAM; CD54 |
| | Activated Leukocyte Cell Adhesion Molecule | ALCAM; CD166 |
| | Tetraspan | CD9 |
| | Endoglin | CD 105 |
| | Mucl8 | CD146 |
| Receptors | Hyaluronate receptor | CD44 |
| | Transferrin receptor | CD71 |
| | Insulin receptor | |
| | Glucocorticoid receptor | |
| | Triiodothyronine (T3) receptor | |
| | Retinoic acid receptor | |
| ECM | Collagen type I | |
| | Collagen type III | |
| | Collagen type IV | |
| | Collagen type VI | CD68 |
| | Osteopontin | |
| | Osteonectin | |
| | Fibronectin | |
| | Fibrin | |
| | Vitronectin | |
| Cytoskeletal | A-smooth muscle actin | |
| Cytoskeletal | Vimentin | |
| Other | HLA-ABC | Major histocompatibility complex class I antigen |
| | DAF | CD55 |
| | Complement protectin | CD59 |

Stem cells are not terminally differentiated. Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive, for example only lymphoid, or erythroid lineages in a hematopoietic setting. According to some embodiments, the population of stem cells or progenitor cells may have been maintained in culture, such that it has been subjected to culturing for a prolonged duration of time, such as, 1 day to 10 years or more, such as, 1 day, 3 days, 7 days, 2 weeks, 5 weeks, 10 weeks, 3 months, 10 months, 1 year, 3 years, 5 years, 10 years, or more.

Mesenchymal stem cells (MSCs) are multipotent stem cells, i.e. they are capable of giving rise to multiple different types of cells. MSCs, which are capable of differentiating into at least one of an osteoblast, a chondrocyte, an adipocyte, or a myocyte, can be isolated from any type of tissue. According to some embodiments, MSCs can be isolated from bone marrow, adipose tissue, umbilical cord, or peripheral blood. According to some embodiments, MSCs may be isolated from bone marrow (BM-MSCs) or adipose tissue (ASCs). According to some embodiments, the MSCs are obtained from lipoaspirates, themselves obtained from adipose tissue. The term MSC shall be taken to include the progeny of said MSC, for example but not limited to subcultured descendants thereof.

Both the presence of certain markers and the absence of certain markers may characterize stem cells. These markers may be detected using a number of methods that may depend on the nature of the marker. According to some embodiments, the marker may be associated with specific epitopes which are identified by antibodies. Stem cells may also be identified by functional assays both in vitro and in vivo, particularly assays relating to the ability of stem cells to give rise to multiple differentiated progeny.

According to some embodiments, the population of cells is a population of autologous, expanded fibroblasts. According to some embodiments, the population of fibroblasts is of dermal origin (meaning of or relating to skin). According to some embodiments, the population of fibroblasts is of auricular (meaning relating to the ear) dermis origin. According to some embodiments, the population of fibroblasts is of oral mucosal (meaning the mucous membrane lining the inside of the mouth) origin. According to some embodiments, the population of cells is a population of allogeneic amniotic fluid-derived stromal cells. According to some embodiments, the population of cells is a population of bone marrow aspirate-derived stromal cells. According to some such embodiments, the bone marrow aspirate-derived stromal cells are autologous. According to some such embodiments, the bone marrow aspirate-derived stromal cells are expanded in vitro. According to some embodiments, the population of cells is a population of adipocyte-derived stem cells. According to some such embodiments, the population of adipocyte-derived stem cells is autologous. According to some such embodiments, the population of adipocyte-derived stem cells is allogeneic. According to some embodiments, the population of cells is a population of umbilical cord stem cells. According to some such embodiments, the population of cells is allogeneic. According to some embodiments, the at least one viable population of cells secretes at least one growth-inductive factor. According to some embodiments, the at least one viable population of cells is capable of regenerating a target tissue.

According to some embodiments where hard tissue grafts are desired, the cells can comprise one or more of fibroblasts, amniotic fluid-derived stromal cells, bone marrow aspirate-derived stromal cells, adipose-derived stem cells, tooth/pulp-derived stem cells, and umbilical cord stem cells. Thus, the cells can comprise fibroblasts, amniotic fluid-derived stromal cells, bone marrow aspirate-derived stromal cells, adipose-derived stem cells, tooth/pulp-derived stem cells, or umbilical cord stem cells; fibroblasts and amniotic fluid-derived stromal cells, bone marrow aspirate-derived stromal cells, adipose-derived stem cells, tooth/pulp-derived stem cells, or umbilical cord stem cells; amniotic fluid-derived stromal cells and bone marrow aspirate-derived stromal cells, adipose-derived stem cells, tooth/pulp-derived stem cells, or umbilical cord stem cells; bone marrow aspirate-derived stromal cells and adipose-derived stem cells, tooth/pulp-derived stem cells, or umbilical cord stem cells; adipose-derived stem cells and tooth/pulp-derived stem cells or umbilical cord stem cells; tooth/pulp-derived stem cells and umbilical cord stem cells; fibroblasts and amniotic fluid-derived stromal cells and bone marrow aspirate-derived stromal cells, adipose-derived stem cells, tooth/pulp-derived stem cells, or umbilical cord stem cells; fibroblasts and bone marrow aspirate-derived stromal cells and adipose-derived stem cells, tooth/pulp-derived stem cells, or umbilical cord stem cells; fibroblasts and adipose-derived stem cells and tooth/pulp-derived stem cells or umbilical cord stem cells; fibroblasts, tooth/pulp-derived stem cells, and umbilical cord stem cells; amniotic fluid-derived stromal cells and bone marrow aspirate-derived stromal cells and adipose-derived stem cells, tooth/pulp-derived stem cells, or umbilical cord stem cells; amniotic fluid-derived stromal cells and adipose-derived stem cells and tooth/pulp-derived stem cells or umbilical cord stem cells; amniotic fluid-derived stromal cells, tooth/pulp-derived stem cells, and umbilical cord stem cells; bone marrow aspirate-derived stromal cells and adipose-derived stem cells and tooth/pulp-derived stem cells or umbilical cord stem cells; bone marrow aspirate-derived stromal cells, tooth/pulp-derived stem cells, and umbilical cord stem cells; adipose-derived stem cells, tooth/pulp-derived stem cells, and umbilical cord stem cells; fibroblasts, amniotic fluid-derived stromal cells, and bone marrow aspirate-derived stromal cells and adipose-derived stem cells, tooth/pulp-derived stem cells, or umbilical cord stem cells; fibroblasts, bone marrow aspirate-derived stromal cells, and adipose-derived stem cells and tooth/pulp-derived stem cells or umbilical cord stem cells; fibroblasts, adipose-derived stem cells, tooth/pulp-derived stem cells, and umbilical cord stem cells; amniotic fluid-derived stromal cells, bone marrow aspirate-derived stromal cells, and adipose-derived stem cells and tooth/pulp-derived stem cells or umbilical cord stem cells; amniotic fluid-derived stromal cells, adipose-derived stem cells, tooth/pulp-derived stem cells, and umbilical cord stem cells; bone marrow aspirate-derived stromal cells, adipose-derived stem cells, tooth/pulp-derived stem cells, and umbilical cord stem cells; fibroblasts, amniotic fluid-derived stromal cells, bone marrow aspirate-derived stromal cells, and adipose-derived stem cells and tooth/pulp-derived stem cells or umbilical cord stem cells; fibroblasts, bone marrow aspirate-derived stromal cells, adipose-derived stem cells, tooth/pulp-derived stem cells, and umbilical cord stem cells; amniotic fluid-derived stromal cells, bone marrow aspirate-derived stromal cells, adipose-derived stem cells, tooth/pulp-derived stem cells, and umbilical cord stem cells; or fibroblasts, amniotic fluid-derived stromal cells, bone marrow aspirate-derived stromal cells, adipose-derived stem cells, tooth/pulp-derived stem cells, and umbilical cord stem cells.

According to some embodiments where soft tissue grafts are desired, the cells can comprise one or more of fibroblasts, epithelial keratinocytes, amniotic fluid-derived stromal cells, bone marrow aspirate-derived stromal cells, adipose-derived stem cells, tooth/pulp-derived stem cells, and umbilical cord stem cells. Thus, the cells can comprise fibroblasts, epithelial keratinocytes, amniotic fluid-derived stromal cells, bone marrow aspirate-derived stromal cells, adipose-derived stem cells, tooth/pulp-derived stem cells, or umbilical cord stem cells; fibroblasts and epithelial keratinocytes, amniotic fluid-derived stromal cells, bone marrow aspirate-derived stromal cells, adipose-derived stem cells, tooth/pulp-derived stem cells, or umbilical cord stem cells; epithelial keratinocytes and amniotic fluid-derived stromal cells, bone marrow aspirate-derived stromal cells, adipose-derived stem cells, tooth/pulp-derived stem cells, or umbilical cord stem cells; amniotic fluid-derived stromal cells and bone marrow aspirate-derived stromal cells, adipose-derived stem cells, tooth/pulp-derived stem cells, or umbilical cord stem cells; bone marrow aspirate-derived stromal cells and adipose-derived stem cells, tooth/pulp-derived stem cells, or umbilical cord stem cells; adipose-derived stem cells and tooth/pulp-derived stem cells or umbilical cord stem cells; tooth/pulp-derived stem cells and umbilical cord stem cells; fibroblasts and epithelial keratinocytes and amniotic fluid-derived stromal cells, bone marrow aspirate-derived stromal cells, adipose-derived stem cells, tooth/pulp-derived stem cells, or umbilical cord stem cells; fibroblasts and amniotic fluid-derived stromal cells and bone marrow aspirate-derived stromal cells, adipose-derived stem cells, tooth/pulp-derived stem cells, or umbilical cord stem cells; fibroblasts and bone marrow aspirate-derived stromal cells and adipose-derived stem cells, tooth/pulp-derived stem cells, or umbilical cord stem cells; fibroblasts and adipose-derived stem cells and tooth/pulp-derived stem cells or umbilical cord stem cells; fibroblasts, tooth/pulp-derived stem cells, and umbilical cord stem cells; epithelial keratinocytes and amniotic fluid-derived stromal cells and bone marrow aspirate-derived stromal cells, adipose-derived stem cells, tooth/pulp-derived stem cells, or umbilical cord stem cells; epithelial keratinocytes and bone marrow aspirate-derived stromal cells and adipose-derived stem cells, tooth/pulp-derived stem cells, or umbilical cord stem cells; epithelial keratinocytes and adipose-derived stem cells and tooth/pulp-derived stem cells or umbilical cord stem cells; epithelial keratinocytes, tooth/pulp-derived stem cells, and umbilical cord stem cells; amniotic fluid-derived stromal cells and bone marrow aspirate-derived stromal cells and adipose-derived stem cells, tooth/pulp-derived stem cells, or umbilical cord stem cells; amniotic fluid-derived stromal cells and adipose-derived stem cells and tooth/pulp-derived stem cells or umbilical cord stem cells; amniotic fluid-derived stromal cells, tooth/pulp-derived stem cells, and umbilical cord stem cells; bone marrow aspirate-derived stromal cells and adipose-derived stem cells and tooth/pulp-derived stem cells or umbilical cord stem cells; bone marrow aspirate-derived stromal cells, tooth/pulp-derived stem cells, and umbilical cord stem cells; fibroblasts, epithelial keratinocytes, and amniotic fluid-derived stromal cells and bone marrow aspirate-derived stromal cells, adipose-derived stem cells, tooth/pulp-derived stem cells, or umbilical cord stem cells; fibroblasts, amniotic fluid-derived stromal cells, and bone marrow aspirate-derived stromal cells and adipose-derived stem cells, tooth/pulp-derived stem cells, or umbilical cord stem cells; fibroblasts, bone marrow aspirate-derived stromal cells, and adipose-derived stem cells and tooth/pulp-derived stem cells or umbilical cord stem cells; fibroblasts, adipose-derived stem cells, tooth/pulp-derived stem cells, and umbilical cord stem cells; epithelial keratinocytes, amniotic fluid-derived stromal cells, and bone marrow aspirate-derived stromal cells and adipose-derived stem cells, tooth/pulp-derived stem cells, or umbilical cord stem cells; epithelial keratinocytes, bone marrow aspirate-derived stromal cells, and adipose-derived stem cells and tooth/pulp-derived stem cells or umbilical cord stem cells; epithelial keratinocytes, adipose-derived stem cells, tooth/pulp-derived stem cells, and umbilical cord stem cells; amniotic fluid-derived stromal cells, bone marrow aspirate-derived stromal cells, and adipose-derived stem cells and tooth/pulp-derived stem cells or umbilical cord stem cells; amniotic fluid-derived stromal cells, adipose-derived stem cells, tooth/pulp-derived stem cells, and umbilical cord stem cells; bone marrow aspirate-derived stromal cells, adipose-derived stem cells, tooth/pulp-derived stem cells, and umbilical cord stem cells; fibroblasts, epithelial keratinocytes, amniotic fluid-derived stromal cells, and bone marrow aspirate-derived stromal cells and adipose-derived stem cells, tooth/pulp-derived stem cells, or umbilical cord stem cells; fibroblasts, amniotic fluid-derived stromal cells, bone marrow aspirate-derived stromal cells, and adipose-derived stem cells and tooth/pulp-derived stem cells or umbilical cord stem cells; fibroblasts, bone marrow aspirate-derived stromal cells, adipose-derived stem cells, tooth/pulp-derived stem cells, and umbilical cord stem cells; epithelial keratinocytes, amniotic fluid-derived stromal cells, bone marrow aspirate-derived stromal cells, and adipose-derived stem cells and tooth/pulp-derived stem cells or umbilical cord stem cells; epithelial keratinocytes, bone marrow aspirate-derived stromal cells, adipose-derived stem cells, tooth/pulp-derived stem cells, and umbilical cord stem cells; amniotic fluid-derived stromal cells, bone marrow aspirate-derived stromal cells, adipose-derived stem cells, tooth/pulp-derived stem cells, and umbilical cord stem cells; fibroblasts, epithelial keratinocytes, amniotic fluid-derived stromal cells, bone marrow aspirate-derived stromal cells, and adipose-derived stem cells and tooth/pulp-derived stem cells or umbilical cord stem cells; fibroblasts, amniotic fluid-derived stromal cells, bone marrow aspirate-derived stromal cells, adipose-derived stem cells, tooth/pulp-derived stem cells, and umbilical cord stem cells; epithelial keratinocytes, amniotic fluid-derived stromal cells, bone marrow aspirate-derived stromal cells, adipose-derived stem cells, tooth/pulp-derived stem cells, and umbilical cord stem cells; or fibroblasts, epithelial keratinocytes, amniotic fluid-derived stromal cells, bone marrow aspirate-derived stromal cells, adipose-derived stem cells, tooth/pulp-derived stem cells, and umbilical cord stem cells.

The ratio of growth factor composition to cell culture composition in the graft can be, in a volume:volume ratio, at least about 10:1, at least about 11:1, at least about 12:1, at least about 13:1, at least about 14:1, at least about 15:1, at least about 16:1, at least about 17:1, at least about 18:1, at least about 19:1, at least about 20:1, at least about 21:1, at least about 22:1, at least about 23:1, at least about 24:1, at least about 25:1, at least about 30:1, at least about 35:1, at least about 40:1, at least about 45:1, at least about 50:1, or more.

The type of cell culture medium and the method for culturing cells is not particularly limited. A number of base media are known in the art of mammalian cell culture, such as Dulbecco's Modified Eagle Media (DMEM), Knockout-DMEM (KO-DMEM), and DMEM/F12, although any base medium that supports the growth of cells can be employed.

According to some embodiments, the cell culture medium is biologically compatible with the subject in that the cell culture medium that is used to culture cells does not contain any components that would be expected to negatively affect the health of the subject after administration of the induced cells. Thus, an appropriate cell culture medium can also comprise one or more serum-free medium supplements, i.e., a supplement that can be added to a medium to replace some or all of the serum that would normally be added to the medium to support the propagation and/or maintenance of cells in culture.

According to some embodiments, the cells can be grown using a cell expansion system (CES), which can be used to grow, expand, and/or differentiate a variety of cell types that may be used for both research and therapeutic purposes. An exemplary CES system is disclosed in US20180142199, incorporated by reference herein in its entirety. According to some embodiments, the CES is a TerumoBCT Quantum® CES.

A typical CES includes a first fluid circulation path and a second fluid circulation path. The first fluid flow path has at least opposing ends and fluidly associated with a cell growth chamber. One opposing end may be fluidly associated with a first inlet of the CES, and the other opposing end may be fluidly associated with a first outlet of the cell growth chamber. Fluid in the first circulation path may flow through the bioreactor. According to some embodiments where the bioreactor is a hollow fiber bioreactor, the fluid may flow through the interior of a hollow fiber of a hollow fiber membrane disposed in the cell growth chamber. Further, a first fluid flow controller may be operably connected to first fluid flow path and control the flow of fluid in the first circulation path.

A second fluid circulation path includes a second fluid flow path, a cell growth chamber, and a second fluid flow controller. The second fluid flow path has at least opposing end, which are fluidly associated with an inlet port and an outlet port of the cell growth chamber. Fluid flowing through the cell growth chamber may, according to some embodiments, be in contact with the outside of a hollow fiber membrane in the cell growth chamber. The second fluid circulation path may be operably connected to a second fluid flow controller.

The first and second fluid circulation paths may, according to some embodiments, be separated in the cell growth chamber by a hollow fiber membrane. In these embodiments, fluid in the first fluid circulation path flows through an intracapillary (IC) space, including the interior, of the hollow fibers in the cell growth chamber (the "IC Loop"). Fluid in the second fluid circulation path flows through an extracapillary (EC) space in the cell growth chamber (the "EC Loop"). Fluid in the first fluid circulation path can flow in either a co-current or counter-current direction with respect to flow of fluid in the second fluid circulation path. That is, fluid can flow clockwise or counter-clockwise in both the IC and EC loops, or they can flow in opposite directions.

A fluid inlet path is fluidly associated with the first fluid circulation path. The fluid inlet path allows fluid to flow into the first fluid circulation path, while a fluid outlet path allows fluid to leave the CES. It is noted that according to some embodiments a second fluid inlet path may be associated with the second fluid circulation path and a second outlet path may be associated with the first fluid circulation path. A third fluid flow controller can be operably associated with the fluid inlet path. A fourth fluid flow controller may be associated with the fluid outlet path.

Fluid flow controllers as used herein can be a pump, valve, clamp, or combinations thereof. Multiple pumps, valves, and clamps can be arranged in any combination. In various embodiments, the fluid flow controller is or includes a peristaltic pump. In further embodiments, fluid circulation paths, inlet ports, and outlet ports can be constructed of tubing of any material.

Generally, any kind of fluid, including buffers, protein containing fluid, and cell-containing fluid can flow through the various circulations paths, inlet paths, and outlet paths. According to some embodiments, the fluid can further comprise particles for enhancing cell growth.

According to some embodiments, the cell culture composition comprises particles that provide binding and growth sites for the cells in the culture.

According to some embodiments, the diameter of the particles can be about 30 μm to about 40 μm, about 31 μm to about 40 μm, about 32 μm to about 40 μm, about 33 μm to about 40 μm, about 34 μm to about 40 μm, about 35 μm to about 40 μm, about 36 μm to about 40 μm, about 37 μm to about 40 μm, about 38 μm to about 40 μm, about 39 μm to about 40 μm, about 30 μm to about 39 μm, about 31 μm to about 39 μm, about 32 μm to about 39 μm, about 33 μm to about 39 μm, about 34 μm to about 39 μm, about 35 μm to about 39 μm, about 36 μm to about 39 μm, about 37 μm to about 39 μm, about 38 μm to about 39 μm, about 30 μm to about 38 μm, about 31 μm to about 38 μm, about 32 μm to about 38 μm, about 33 μm to about 38 μm, about 34 μm to about 38 μm, about 35 μm to about 38 μm, about 36 μm to about 38 μm, about 37 μm to about 38 μm, about 30 μm to about 37 μm, about 31 μm to about 37 μm, about 32 μm to about 37 μm, about 33 μm to about 37 μm, about 34 μm to about 37 μm, about 35 μm to about 37 μm, about 36 μm to about 37 μm, about 30 μm to about 36 μm, about 31 μm to about 36 μm, about 32 μm to about 36 μm, about 33 μm to about 36 μm, about 34 μm to about 36 μm, about 35 μm to about 36 μm, about 30 μm to about 35 μm, about 31 μm to about 35 μm, about 32 μm to about 35 μm, about 33 μm to about 35 μm, about 34 μm to about 35 μm, about 30 μm to about 34 μm, about 31 μm to about 34 μm, about 32 μm to about 34 μm, about 33 μm to about 34 μm, about 30 μm to about 33 μm, about 31 μm to about 33 μm, about 32 μm to about 33 μm, about 30 μm to about 32 μm, about 31 μm to about 32 μm, about 30 μm to about 31 μm, about 30 μm, about 31 μm, about 32 μm, about 33 μm, about 34 μm, about 35 μm, about 36 μm, about 37 μm, about 38 μm, about 39 μm, about 40 μm, about 30.1 μm, about 30.2 μm, about 30.3 μm, about 30.4 μm, about 30.5 μm, about 30.6 μm, about 30.7 μm, about 30.8 μm, about 30.9 μm, about 31.1 μm, about 31.2 μm, about 31.3 μm, about 31.4 μm, about 31.5 μm, about 31.6 μm, about 31.7 μm, about 31.8 μm, about 31.9 μm, about, 32.1 μm, about 32.2 μm, about 32.3 μm, about 32.4 μm, about 32.5 μm, about 32.6 μm, about 32.7 μm, about 32.8 μm, about 32.9 μm, about 33.1 μm, about 33.2 μm, about 33.3 μm, about 33.4 μm, about 33.5 μm, about 33.6 μm, about 33.7 μm, about 33.8 μm, about 33.9 μm, about 34.1 μm, about 34.2 μm, about 34.3 μm, about 34.4 μm, about 34.5 μm, about 34.6 μm, about 34.7 μm, about 34.8 μm, about 34.9 μm, about 35.1 μm, about 35.2 μm, about 35.3 μm, about 35.4 μm, about 35.5 μm, about 35.6 μm, about 35.7 μm, about 35.8 μm, about 35.9 μm, about 36.1 μm, about 36.2 μm, about 36.3 μm, about 36.4 μm, about 36.5 μm, about 36.6 μm, about 36.7 μm, about 36.8 μm, about 36.9 μm, about 37.1 μm, about 37.2 μm, about 37.3 μm, about 37.4 μm, about 37.5 μm, about 37.6 μm, about 37.7 μm, about 37.8 μm, about 37.9 μm, about 38.1 μm, about 38.2 μm, about 38.3 μm, about 38.4 μm, about 38.5 μm, about 38.6 μm, about 38.7 μm, about 38.8 μm, about 38.9 μm, about 39.1 μm, about 39.2 μm, about 39.3 μm, about 39.4 μm, about 39.5 μm, about 39.6 μm, about 39.7 μm, about 39.8 μm, or about 39.9 μm. Such particles are suitable for use in automated culture systems.

According to some embodiments, the diameter of the particles can range from about 0.25 mm to about 1.0 mm for hard tissue repair, using traditional manual tissue culture techniques, i.e., about 0.25 mm, about 0.26 mm, about 0.27 mm, about 0.28 mm, about 0.29 mm, about 0.3 mm, about 0.31 mm, about 0.32 mm, about 0.33 mm, about 0.34 mm, about 0.35 mm, about 0.36 mm, about 0.37 mm, about 0.38 mm, about 0.39 mm, about 0.4 mm, about 0.41 mm, about 0.42 mm, about 0.43 mm, about 0.44 mm, about 0.45 mm, about 0.46 mm, about 0.47 mm, about 0.48 mm, about 0.49 mm, about 0.5 mm, about 0.51 mm, about 0.52 mm, about 0.53 mm, about 0.54 mm, about 0.55 mm, about 0.56 mm, about 0.57 mm, about 0.58 mm, about 0.59 mm, about 0.60 mm, about 0.61 mm, about 0.62 mm, about 0.63 mm, about 0.64 mm, about 0.65 mm, about 0.66 mm, about 0.67 mm, about 0.68 mm, about 0.69 mm, about 0.7 mm, about 0.71 mm, about 0.72 mm, about 0.73 mm, about 0.74 mm, about 0.75 mm, about 0.76 mm, about 0.77 mm, about 0.78 mm, about 0.79 mm, about 0.8 mm, about 0.81 mm, about 0.82 mm, about 0.83 mm, about 0.84 mm, about 0.85 mm, about 0.86 mm, about 0.87 mm, about 0.88 mm, about 0.89 mm, about 0.9 mm, about 0.91 mm, about 0.92 mm, about 0.93 mm, about 0.94 mm, about 0.95 mm, about 0.96 mm, about 0.97 mm, about 0.98 mm, about 0.99 mm, or about 1 mm.

According to some embodiments, the diameter of the particles can range from about 0.3 mm to about 1.0 mm, about 0.35 mm to about 1.0 mm, about 0.4 mm to about 1.0 mm, about 0.45 mm to about 1.0 mm, about 0.5 mm to about 1.0 mm, about 0.55 mm to about 1.0 mm, about 0.6 mm to about 1.0 mm, about 0.65 mm to about 1.0 mm, about 0.7 mm to about 1.0 mm, about 0.75 mm to about 1.0 mm, about 0.8 mm to about 1.0 mm, about 0.85 mm to about 1.0 mm, about 0.9 mm to about 1.0 mm, about 0.95 mm to about 1.0 mm, about 0.25 mm to about 0.95 mm, about 0.3 mm to about 0.95 mm, about 0.35 mm to about 0.95 mm, about 0.4 mm to about 0.95 mm, about 0.45 mm to about 0.95 mm, about 0.5 mm to about 0.95 mm, about 0.55 mm to about 0.95 mm, about 0.6 mm to about 0.95 mm, about 0.65 mm to about 0.95 mm, about 0.7 mm to about 0.95 mm, about 0.75 mm to about 0.95 mm, about 0.8 mm to about 0.95 mm, about 0.85 mm to about 0.95 mm, about 0.9 mm to about 0.95 mm, about 0.25 mm to about 0.9 mm, about 0.3 mm to about 0.9 mm, about 0.35 mm to about 0.9 mm, about 0.4 mm to about 0.9 mm, about 0.45 mm to about 0.9 mm, about 0.5 mm to about 0.9 mm, about 0.55 mm to about 0.9 mm, about 0.6 mm to about 0.9 mm, about 0.65 mm to about 0.9 mm, about 0.7 mm to about 0.9 mm, about 0.75 mm to about 0.9 mm, about 0.8 mm to about 0.9 mm, about 0.85 mm to about 0.9 mm, about 0.25 mm to about 0.85 mm, about 0.3 mm to about 0.85 mm, about 0.35 mm to about 0.85 mm, about 0.4 mm to about 0.85 mm, about 0.45 mm to about 0.85 mm, about 0.5 mm to about 0.85 mm, about 0.55 mm to about 0.85 mm, about 0.6 mm to about 0.85 mm, about 0.65 mm to about 0.85 mm, about 0.7 mm to about 0.85 mm, about 0.75 mm to about 0.85 mm, about 0.8 mm to about 0.85 mm, about 0.25 mm to about 0.8 mm, about 0.3 mm to about 0.8 mm, about 0.35 mm to about 0.8 mm, about 0.4 mm to about 0.8 mm, about 0.45 mm to about 0.8 mm, about 0.5 mm to about 0.8 mm, about 0.55 mm to about 0.8 mm, about 0.6 mm to about 0.8 mm, about 0.65 mm to about 0.8 mm, about 0.7 mm to about 0.8 mm, about 0.75 mm to about 0.8 mm, about 0.25 mm to about 0.75 mm, 0.3 mm to about 0.75 mm, 0.35 mm to about 0.75 mm, 0.4 mm to about 0.75 mm, 0.45 mm to about 0.75 mm, 0.5 mm to about 0.75 mm, 0.55 mm to about 0.75 mm, 0.6 mm to about 0.75 mm, 0.85 mm to about 0.75 mm, 0.7 mm to about 0.75 mm, 0.25 mm to about 0.7 mm, 0.3 mm to about 0.7 mm, 0.35 mm to about 0.7 mm, 0.4 mm to about 0.7 mm, 0.45 mm to about 0.7 mm, 0.5 mm to about 0.7 mm, 0.55 mm to about 0.7 mm, 0.6 mm to about 0.7 mm, 0.65 mm to about 0.7 mm, 0.25 mm to about 0.65 mm, 0.3 mm to about 0.65 mm, 0.35 mm to about 0.65 mm, 0.4 mm to about 0.65 mm, 0.45 mm to about 0.65 mm, 0.5 mm to about 0.65 mm, 0.55 mm to about 0.65 mm, 0.6 mm to about 0.65 mm, 0.25 mm to about 0.6 mm, 0.3 mm to about 0.6 mm, 0.35 mm to about 0.6 mm, 0.4 mm to about 0.6 mm, 0.45 mm to about 0.6 mm, 0.5 mm to about 0.6 mm, 0.55 mm to about 0.6 mm, 0.25 mm to about 0.55 mm, 0.3 mm to about 0.55 mm, 0.35 mm to about 0.55 mm, 0.4 mm to about 0.55 mm, 0.45 mm to about 0.55 mm, 0.5 mm to about 0.55 mm, 0.25 mm to about 0.5 mm, 0.3 mm to about 0.5 mm, 0.35 mm to about 0.5 mm, 0.4 mm to about 0.5 mm, 0.45 mm to about 0.5 mm, 0.25 mm to about 0.45 mm, 0.3 mm to about 0.45 mm, 0.35 mm to about 0.45 mm, 0.4 mm to about 0.45 mm, 0.25 mm to about 0.4 mm, 0.3 mm to about 0.4 mm, 0.35 mm to about 0.4 mm, 0.25 mm to about 0.35 mm, 0.3 mm to about 0.35 mm, or 0.25 mm to about 0.3 mm. Such particles can be suitable for use in manual culture systems.

Regardless of the size of the particles, the particles must be osteoconductive.

The method of forming the particles is not particularly limited, and a method known in the art, for example, by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation. At the time of forming the particle, if necessary, a suitable solvent may be used, and drying of the formed particle may be additionally performed.

According to some embodiments, the particles comprise a core, and optionally one or more coatings (outer layers) surrounding the core. The core may include additional materials such as fillers, fiber materials (cellulose or synthetic fibres), stabilizing agents, solubilizing agents, suspension agents, viscosity regulating agents, light spheres, plasticizers, salts, lubricants, and fragrances. The core may include a binder, such as synthetic polymer, wax, fat, or carbohydrate.

According to some embodiments, the core may include a salt of a multivalent cation, a reducing agent, an antioxidant, a peroxide decomposing catalyst and/or an acidic buffer component.

According to some embodiments, the core comprises hydroxyapatite, tricalcium phosphate, fibrous collagen, biphasic calcium phosphate, calcium phosphate, calcium pyrophosphate, calcium carbonate, dicalcium phosphate dehydrate, dicalcium phosphate anhydrous, polylactic acid, poly(D,L) lactide, carbonate apatite, octacalcium phosphate, $TiO_2$, biosilicate glass (e.g., Pyrex® or Bioglass®), titanium, tantalum, $Al_2O_3$, poly(2-hydroxyethyl methacrylate), or a combination thereof (e.g., tricalcium phosphate and calcium pyrophosphate, hydroxyapatite and calcium carbonate, hydroxyapatite and tricalcium phosphate).

According to some embodiments, the core comprises a salt (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as, e.g., sucrose, dextrin, glucose, lactose, sorbitol), sugar or sugar derivative (such as, e.g., sucrose, dextrin, glucose, lactose, sorbitol), small organic molecules, starch, flour, cellulose and minerals, and/or clay minerals (also known as hydrous aluminium phyllosilicates). According to some embodiments, the core comprises a clay mineral such as kaolinite or kaolin.

The core may be coated with any of the aforementioned compositions in an amount of at least 0.1% by weight of the core, e.g., at least 0.5%, 1% or 5%. The amount may be at most 100%, 70%, 50%, 40% or 30%.

Method of Preparing Grafts

According to some embodiments, a method for producing a graft for bony tissue repair comprises:

(a) preparing a growth factor composition comprising platelet-rich fibrin from peripheral blood of a subject;

(b) preparing a cell culture composition by expanding in vitro a suspended population of cells in a culture medium comprising particles (e.g., of a diameter of about 30 μm to about 40 μm), the cell culture composition comprising the suspended population of cells and the cells impregnated on or in a surface of the particles; wherein the particles are osteoconductive;

(c) mixing the growth factor composition with the cell culture composition in a ratio of growth factor composition to cell culture composition of at least about 10:1 (v/v) to form a growth factor composition-cell culture composition mixture; and (d) combining the growth factor composition-cell culture composition mixture with a three-dimensional carrier matrix comprising one or more of collagen, tri-calcium phosphate, de-mineralized bone strips, de-mineralized bone particles, dentin, amnion membrane, and chorion membrane to form the graft; and (e) sterilely decanting the complete graft onto a sterile surgical field.

According to some embodiments, step (b) comprises expanding the population of cells in an automated cell reactor comprising capillary fibers, wherein the capillary fibers contain a coated inner surface, and wherein the viable cells becomes attached to the coated inner surface. According to some embodiments, the carrier matrix is supersaturated by the suspended viable population of cells. According to some embodiments, the carrier matrix is supersaturated by the suspended population of cells by centrifugation. According to some embodiments, the carrier matrix supersaturated by the population of cells comprises 10,000,000, 20,000,000, 30,000,000, 40,000,000, 50,000,000, 60,000,000, 70,000,000, 80,000,000, 90,000,000, 100,000,000 or more cells.

According to some embodiments, a method for producing a membrane sheet composite graft comprises:

(a) preparing a growth factor composition comprising platelet-rich fibrin from peripheral blood of a subject;

(b) preparing a cell culture composition by expanding in vitro a suspended population of cells in a culture medium comprising particles (e.g., of a diameter of about 30 μm to about 40 μm), the cell culture composition comprising the suspended population of cells and the cells impregnated on or in a surface of the particles; wherein the particles are osteoconductive;

(c) mixing the growth factor composition with the cell culture composition in a ratio of growth factor composition to cell culture composition of at least about 10:1 (v/v) to form a growth factor composition-cell culture composition mixture; and (d) combining the growth factor composition-cell culture composition mixture with a three-dimensional carrier matrix comprising one or more of an amnion membrane, a chorion membrane or an amnion/chorion membrane plus one or more of a collagen, tri-calcium phosphate, de-mineralized bone strips, de-mineralized bone particles, or dentin, to form the graft; and (e) sterilely decanting the complete graft onto a sterile surgical field, wherein the graft comprises pores with a diameter of about 30 µm to about 250 µm, i.e., about 30 µm, about 35 µm, about 40 µm, about 45 µm, about 50 µm, about 55 µm, about 60 µm, about 65 µm, about 70 µm, about 75 µm, about 80 µm about 85 µm, about 90 µm, about 95 µm, about 100 µm, about 105 µm, about 110 µm, about 115 µm, about 120 µm, about 125 µm, about 130 µm, about 135 µm, about 140 µm, about 145 µm, about 150 µm, about 155 µm, about 160 µm, about 165 µm, about 170 µm, about 175 µm, about 180 µm, about 185 µm, about 190 µm, about 200 µm, about 205 µm, about 210 µm, about 215 µm, about 220 µm, about 225 µm, about 230 µm, about 235 µm, about 240 µm, about 245 µm, about 250 µm. According to some embodiments, the pores range from about 40 µm to about 250 µm, about 50 µm to about 250 µm, about 60 µm to about 250 µm, about 70 µm to about 250 µm, about 80 µm to about 250 µm, about 90 µm to about 250 µm, about 100 µm to about 250 µm, about 110 µm to about 250 µm, about 120 µm to about 250 µm, about 130 µm to about 250 µm, about 140 µm to about 250 µm, about 150 µm to about 250 µm, about 160 µm to about 250 µm, about 170 µm to about 250 µm, about 180 µm to about 250 µm, about 190 µm to about 250 µm, about 200 µm to about 250 µm, about 210 µm to about 250 µm, about 220 µm to about 250 µm, about 230 µm to about 250 µm, about 240 µm to about 250 µm, about 30 µm to about 240 µm, about 40 µm to about 240 µm, about 50 µm to about 240 µm, about 60 µm to about 240 µm, about 70 µm to about 240 µm, about 80 µm to about 240 µm, about 90 µm to about 240 µm, about 100 µm to about 240 µm, about 110 µm to about 240 µm, about 120 µm to about 240 µm, about 130 µm to about 240 µm, about 140 µm to about 240 µm, about 150 µm to about 240 µm, about 160 µm to about 240 µm, about 170 µm to about 240 µm, about 180 µm to about 240 µm, about 190 µm to about 240 µm, about 200 µm to about 240 µm, about 210 µm to about 240 µm, about 220 µm to about 240 µm, about 230 µm to about 240 µm, about 30 µm to about 230 µm, about 30 µm to about 230 µm, about 40 µm to about 230 µm, about 50 µm to about 230 µm, about 60 µm to about 230 µm, about 70 µm to about 230 µm, about 80 µm to about 230 µm, about 90 µm to about 230 µm, about 100 µm to about 230 µm, about 110 µm to about 230 µm, about 120 µm to about 230 µm, about 130 µm to about 230 µm, about 140 µm to about 230 µm, about 150 µm to about 230 µm, about 160 µm to about 230 µm, about 170 µm to about 230 µm, about 180 µm to about 230 µm, about 190 µm to about 230 µm, about 200 µm to about 230 µm, about 210 µm to about 230 µm, about 220 µm to about 230 µm, about 30 µm to about 220 µm, about 40 µm to about 220 µm, about 50 µm to about 220 µm, about 60 µm to about 220 µm, about 70 µm to about 220 µm, about 80 µm to about 220 µm, about 90 µm to about 220 µm, about 100 µm to about 220 µm, about 110 µm to about 220 µm, about 120 µm to about 220 µm, about 140 µm to about 220 µm, about 150 µm to about 220 µm, about 160 µm to about 220 µm, about 170 µm to about 220 µm, about 180 µm to about 220 µm, about 190 µm to about 220 µm, about 200 µm to about 220 µm, about 210 µm to about 220 µm, about 30 µm to about 210 µm, about 40 µm to about 210 µm, about 50 µm to about 210 µm, about 60 µm to about 210 µm, about 70 µm to about 210 µm, about 80 µm to about 210 µm, about 90 µm to about 210 µm, about 100 µm to about 210 µm, about 110 µm to about 210 µm, about 120 µm to about 210 µm, about 130 µm to about 210 µm, about 140 µm to about 210 µm, about 150 µm to about 210 µm, about 160 µm to about 210 µm, about 170 µm to about 210 µm, about 180 µm to about 210 µm, about 190 µm to about 210 µm, about 200 µm to about 210 µm, about 30 µm to about 200 µm, about 40 µm to about 200 µm, about 50 µm to about 200 µm, about 60 µm to about 200 µm, about 70 µm to about 200 µm, about 80 µm to about 200 µm, about 90 µm to about 200 µm, about 100 µm to about 200 µm, about 110 µm to about 200 µm, about 120 µm to about 200 µm, about 130 µm to about 200 µm, about 140 µm to about 200 µm, about 150 µm to about 200 µm, about 160 µm to about 200 µm, about 170 µm to about 200 µm, about 180 µm to about 200 µm, about 190 µm to about 200 µm, about 30 µm to about 190 µm, about 40 µm to about 190 µm, about 50 µm to about 190 µm, about 60 µm to about 190 µm, about 70 µm to about 190 µm, about 80 µm to about 190 µm, about 90 µm to about 190 µm, about 100 µm to about 190 µm, about 110 µm to about 190 µm, about 120 µm to about 190 µm, about 130 µm to about 190 µm, about 140 µm to about 190 µm, about 150 µm to about 190 µm, about 160 µm to about 190 µm, about 170 µm to about 190 µm, about 180 µm to about 190 µm, about 30 µm to about 180 µm, about 40 µm to about 180 µm, about 50 µm to about 180 µm, about 60 µm to about 180 µm, about 70 µm to about 180 µm, about 80 µm to about 180 µm, about 90 µm to about 180 µm, about 100 µm to about 180 µm, about 110 µm to about 180 µm, about 120 µm to about 180 µm, about 130 µm to about 180 µm, about 140 µm to about 180 µm, about 150 µm to about 180 µm, about 160 µm to about 180 µm, about 170 µm to about 180 µm, about 30 µm to about 170 µm, about 40 µm to about 170 µm, about 50 µm to about 170 µm, about 60 µm to about 170 µm, about 70 µm to about 170 µm, about 80 µm to about 170 µm, about 90 µm to about 170 µm, about 100 µm to about 170 µm, about 110 µm to about 170 µm, about 120 µm to about 170 µm, about 130 µm to about 170 µm, about 140 µm to about 170 µm, about 150 µm to about 170 µm, about 160 µm to about 170 µm, about 30 µm to about 160 µm, about 40 µm to about 160 µm, about 50 µm to about 160 µm, about 60 µm to about 160 µm, about 70 µm to about 160 µm, about 80 µm to about 160 µm, about 90 µm to about 160 µm, about 100 µm to about 160 µm, about 110 µm to about 160 µm, about 120 µm to about 160 µm, about 130 µm to about 160 µm, about 140 µm to about 160 µm, about 150 µm to about 160 µm, about 30 µm to about 150 µm, about 40 µm to about 150 µm, about 50 µm to about 150 µm, about 60 µm to about 150 µm, about 70 µm to about 150 µm, about 80 µm to about 150 µm, about 90 µm to about 150 µm, about 100 µm to about 150 µm, about 110 µm to about 150 µm, about 120 µm to about 150 µm, about 130 µm to about 150 µm, about 140 µm to about 150 µm, about 30 µm to about 140 µm, about 40 µm to about 140 µm, about 50 µm to about 140 µm, about 60 µm to about 140 µm, about 70 µm to about 140 µm, about 80 µm to about 140 µm, about 90 µm to about 140 µm, about 100 µm to about 140 µm, about 110 µm to about 140 µm, about 120 µm to about 140 µm, about 130 µm to about 140 µm, about 30 µm to about 130 µm, about 40 µm to about 130 µm, about 50 µm to about 130 µm, about 60 µm to about 130 µm, about 70 µm to about 130 µm, about 80 µm to about 130 µm, about 90 µm to about 130 µm, about 100 µm to about 130 µm, about 110 µm to about 130 µm, about 120 µm to about 130 µm, about 30 µm to about 120 µm, about 40 µm to about 120 µm, about 50 µm to about 120 µm, about 60 µm to about 120 µm, about 70 µm to about 120 µm, about 80 µm to about 120 µm, about 90 µm to about 120 µm, about 100 µm to about 120 µm, about 110 µm to about 120 µm, about 30 µm to about 110 µm, about 40 µm to about 110 µm, about 50 µm to about 110 µm, about 60 µm to about 110 µm, about 70 µm to about 110 µm, about 80 µm to about 110 µm, about 90 µm to about 110 µm, about 100 µm to about 110 µm, about 30 µm to about 100 µm, about 40 µm to about 100 µm, about 50 µm to about 100 µm, about 60 µm to about 100 µm, about 70 µm to about 100 µm, about 80 µm to about 100 µm, about 90 µm to about 100 µm, about 30 µm to about 90 µm, about 40 µm to about 90 µm, about 50 µm to about 90 µm, about 60 µm to about 90 µm, about 70 µm to about 90 µm, about 80 µm to about 90 µm, about 30 µm to about 80 µm, about 40 µm to about 80 µm, about 50 µm to about 80 µm, about 60 µm to about 80 µm, about 70 µm to about 80 µm, about 30 µm to about 70 µm, about 40 µm to about 70 µm, about 50 µm to about 70 µm, about 60 µm to about 70 µm, about 30 µm to about 60 µm, about 40 µm to about 60 µm, about 50 µm to about 60 µm, about 30 µm to about 50 µm, about 40 µm to about 50 µm, or about 30 µm to about 40 µm.

The grafts disclosed herein can be shaped to fit the target region of a subject's tissue. The grafts can be custom-designed for an individual subject, with designing taking place according to some embodiments before production of the graft, and according to some embodiments during production of the graft. Designing the graft during its production allows for real-time formation of the graft to ensure proper fitment and/or incorporation of appropriate matrices, growth factors, and/or cell compositions.

According to some embodiments, the grafts disclosed herein can be used fresh or cryo-preserved for later use. Grafts can be cryo-preserved in any biocompatible container, e.g., cryocyte freezing containers, using any cryopreservation method known in the art.

According to some embodiments, the target region of an implant site can be imaged before extraction to determine exact dimensions and geometry of the target region, and a custom graft made to the exact dimensions of the target region. Imaging provides information of the patient's anatomy at the proposed implant site. Exemplary imaging modalities include, without limitation, intra-oral (periapical, occlusal), extra-oral (panoramic, lateral cephalometric) radiographs, conventional X-rays, computed tomography (CT), and cone beam computed tomography (CBCT). Multiple factors influence the selection of radiographic techniques for a particular case including cost, availability, radiation exposure, and patient's anatomy. The objectives of imaging are, e.g., to decide whether implant treatment is appropriate for the patient, to identify the location of vital anatomical structures such as the inferior alveolar nerve and maxillary sinus, to ascertain bone quantity, height, buccolingual width, and angulation of alveolar process, to detect any possible pathological conditions, and also to decide the length and width of the implant to be placed.

According to some such embodiments, the custom graft is a described graft for bony tissue repair. According to some such embodiments, the custom graft is a described graft for soft tissue repair. According to some such embodiments, the custom graft is a described combination graft for bony and soft tissue repair. According to some embodiments, the graft can be prefabricated in a range of sizes, dimensions and geometry. According to some embodiments, one or more of the prefabricated graft(s) can be stored in liquid nitrogen for later use. According to some embodiments, a plurality of the grafts can be prefabricated in a range of sizes, dimensions and geometry for a plurality of target implant sites. According to some embodiments, the plurality of grafts prefabricated in a range of sizes, dimensions and geometry for a plurality of target implant sites can be stored in liquid nitrogen for later use. According to some embodiments, a collection of such grafts when stored comprise a graft bank.

Any conventional method of forming the graft to the target location in a subject may be utilized with the grafts disclosed herein. The graft may be formed in the shape of a cuboid, spheroid, ovoid, ellipsoid, or other irregular shape, and with ends that may be rounded, squared, tapered, beveled, conical, concave, convex, scalloped, angular, or in some other form. Additionally, the graft may be formed in one shape and then filed, drilled, sanded, cut, milled, or grinded into another shape. The optimal shape and dimensions for the graft depend on the size and location of the tissue target and the presence of other materials.

According to some embodiments, the grafts are formed by three-dimensional (3D) printing. 3D printing allows for the production of three dimensional solid objects from a digital file. In a layering process, one layer is added after the other until a fully formed object is produced. 3D printing methods are summarized in, for example, Sawkins et al., Recent Pat. Biomed. Eng. 6:3-21 (2013). Except as otherwise noted herein, therefore, methods, systems, and compositions described herein can be carried out in accordance with, or adapted to, such processes.

A conventional camera, according to some embodiments a 3D camera, may be used to photograph the target graft location in a naturally-occurring state. Additional cameras may be provided for stereoscopic vision. The camera(s) provide image data to an imaging computer, which utilizes commercially available software to create an imaging file of a type commonly utilized to operate a 3D printer in making an article.

The 3D printed graft can be a porous, microcellular graft of a biocompatible material that provides a physical support or an adhesive substrate for recruitment or growth of cells during in vitro or in vivo culturing. The three-dimensional carrier matrix in a 3D printed graft can have an adequate porosity and an adequate pore size so as to facilitate cell recruitment and diffusion throughout the whole structure of both cells and nutrients. The three-dimensional carrier matrix can be biodegradable providing for absorption of the matrix by the surrounding tissues, which can eliminate the necessity of a surgical removal. The rate at which degradation occurs can coincide as much as possible with the rate of tissue or organ formation. Thus, while cells are fabricating their own natural structure around themselves, the three-dimensional carrier matrix can provide structural integrity and eventually break down leaving newly formed tissue which can assume the mechanical load.

According to some embodiments, combination grafts comprising both soft and hard tissue can be produced by 3D printing. In such embodiments, the graft can comprise both a soft tissue scaffold and a hard tissue scaffold, each with the same or different three-dimensional carrier matrix. Such grafts can contain one or more independently selected growth factor compositions and one or more independently selected cell types.

The graft can be printed onto a substrate that includes one or more of glass, poloxamer, polytetrafluoro-ethylene (PTFE), and metal foil, e.g., aluminum foil. Once manufacture is complete, the graft is removed from the 3D printer's printing surface and cured, if necessary, by one or more methods, which may include for example, heat curing, curing by UV light, carbon dioxide or other gas, pressure, or cooling.

A computer is used to control the 3D printer and associated equipment. The computer can include software to create manufacturing instructions for a graft to be printed. The instructions for implementing the processes, methods, and/or techniques discussed herein can be provided on non-transitory computer-readable storage media or memories, such as a cache, buffer, RAM, removable media, hard drive, or other computer readable storage media. Non-transitory computer readable storage media include various types of volatile and nonvolatile storage media.

The 3D printer can be any now known or later developed 3D printer capable of printing the hard and/or soft tissue described herein. Multiple reservoirs for different graft materials may be provided. Under the control of the computer, a deposit head(s) and/or a support platform of the 3D printer are moved to add successive graft material in layers, building up the three-dimensional construction until a physical model of the three-dimensional print construction is created. Any additive manufacturing system may be used.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

As used herein, the articles "a", "an", and "the" preceding an element or component of the invention are intended to be nonrestrictive regarding the number of instances (i.e., occurrences) of the element or component. Therefore "a", "an", and "the" should be read to include one or at least one, and the singular word form of the element or component also includes the plural unless the number is obviously meant to be singular.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention. For example, when a range of "1 to 5" is recited, the recited range should be construed as including ranges "1 to 4", "1 to 3", "1-2", "1-2 & 4-5", "1-3 & 5", and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. A Combination Graft Product for Bony Tissue Repair (CG_BTR) Including Extraction Socket and Ridge Management and Augmentation The extraction of a tooth from its socket (meaning a hollow in the alveolar process of the maxilla or mandible into which each tooth fits), which is surrounded and supported by bone, is a common dental procedure. In extraction, one or more teeth are removed from their sockets with care. When necessary, it is usually an uncomplicated surgery for both the patient and the dentist performing the extraction.

There are times however when one or a series of extractions can cause the soft tissues, bone or both to collapse. The term "ridge or socket preservation" describes the dental surgery performed to prevent this collapse.

Ridge preservation involves placing a regenerative bone grafting material into the one or many empty tooth sockets to rebuild the bone where extraction has left an empty weakened area. Hard tissue ridge augmentations can be performed to recreate adequate bone dimensions prior to dental implant therapy.

Ridge preservation surgery is most useful in preserving the contour and natural appearance of the gingiva and jaw, in providing appropriate support for dentures, dental bridge construction, or orthodontic appliances (e.g., Invisallign®)), and in providing sufficient bone height to support dental implants.

An exemplified product for hard tissue ridge management and augmentation comprises a scaffold/carrier matrix; a growth factor composition, and a cell composition.

The scaffold/carrier matrix of the dental implant product comprises one or more of: a synthetic collagen; a natural collagen matrix; tri-calcium phosphate (TCP); demineralized bone (DBM); extracted dentin, or amnion/chorion membranes.

The growth factor composition comprises PRF containing autologous re-calcified liquid PRP.

The cell composition comprises a population of cells suspended in a culture medium. The population of cells is one or more of fibroblasts, amniotic fluid-derived stomal cells; bone marrow aspirate-derived stromal cells; adipose-derived stem cells, tooth/pulp derived stem cells or umbilical cord stem cells.

A method for preparing the combination graft (CG) product for bony tissue repair comprises:
1) Producing liquid PRF from peripheral blood of the subject;
2) Mixing the liquid PRF and a cell culture composition in a 10:1 or greater, volume to volume PRF to cell culture ratio;
3) Centrifuging the mixture into a scaffold/carrier matrix in an appropriate sized, sterile centrifuge vessel at 3500 to 3500×g (RCF) for 20 minutes; and
4) Sterilely decanting the complete combination graft into a sterile surgical field.

Example 2. A Combination Graft Product for Soft Tissue Repair (CG-STR) Including Thin Biotype/Gingival Augmentation, Enhancement and Management Soft tissue ridge augmentations are performed to enhance the cleansability and aesthetics of a deficient site prior to its final restoration. During this procedure, an incision is made to expose the bony ridge. A soft tissue graft is then inserted into the area, the gum tissue readapted over the soft tissue graft and sutured into place.

The exemplified product comprises a flexible carrier matrix for soft tissue repair, a growth factor composition in form of liquid PRF, and a cell composition.

The flexible carrier matrix comprises one or more of collagen; a fibrin gel or membrane; amnion membrane, chorion membrane; or a synthetic absorbable mesh membrane. The collagen can be type 1 collagen, human collagen, or bovine collagen. The fibrin gel or fibrin membrane can be autologous. The synthetic absorbable mesh/membrane can be PGA, PLA, or PLGA.

The growth factor composition comprises PRF containing autologous liquid PRP.

The cell composition comprises a population of cells suspended in a culture medium. The population of cells is one or more of fibroblasts, epithelial keratinocytes, amniotic fluid-derived stomal cells; bone marrow aspirate-derived stromal cells; adipose-derived stem cells, tooth/pulp-derived stem cells or umbilical cord stem cells.

A process for making the exemplified product comprises:
1) Preparing PRF from peripheral blood of a subject.
2) Mixing the liquid PRF and cell culture in a 10:1 or greater, volume to volume PRF to cell culture ratio;
3) Centrifuging the mixture into a flexible carrier matrix in an appropriate sized, sterile centrifuge vessel pre-loaded with 0.1 mL of a 1M sterile calcium chloride solution at 3500 to 3500×g (RCF) for 20 minutes;
4) Sterilely decanting the complete combination graft into a sterile surgical field.

Example 3. A Combination 3D-SMART Graft Product for Both Bone and Soft Tissue Repair Hard tissue ridge augmentation can be performed in combination with a soft tissue augmentation to simultaneously enhance the soft tissue profile of the deficient site.

The exemplified product comprises a treatment site-specific, pre-shaped dimension 3D scaffold comprising an inner layer and an outer layer. The inner layer is printed with nanocrystalline, granular or morcellated scaffold material and coprinted with a first cell composition. The outer layer comprises a second cell composition.

The product comprises a treatment site-specific, pre-shaped dimension, 3D scaffold.

The scaffold comprises an inner layer and an outer layer:
The inner layer of the scaffold is effective for the promotion of new bone growth, maturation and remodeling.
The inner layer is printed with a nanocrystalline, granular or morcellated scaffold material. The nanocrystalline, granular or morcellated scaffold material comprises: a synthetic bone matrix (e.g., tri-calcium phosphate with collagen); DBM; amnion membrane, chorion membrane or both; or extracted dentin.

The scaffold material is co-printed with a first cell culture composition. The first cell culture composition, together with a growth factor composition comprising autologous PRP, comprises a population of cells suspended in culture medium, wherein the population of cells is one or more of: fibroblasts, amniotic fluid derived stromal cells; bone marrow aspirate-derived stromal cells; adipose derived stem cells; tooth/pulp-derived stem cells; or umbilical cord stem cells.

The outer layer of the scaffold is effective for the promotion of new epithelial soft tissue growth and maturation.

The outer layer comprises, together with the growth factor composition, a second cell composition comprising a population of cells suspended in culture medium, wherein the population of cells is one or more of: fibroblasts, gingival epithelial keratinocytes; amniotic fluid derived stromal cells; bone marrow aspirate-derived stromal cells; adipose-derived stem cells; tooth/pulp-derived stem cells or umbilical cord stem cells.

Example 4. A Combination Graft Product for Percutaneous Injection (Cg-Btr) for Bony and Soft Tissue Repair, Including Extraction Socket and Ridge Management and Augmentation Hard tissue ridge augmentation can be performed in combination with a soft tissue augmentation to simultaneously enhance the soft tissue profile of the deficient site.

The exemplified product comprises a scaffold/carrier matrix; a growth composition, and a cell composition.

The scaffold/carrier matrix comprises one or more of a synthetic collagen, a natural collagen matrix, an amnion membrane or chorion membrane.

The growth factor composition comprises platelet rich fibrin comprising autologous re-calcified liquid platelet rich plasma.

The cell composition comprises a population of cells suspended in culture medium, the population of cells is one or more of: fibroblasts, amniotic fluid-derived stromal cells; bone marrow aspirate-derived stromal cells; adipose-derived stem cells; tooth/pulp-derived stem cells; or umbilical cord stem cells.

A method for preparing the described combination graft product comprises:
1) Preparing liquid PRF from peripheral blood of a subject;
2) Mixing the liquid PRF and a cell composition in a 10:1 or greater volume to volume PRF to cell composition ratio;
3) Centrifuging the mixture into a scaffold/carrier matrix in an appropriate sized, sterile centrifuge vessel at 1500×g (RCF) for 10 minutes;
4) Sterilely decanting the combination graft product onto a sterile surgical field.

While the invention has been described with reference to specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A multilayer combination hard and soft tissue graft comprising:
   a treatment site specific, pre-shaped dimension, three-dimensional scaffold comprising
   (I) an inner layer comprising:
      (1) a first three-dimensional carrier matrix comprising one or more of a collagen, tri-calcium phosphate, de-mineralized bone strips, de-mineralized bone particles, dentin, an amnion membrane, or a chorion membrane;
      (2) a first growth factor composition comprising platelet-rich fibrin; and
      (3) a first cell culture composition comprising:
         (a) a first culture medium,
         (b) a first population of cells suspended in the culture medium, and
         (c) a first population of cells impregnated in or on a surface of particles of a diameter from about 30 μm to about 40 μm; wherein the particles are osteoconductive;
      wherein a ratio of the first growth factor composition to the first cell culture composition in the graft is at least about 10:1 (v/v); and
   (II) an outer layer comprising:
      (1) a second flexible three-dimensional carrier matrix comprising one or more of a collagen, a fibrin gel, a fibrin membrane, an amnion membrane, a chorion membrane, a synthetic absorbable mesh selected from the group consisting of a polylactic acid (PLA) mesh, a PLA membrane, a poly(glycolide-co-lactide) copolymer (PLGA) membrane, a PLGA mesh, and a PLA/PGLA mesh; a synthetic absorbable membrane selected from the group consisting of a PLA membrane, a poly(glycolide-co-lactide) copolymer (PLGA) membrane, and a PLA/PGLA membrane; a PLA mesh/PGLA membrane, or a PLA membrane/PGLA mesh;
      (2) a second growth factor composition comprising platelet-rich fibrin; and
      (3) a second cell culture composition comprising:
         (i) a second culture medium,
         (ii) a second population of cells suspended in the culture medium, and
         (iii) cells impregnated on a surface of particles of a diameter from about 30 μm to about 40 μm;
      wherein the ratio of second growth factor composition to second cell culture composition in the graft is at least about 10:1 (v/v);
      wherein the first carrier matrix is supersaturated by the first population of cells, and the second carrier matrix is supersaturated by the second population of cells, and
      wherein the graft is effective to regenerate a target hard tissue and a target soft tissue.

2. The combination hard and soft tissue graft of claim 1, wherein the inner layer of the scaffold is effective to regenerate bone, and the outer layer of the scaffold is effective to regenerate epithelial soft tissue.

3. The combination hard and soft tissue graft of claim 1, wherein the first growth factor composition, the second growth factor composition, or both comprises one or more cytokine selected from the group consisting of vascular endothelial growth factor (VEGF), platelet-derived growth factor (PDGF), transforming growth factor-β (TGF-β), bone morphogenetic protein-2 (BMP-2), bone morphogenetic protein-7 (BMP-7), interleukin-1 (IL-1), epidermal growth factor (EGF), insulin-like growth factor (IGF-1), fibronectin, fibroblast growth factor (FGF), and neural epidermal growth-factor-like 1 (NELL1).

4. The combination hard and soft tissue graft of claim 1, wherein the platelet rich fibrin contains platelet rich plasma.

5. The combination hard and soft tissue graft of claim 1, wherein the first population of cells suspended in the first culture medium of the first cell composition comprises autologous expanded fibroblasts, autologous stromal cells, allogeneic stromal cells; autologous mesenchymal stem cells, or allogeneic mesenchymal stem cells, and wherein the carrier matrix is supersaturated by the suspended population of cells.

6. The combination hard and soft tissue graft of claim 5, wherein the suspended stromal cells comprise allogeneic amniotic fluid-derived stromal cells or autologous, expanded bone marrow aspirate derived stromal cells.

7. The combination hard and soft tissue graft of claim 5, wherein the suspended mesenchymal stem cells comprise autologous adipose-derived mesenchymal stem cells, autologous expanded tooth/pulp-derived mesenchymal stem cells, or allogeneic umbilical cord stem cells.

8. The combination hard and soft tissue graft of claim 1, wherein the second population of cells suspended in the second culture medium of the second cell composition comprises autologous expanded fibroblasts, autologous expanded gingival epithelial keratinocytes; autologous expanded stromal cells, allogeneic stromal cells; autologous mesenchymal stem cells or allogeneic mesenchymal stem cells.

9. The combination hard and soft tissue graft of 8, wherein the suspended stromal cells comprise allogeneic amniotic fluid-derived stromal cells or autologous, expanded bone marrow aspirate derived stromal cells.

10. The combination hard and soft tissue graft of 8, wherein the suspended mesenchymal stem cells comprise autologous adipose-derived mesenchymal stem cells, autologous expanded tooth/pulp-derived mesenchymal stem cells, or allogeneic umbilical cord stem cells.

11. The combination hard and soft tissue graft of claim 1, wherein the inner layer of the scaffold, the outer layer of the scaffold or both the inner layer and outer layer of the scaffold is/are formed by a 3D printer.

12. The combination hard and soft tissue graft of claim 1, wherein the first growth factor composition and the second growth factor composition are the same.

13. The combination hard and soft tissue graft of claim 1, wherein the graft is adapted for percutaneous injection for bony and soft tissue repair.

14. The combination hard and soft tissue graft of claim 1, wherein each of the first carrier matrix supersaturated by the first population of cells, and the carrier matrix supersaturated by the second population of cells comprises at least 10,000,000 cells.

15. A dental implant comprising the combination hard and soft tissue graft of claim 1.

16. A bone implant comprising the combination hard and soft tissue graft of claim 1.

17. A method of producing a multilayer combination hard and soft tissue graft comprising:
- (a) preparing a growth factor composition comprising platelet-rich fibrin from peripheral blood of a subject;
- (b) preparing a first cell culture composition by expanding in vitro a first suspended population of cells in a first culture medium comprising particles of a diameter from about 30 μm to about 40 μm, the first cell culture composition comprising a first population of cells suspended in the first culture medium and a first population of cells impregnated in or on a surface of the particles;
- (c) mixing a first portion of the growth factor composition with the first cell culture composition in a ratio of growth factor composition to cell culture composition of at least about 10:1 (v/v) to form a first growth factor composition—first cell culture composition mixture;
- (d) combining the first growth factor composition—first cell culture composition mixture of step (c) with a first three-dimensional carrier matrix comprising one or more of a collagen, tri-calcium phosphate, de-mineralized bone strips, de-mineralized bone particles, dentin, an amnion membrane, or a chorion membrane to form an inner layer of the multilayer graft; wherein the first carrier matrix is supersaturated by the first population of cells,
- (e) preparing a second cell culture composition by expanding in vitro a second suspended population of cells in a second culture medium comprising particles of a diameter from about 30 μm to about 40 μm, the second cell culture composition comprising a second population of cells suspended in the culture medium and a second population of cells impregnated on the surface of the particles;
- (f) mixing a second portion of the growth factor composition with the second cell culture composition in a ratio of growth factor composition to cell culture composition of at least about 10:1 (v/v) to form a second growth factor composition—second cell culture composition mixture;
- (g) combining the second growth factor composition—second cell culture composition mixture of step (f) with a second three-dimensional carrier matrix comprising one or more of a collagen, a fibrin gel, a fibrin membrane, a fibrin matrix, a hyaluronic acid membrane, an amnion membrane, a chorion membrane, an amnion/chorion membrane, a synthetic absorbable mesh selected from the group consisting of a polylactic acid (PLA) mesh, PLA membrane, poly(glycolide-co-lactide) copolymer (PLGA) membrane, a PLGA mesh, and a PLA/PGLA mesh; a synthetic absorbable membrane selected from the group consisting of a PLA membrane, a poly(glycolide-co-lactide) copolymer (PLGA) membrane, and a PLA/PGLA membrane; a PLA mesh/PGLA membrane, or a PLA membrane/PGLA mesh to form an outer layer of the graft; wherein the second carrier matrix is supersaturated by the second population of cells, and
- (h) layering the inner layer over the outer layer to form the multilayer graft.

18. The method of claim 17, wherein the inner layer of the scaffold is effective to regenerate bone, and the outer layer of the scaffold is effective to regenerate epithelial soft tissue.

19. The method of claim 17, wherein the growth factor composition comprises one or more cytokine selected from the group consisting of vascular endothelial growth factor (VEGF), platelet-derived growth factor (PDGF), transforming growth factor-β (TGF-β), bone morphogenetic protein-2 (BMP-2), bone morphogenetic protein-7 (BMP-7), interleukin-1 (IL-1), epidermal growth factor (EGF), insulin-like growth factor (IGF-1), fibronectin, fibroblast growth factor (FGF), and neural epidermal growth-factor-like 1 (NELL1).

20. The method of claim 17, wherein the platelet rich fibrin contains platelet rich plasma.

21. The method of claim 17, wherein the first population of cells suspended in the first culture medium of the first cell composition comprises autologous expanded fibroblasts, autologous stromal cells, allogeneic stromal cells; autologous mesenchymal stem cells, or allogeneic mesenchymal stem cells, and wherein the carrier matrix is supersaturated by the suspended population of cells.

22. The method of claim 21, wherein the suspended stromal cells comprise allogeneic amniotic fluid-derived stromal cells or autologous, expanded bone marrow aspirate derived stromal cells.

23. The method of claim 21, wherein the suspended mesenchymal stem cells comprise autologous adipose-derived mesenchymal stem cells, autologous expanded tooth/pulp-derived mesenchymal stem cells, or allogeneic umbilical cord stem cells.

24. The method of claim 17, wherein the second population of cells suspended in the second culture medium of the second cell composition comprises autologous expanded fibroblasts, autologous expanded gingival epithelial keratinocytes; autologous expanded stromal cells, allogeneic stromal cells; autologous mesenchymal stem cells or allogeneic mesenchymal stem cells.

25. The method of claim 24, wherein the suspended stromal cells comprise allogeneic amniotic fluid-derived stromal cells or autologous, expanded bone marrow aspirate derived stromal cells.

26. The method of claim 24, wherein the suspended mesenchymal stem cells comprise autologous adipose-derived mesenchymal stem cells, autologous expanded tooth/pulp-derived mesenchymal stem cells, or allogeneic umbilical cord stem cells.

27. The method of claim 17, comprising forming the inner layer of the scaffold of step (d) by co-printing steps (a), (b) and (c) with a 3D printer.

28. The method of claim 17, comprising forming the outer layer of the scaffold of step (g) by co-printing steps (d), (e) and (f) with a 3D printer.

29. The method of claim 17, wherein the layering in step (h) is achieved with a 3D printer.

30. The method of claim 17, comprising combining the growth factor composition—first cell culture composition mixture with the first three-dimensional carrier matrix by centrifugation.

31. The method of claim 17, comprising combining the growth factor composition—second cell culture composition mixture with the second three-dimensional carrier matrix by centrifugation.

32. The method of claim 17, wherein each of the first carrier matrix supersaturated by the first population of cells, and the carrier matrix supersaturated by the second population of cells comprises at least 10,000,000 cells.

33. The method of claim 17, step (b) comprising expanding the first population of cells in an automated cell reactor comprising capillary fibers, wherein the capillary fibers contain a coated inner surface, and wherein the cells become attached to the coated inner surface.

34. The method according to claim 33, step (b) further comprising adding additional cells to the cell culture composition by centrifugation.

35. The method of claim 17, step (e) comprising expanding the second population of cells in an automated cell reactor comprising capillary fibers, wherein the capillary fibers contain a coated inner surface, and wherein the cells becomes attached to the coated inner surface.

36. The method according to claim 35, step (b) further comprising adding additional cells to the cell culture composition by centrifugation.

37. The method according to claim 17, further comprising prefabricating the graft in a range of sizes, dimensions and geometry for one or more target implant sites, and storing the prefabricated grafts in liquid nitrogen for later use, wherein a collection of such grafts when stored comprises a graft bank.

38. A dental implant comprising the combination hard and soft tissue graft produced by the method of claim 17.

39. A bone implant comprising the combination hard and soft tissue graft produced by the method of claim 17.

* * * * *